United States Patent [19]

Lollar et al.

[11] Patent Number: 5,744,446
[45] Date of Patent: Apr. 28, 1998

[54] HYBRID HUMAN/ANIMAL FACTOR VIII

[75] Inventors: John S. Lollar, Decatur, Ga.;
Marschall S. Runge, Galveston, Tex.

[73] Assignee: Emory University, Atlanta, Ga.

[21] Appl. No.: 474,503

[22] Filed: Jun. 7, 1995

Related U.S. Application Data

[63] Continuation-in-part of Ser. No. 212,133, Mar. 11, 1994, Pat. No. 5,663,060, which is a continuation of Ser. No. 864,004, Apr. 7, 1992, Pat. No. 5,364,771.

[51] Int. Cl.$^6$ .................... A61K 38/00; C12P 21/04; C12N 15/00; C07K 14/755
[52] U.S. Cl. .................... 514/12; 435/69.6; 435/172.3; 424/185.1; 530/383; 930/100
[58] Field of Search .................... 435/69.6, 172.3; 530/383; 514/12; 930/100; 424/185.1

[56] References Cited

U.S. PATENT DOCUMENTS

| | | | |
|---|---|---|---|
| Re. 32,011 | 10/1985 | Zimmerman et al. | 260/112 |
| 4,554,101 | 11/1985 | Hopp | 530/324 |
| 4,757,006 | 7/1988 | Toole et al. | 435/70 |
| 4,868,112 | 9/1989 | Toole, Jr. | 514/8 |
| 4,965,199 | 10/1990 | Capon et al. | 435/69.6 |
| 4,970,300 | 11/1990 | Fulton et al. | 530/383 |
| 4,980,456 | 12/1990 | Scandella et al. | 530/383 |
| 5,004,803 | 4/1991 | Kaufman et al. | 530/383 |
| 5,246,850 | 9/1993 | Bennett et al. | 435/359 |

FOREIGN PATENT DOCUMENTS

| | | |
|---|---|---|
| WO 91/09122 | 6/1991 | WIPO. |
| WO 92/16557 | 10/1992 | WIPO. |
| WO 94/11503 | 5/1994 | WIPO. |

OTHER PUBLICATIONS

Lollar, P. et al. (1994) "Inhibition of Human Factor VIIIa by Anti-A2 Subunit Antibodies" *J. Clin. Invest.* 93:2497–2504.
Gilles, Jean Guy and N.-M. R. Saint-Remy (1994) "Healthy Subjects Produce both Anti-Factor VIII and Specific Anti-Idiotype Antibodies" *J. Clin. Invest*, 94:1496–1505.
Hoyer, L.W. and D. Scandella (1994) "Factor VIII Inhibitors: Structure and Function in Autoantibody and Hemophilia A Patients" *Seminars in Hematology* 31(2)(4):1–5.
Hoeben, R.C. (1990) "Expression of Functional Factor VIII In Primary Human Skin Fibroblasts after Retrovirus-medicated Gene Transfer" *J. Biol. Chem.* 265(13):7318–7323.
Pittman, D.D., et al., (1992) "A2 Domain of Human Recombinant-Derived Factor VIII is Required for Procoagulant Activity but not for Thrombin Cleavage," *Blood* 79(2):389–397.
Brinkhouse, K.M. et al., (1985) "Purified Human Factor VIII Procoagulant Protein: Comparative Hemostatic Resonce After Infusions into Hemophilia and von Willebrand Disease Dogs," *Proc. Natl. Acad, Sci. U.S.A.*, 82:8752–8755.
Elder, B., et al. (1993) "Sequence of the Murine Factor VIII cDNA," *Genomics* 16(2):374–379.

Hoeben, R.C. et al. (1993) "Toward Gene Therapy for Hemophilia A: Long-Term Persistence for Factor VIII-Secreting Fibroblasts After Transplantation into Immunodeficient Mice," *Human Gene Therapy*, 4(2):179–186.
Horn, R.M., et al. (1993) "Gene Splicing by Overlap Extension," *Meth. Enzymol* 217:270.
Levinson, B. et al. (1992) "Sequence of the Human Factor VIII-Associated Gene is Conserved in Mouse," *Genomics* 13:862–865.
Lollar, P., et al. (1993) "Inhibition of Human Factor VIIIa by Anti-A2 Subunit Antibodies," *Blood* 82:Abstracts No. 230.
Lollar, P., et al. (1992) "Coagulant Properties of Hybrid Human-Porcine Factor VIII Molecules," *J. Biol. Chem.* 267:23652–23657.
Lubin, I.M., et al. (1994) "Elimination of a Major Inhibitor Epitope In Factor VIII," *J. Biol. Chem.* 269(12):8639–8641.
Lubin, L.M., et al. (1993) "Expression of a Recombinant Hybrid Human/Porcine Factor VIII Molecule with Elimination of Reactivity Toward an Inhibitory Anti-Human A2 Domain Antibody," *Blood* 82:Abstract 229.
Lusher, J.M., et al. (1993) "Recombinant Factor VIII for the Treatment of Previously Untreated Patients with Hemophilia A," *New Engl. J. Med.*, 328(7):453–459.
Rebemtulla, A., (1993) Improved Procoagulant Activity of Human Factor VIII Molecules Containing Portions of Porcine Sequence, *Blood* 82:Abstract 1339.
Sarkar, G., et al. (1989) "Access to a Messenger RNA Sequence or its Protein Product is not limited by Tissue or Species Specificity," *Science* 244:331–334.
Shima, M., et al., (1993) "Factor VIII Neutralizing Monoclonal Antibody and a Human Inhibitor Alloantibody Recognizing Epitopes in the C2 Domain Inhibit Binding to von Willebrand Factor and to Phosphatidyl Serine," *Thromb. Haemostas* 69:240–246.
Scandella, D., et al. (1989) "Localization of Epitopes for Human Factor VIII Inhibitor Antibodies by Immunoblotting and Antibody Neutralization," *Chem. Abst.* 570, 111(25) Abstract 230240.
Scandella, D., et al. (1993) "Localization of Epitopes for Human Factor VIII Inhibitor Antibodies by Immunoblotting and Antibody Neutralization," *Blood* 82(6):1767–1775.
Scandella, D., et al. (1993) "A Recombinant Factor VIII A2 Domain Polypeptide Quantitatively Neutralizes Human Inhibitor Antibodies that Bind to A2," *Chem. Abst.* 782, 121(19) Abstract 268801.

(List continued on next page.)

Primary Examiner—Rebecca E. Prouty
Assistant Examiner—Elizabeth Slobodyansky
Attorney, Agent, or Firm—Greenlee, Winner & Sullivan P.C.

[57] ABSTRACT

Provided is a hybrid Factor VIII having a sequence of amino acids selected from the group of A2 domain fragments 373–540, 373–508, 445–508, 484–508, 404–508, 489–508 and 484–489 according to Seq ID NO 2 substituted with corresponding sequence of porcine or murine Factor VIII. Invention also relates to methods of treatment Factor VIII deficiency with said hybrid Factor VIII.

20 Claims, 2 Drawing Sheets

OTHER PUBLICATIONS

Scandella, D., et al. (1989) "A Recombinant Factor VIII A2 Domain Polypeptide Quantitatively Neutralizes Human Inhibitor Antibodies that Bind to A2," Blood 74(5) 1618–1626.

Arai, M., et al., "Molecular basis of factor VIII by human antobodies," 863 J. Clin. Invest. 1978–1984 (1989).

Burke, R.L., et al., "The functional domains of coaqulation factor VIII:C," 261 J. Biol. Chem. 12574–12578 (1986).

Eaton, D., "Proteolytic processing of human factor VIII, Correlation of specific cleavages by thrombin, factor Xa, and activated protein C with activation and inactivation of factor VIII coagulant activity," 25 Biochem, 505–512 (1986).

Eaton, D.L., et al., "Construction and characterization of an active factor VIII variant lacking the central one–third of the molecule," 25 Biochem. 8343–8347 (1986).

Eaton, D.L., et al., "Characterization of recombinant human factor VIII," 262 J. of Biol. Chem. 3285–3290 (1987).

Fass, D.N., et al., "Monoclonal antibodies to porcine factor VIII coagulant and their use in the Isolation of active coagulant protein," 59 Blood 594–600 (1982).

Fay, P.J., et al., "The size of human factor VIII heterodimers and the effects produced by thromblin," 871 Biochimica et Biophysica Acta 268–278 (1986).

Fay, P.J., "Subunit structure of thrombin–activated human factor VIIIa," 952 Biochlmica et Biophysica Acta 181–190 (19871).

Fay, P.J., "Reconstitution of human factor VIII from Isolated subunits," 262 Arch. Biochem. Biophys. 525–531 (1988).

Fay, P.J., et al., "Topography of the human factor VIII–von Willebrand factor complex," 265 J. Biol. Chem. 6197–6202 (1990).

Fay, P.J., et al., "von Willebrand factor mediates protection of factor VIII from activated protein C–catalyzed inactivation," 266 J. Biol. Chem. 2172–2177 (1991).

Fay, P.J., et al., "Human factor VIII subunit structure," 266 J. Biol. Chem. 1–6 (1991).

Fulcher, C.A., and T.S. Zimmerman, "Characterization of the human factor VIII procoagulant protein with a heterologous precipitating antibody," 79 Proc. Nat'l. Acad. Sci. U.S.A. 1648–1652 (1982).

Fulcher, C.A., et al., "Human factor VIII procoagulant protein," 76 J. Clin. Invest. 117–124 (1985).

Gitschier, J., et al., "Characterization of the human factor VIII gene," 312 Nature 326–330 (1984).

Hill–Eubanks, D.C., and P. Lollar, "von Willebrand factor is a cofactor for thrombin–catalyzed cleavage of the factor VIII light chain," 265 J. Biol. Chem. 17854–17858 (1990).

Kaufman, R.J., et al., "Synthesis, processing, and secretion of recombinant human factor VIII expressed in mammalian cells," 263 J. Biol. Chem. 6352–6362 (1988).

Kaufman, R.J., et al., "Effect of von Willebrand factor coexpression on the synthesis and secretion of factor VIII in Chinese hamster ovary cells," 9 Molec. Cell. Biol. 1233–1242 (1989).

Koedam, J.A., et al., "The effect of von Willebrand factor on activation of factor VIII by factor Xa," 189 Eur. J. Biochem. 229–234 (1990).

Kohn, D.B., and P.W. Kantoff, "Potential applications of gene therapy," 29 Transfusion 812–820 (1989).

Leyte, A., "Sulfation of Tyr$^{100}$ of human blood coagulation factor VIII is essential for the interaction of factor VIII with von Willebrand factor," 266 J. Biol. Chem. 740–746 (1991).

Lollar, P., et al., "Activation of porcine factor VIII:C by thrombin and factor Xa," 24 Biochemistry 8056–8064 (1985).

Lollar, P. (J.S.), et al., "Association of the factor VIII light chain with von Willebrand factor," 263 J. Biol. Chem. 10451 (1988).

Lollar, P.(J.S.), et al., "Molecular characterization of commercial porcine factor VIII concentrate,"71 Blood 137–143 (1988).

Lollar, P. (J.S.), and C.G. Parker, "Subunit structure of thrombin–activated porcine factor VIII," 28 Biochemistry 666–674 (1989).

Lollar, P., and C.G. Parker, "pH–dependent denaturation of thrombin–activated porcine factor VIII," 265 J. Biol. Chem. 1688–1692 (1990).

Lollar, P., "The association of factor VIII with von Willebrand factor," 66 Mayo Clin. Proc. 542–534 (1991).

Lollar, P., and E.T. Parker, "Structural basis for the decreased procoagulant activity of human factor VIII compared to the porcine homolog," 266 J. Biol. Chem. 12481–12486 (1991).

Mosesson, M.W., et al., "Structural model of porcine factor VIII and factor VIIIa molecules based on scanning transmission electron microscope (STEM) images and STEM mass analysis," 85 J.Clin. Invest, 1983–1990 (1990).

Naylor, J.A., et al., "Detection of three novel mutations in two haemophilia A patients by rapid screening of whole essential region of factor VIII gene," 337 The Lancet 635–639 (1991).

Pittman, D.D., and R.J. Kaufman, "Proteolytic requirements for thrombin activation of anti–hemophilic factor (factor VIII)," 85 Proc. Nat'l. Acad, sci. U.S.A. 2429–2433 (1988).

Roberts, H. R., and M. R. Jones, "Hemohilia and related conditions—Congenital defficiencies of prothrombin ( factor II, factor V, and factors VII to XII," Ch. 153, 1453–1474, 1460, in Hematology, Williams, W.J., et al., ed., 1990.

Toole, J.J., et al., "Molecular cloning of a cDNA encoding human antihaemophilic factor," 312 Nature 342–347 (1984).

Toole, J.J., et al., "A large region (≈95 kDa) of human factor VIII is dispensable for in vitro procoagulant activity," 83 Proc Nat'l. Acad. Sci. U.S.A. 5939–5942 (1986).

Walker, F.J., et al., "Identification of the binding site for activated protein C on the light chain of factors V and VIII," 265 J. Biol. Chem. 1484–1489 (1990).

Vehar, G.A., and E.W. Davie, "Preparation and properties of bovine factor VIII (antihemophilic factor)," 19 Biochem. 401–410 (1980).

Vehar, G.A., et al., "Structure of haman factor VIII," 312 Nature 337–342 (1984).

Ware, J., et al., "Localization of a factor VIII–inhibiting antibody epitope to a region between residues 338 and 362 of factor VIII heavy chain," 85 Proc. Natl. Acad. Scil. USA 3165–3169 (1988).

Wood, W.I., et al., "Expression of active human factor VIII from recombinant DNA clones," 321 Nature 330–337 (1984).

FIGURE 1A

```
            373
Pig    SVAKKHPKTWVHYISAEEEDWDYAPAVPSPSDRSYKSLYLNSGPQRIGRKYKKARFVAYT        432
                       1
Hum    SVAKKHPKTWVHYIAAEEEDWDYAPLVLAPDDRSYKSQYLNNGPQRIGRKYKKVRFMAYT        432
       ***** ******* *** ******     *  *   *******  ***********
Mou    SVAKKYPKTWIHYISAEEEDWDYAPSVPTSDNGSYKSQYLSNGPHRIGRKYKKVRFIAYT        432

2                                      3
Pig    DVTFKTRKAIPYESGILGPLLYGEVGDTLLIIFKNKASRPYNIYPHGITDVSALHPGRLL        492
Hum    DETFKTREAIQHESGILGPLLYGEVGDTLLIIFKNQASRPYNIYPHGITDVRPLYSRRLP        492
       * ****** ** **************** *** ****************  *   **
Mou    DETFKTRETIQHESGLLGPLLYGEVGDTLLIIFKNQASRPYNIYPHGITDVSPLHARRLP        492

4
Pig    KGWKHLKDMPILPGETFKYKWTVTVEDGPTKSDPRCLTRYYSSSINLEKDLASGLIGPLL        552
Hum    KGVKHLKDFPILPGEIFKYKWTVTVEDGPTKSDPRCLTRYYSSFVNMERDLASGLIGPLL        552
       ** ***** ****** *************************** *  * **********
Mou    RGIKHVKDLPIHPGEIFKYKWTVTVEDGPTKSDPRCLTRYYSSFINPERDLASGLIGPLL        552

5
Pig    ICYKESVDQRGNQMSDKRNVILFSVFDENQSWYLAENIQRFLPNPDGLQPQDPEFQASN         612
Hum    ICYKESVDQRGNQIMSDKRNVILFSVFDENRSWYLTENIQRFLPNPAGVQLEDPEFQASN        612
       ************* ************** ***** ********** *  *********
Mou    ICYKESVDQRGNQMSDKRNVILFSIFDENQSWYITENMQRFLPNAAKTQPQDPGFQASN         612
```

FIGURE 1B

```
Pig  IMHSINGYVFDSLQLSVCLHEVAYWYILSVGAQTDFLSVFFSGYTFKHKMVYEDTLTLFP    672
         ...........................................................
Hum  IMHSINGYVFDSLQLSVCLHEVAYWYILSIGAQTDFLSVFFSGYTFKHKMVYEDTLTLFP    672
     ******** * *********************** *************************
Mou  IMHSINGYVFDSLELTVCLHEVAYWHILSVGAQTDFLSIFFSGYTFKHKMVYEDTLTLFP    672
                                    6                 7
Pig  FSGETVFMSMENPGLWVLGCHNSDLRNRGMTALLKVYSCDRDIGDYDNTYEDIPGFLLS    732
         ...........................................................
Hum  FSGETVFMSMENPGLWILGCHNSDFRNRGMTALLKVSSCDKNTGDYYEDSYEDISAYLLS   732
     ************** ******** *********** ****  *    ****  *
Mou  FSGETVFMSMENPGLWVLGCHNSDFRKRGMTALLKVSSCDKSTSDYYEEIYEDIPTQLVN   732

Pig  GKNVIEPR                                                       740
         . . . . .
Hum  KNNAIEPR                                                       740
     *  * * *
Mou  ENNVIDPR                                                       740
```

HYBRID HUMAN/ANIMAL FACTOR VIII

This application is a continuation-in-part of PCT/US94/13200 entitled "Hybrid Human/Animal Factor VIII" filed Nov. 15, 1994 by Emory University; which claims priority to U.S. Ser. No. 08/212,133 entitled "Hybrid Human/Animal Factor VIII" filed Mar. 11, 1994 now U.S. Pat. No. 5,663,060 by John S. Lollar and Marschall S. Runge; which is a continuation-in-part of U.S. Ser. No. 07/864,004 entitled "Hybrid Human/Porcine Factor VIII" filed Apr. 7, 1992 by John S. Lollar and Marschall S. Runge, which issued as U.S. Pat. No. 5,364,771 on Nov. 15, 1994.

The government has rights in this invention arising from National Institutes of Health Grant Nos. HL40921, HL46215, and HL36094 that partially funded the research leading to this invention.

BACKGROUND OF THE INVENTION

This invention relates generally to a hybrid factor VIII having human and animal factor VIII amino acid sequence or having human factor VIII and non-factor VIII amino acid sequence and methods of preparation and use thereof.

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Cofactors are required at most of the steps.

Factor VIII circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the protein factor VIIIa is a cofactor that increases the catalytic efficiency of factor IXa toward factor X activation by several orders of magnitude.

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

The development of antibodies ("inhibitors" or "inhibitory antibodies") that inhibit the activity of factor VIII is a serious complication in the management of patients with hemophilia. Autoantibodies develop in approximately 20% of patients with hemophilia A in response to therapeutic infusions of factor VIII. In previously untreated patients with hemophilia A who develop inhibitors, the inhibitor usually develops within one year of treatment. Additionally, autoantibodies that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using factor IX complex preparations (for example, KONYNE®, Proplex®) or recombinant human factor VIIIa. Additionally, since porcine factor VIII usually has substantially less reactivity with inhibitors than human factor VIII, a partially purified porcine factor VIII preparation (HYATE:C®) is used. However, inhibitors may develop to porcine factor VIII after one or more infusions.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contains a significant level of antigenic proteins; a monoclonal antibody-purified factor VIII that has lower levels of antigenic impurities and viral contamination; and recombinant human factor VIII, clinical trials for which are underway. Unfortunately, human factor VIII is unstable at physiologic concentrations and pH, is present in blood at an extremely low concentration (0.2 µg/ml plasma), and has low specific clotting activity.

Hemophiliacs require daily replacement of factor VIII to prevent bleeding and the resulting deforming hemophilic arthropathy. However, supplies have been inadequate and problems in therapeutic use occur due to difficulty in isolation and purification, immunogenicity, and the necessity of removing the AIDS and hepatitis infectivity risk. The use of recombinant human factor VIII or partially-purified porcine factor VIII will not resolve all the problems.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to cause production of inhibitory antibodies; and a factor VIII molecule that evades immune detection in patients who have already acquired antibodies to human factor VIII.

It is therefore an object of the present invention to provide a factor VIII that corrects hemophilia in a patient deficient in factor VIII or having inhibitors to factor VIII.

It is a further object of the present invention to provide methods for treatment of hemophiliacs.

It is still another object of the present invention to provide a factor VIII that is stable at a selected pH and physiologic concentration.

It is yet another object of the present invention to provide a factor VIII that has greater coagulant activity than human factor VIII.

It is an additional object of the present invention to provide a factor VIII against which less antibody is produced.

SUMMARY OF THE INVENTION

The present invention provides isolated, purified, hybrid factor VIII molecules and fragments thereof with coagulant activity including hybrid factor VIII having factor VIII amino acid sequence derived from human and pig or other non-human mammal (together referred to herein as "animal"); or in a second embodiment including a hybrid equivalent factor VIII having factor VIII amino acid sequence derived from human or animal or both and amino acid sequence having no known sequence identity to factor VIII ("non-factor VIII amino acid sequence"), preferably substituted in an antigenic and/or immunogenic region of the factor VIII, is described. One skilled in the art will realize that numerous hybrid factor VIII constructs can be prepared including, but not limited to, human/animal factor VIII having greater coagulant activity than human factor VIII ("superior coagulant activity"); non-immunogenic human/equivalent factor VIII; non-antigenic human/equivalent or human/animal factor VIII; non-immunogenic human/animal or human/equivalent factor VIII having superior coagulant activity; non-antigenic human/animal or human/animal/equivalent factor VIII having superior coagulant activity; non-immunogenic, non-antigenic human/equivalent or human/equivalent/animal factor VIII; and non-immunogenic, non-antigenic human/animal/equivalent factor VIII having superior coagulant activity.

The hybrid factor VIII molecule is produced by isolation and recombination of human and animal factor VIII subunits or domains; or by genetic engineering of the human and animal factor VIII genes.

In a preferred embodiment, recombinant DNA methods are used to substitute elements of animal factor VIII for the corresponding elements of human factor VIII, resulting in hybrid human/animal factor VIII molecules. In a second preferred embodiment, recombinant DNA methods are used to replace one or more amino acids in the human or animal factor VIII or in a hybrid human/animal factor VIII with amino acids that have no known sequence identity to factor VIII, preferably a sequence of amino acids that has less immunoreactivity with naturally occurring inhibitory antibodies to factor VIII ("nonantigenic amino acid sequence") and/or is less apt to elicit the production of antibodies to factor VIII ("non-immunogenic amino acid sequence") than human factor VIII. An example of an amino acid sequence that can be used to replace immunogenic or antigenic sequence is a sequence of alanine residues.

In another embodiment, subunits of factor VIII are isolated and purified from human or animal plasma, and hybrid human/animal factor VIII is produced either by mixture of animal heavy chain subunits with human light chain subunits or by mixture of human heavy chain subunits with animal light chain subunits, thereby producing human light chain/animal heavy chain and human heavy chain/animal light chain hybrid molecules. These hybrid molecules are isolated by ion exchange chromatography.

Alternatively, one or more domains or partial domains of factor VIII are isolated and purified from human or animal plasma, and hybrid human/animal factor VIII is produced by mixture of domains or partial domains from one species with domains or partial domains of the second species. Hybrid molecules can be isolated by ion exchange chromatography.

Methods for preparing highly purified hybrid factor VIII are described having the steps of: (a) isolation of subunits of plasma-derived human factor VIII and subunits of plasma-derived animal factor VIII, followed by reconstitution of coagulant activity by mixture of human and animal subunits, followed by isolation of hybrid human/animal factor VIII by ion exchange chromatography; (b) isolation of domains or partial domains of plasma-derived human factor VIII and domains or partial domains of plasma-derived animal factor VIII, followed by reconstitution of coagulant activity by mixture of human and animal domains, followed by isolation of hybrid human/animal factor VIII by ion exchange chromatography; (c) construction of domains or partial domains of animal factor VIII by recombinant DNA technology, and recombinant: exchange of domains of animal and human factor VIII to produce hybrid human/animal factor VIII with coagulant activity; (d) creation of hybrid human/animal factor VIII by replacement of specific amino acid residues of the factor VIII of one species with the corresponding unique amino acid residues of the factor VIII of the other species; or (e) creation of a hybrid equivalent factor VIII molecule having human or animal amino acid sequence or both, in which specific amino acid residues of the factor VIII are replaced with amino acid residues having no known sequence identity to factor VIII by site-directed mutagenesis.

Some embodiments of hybrid or hybrid equivalent factor VIII have specific activity greater than that of human factor VIII and equal to or greater than that of porcine factor VIII. Some embodiments of hybrid or hybrid equivalent factor VIII have equal or less immunoreactivity with inhibitory antibodies to factor VIII and/or less immunogenicity in humans or animals, compared to human or porcine factor VIII.

Also provided are pharmaceutical compositions and methods for treating patients having factor VIII deficiency comprising administering the hybrid or hybrid equivalent factor VIII.

BRIEF DESCRIPTION OF THE DRAWINGS

FIG. 1A and 1B is an amino acid sequence alignment of human, mouse, and porcine factor VIII A2 domains, in which residue numbering begins at position 373 with respect to the full length sequence of human factor VIII (SEQ ID NO: 2).

DETAILED DESCRIPTION OF THE INVENTION

Definitions

Unless otherwise specified or indicated, as used herein, "hybrid factor VIII" or "hybrid protein" denotes any functional factor VIII protein molecule or fragment thereof comprising factor VIII amino acid sequence from human, porcine, and/or non-human, non-porcine mammalian species. Such combinations include, but are not limited to, any or all of the following hybrid factor VIII molecules or fragments thereof: (1) human/porcine; (2) human/non-human, non-porcine mammalian, such as human/mouse; (3) porcine/non-human, non-porcine mammalian, such as porcine/mouse; and (4) species-1/species-2, in which neither species is porcine or human, such as mouse/dog. Such combinations also include hybrid factor VIII equivalent molecules or fragments thereof, as further defined below, comprising factor VIII amino acid sequence of hybrid, human, porcine, or non-human, non-porcine mammalian origin in which amino acid sequence having no known sequence identity to factor VIII is substituted. Such hybrid combinations also include hybrid factor VIII molecules or fragments thereof comprising factor VIII amino acid sequence derived from more than two species, such as human/pig/mouse, or from two or more species in which amino acid sequence having no known sequence identity to factor VIII is substituted. Unless otherwise indicated, "hybrid factor VIII" includes fragments of the hybrid factor VIII, which can be used, as described below in one exemplary embodiment, as probes for research purposes or as diagnostic reagents.

As used herein, "mammalian factor VIII" includes factor VIII with amino acid sequence derived from any non-human mammal, unless otherwise specified. "Animal", as used herein, refers to pig and other non-human mammals.

A "fusion protein" or "fusion factor VIII or fragment thereof", as used herein, is the product of a hybrid gene in which the coding sequence for one protein is extensively altered, for example, by fusing part of it to the coding sequence for a second protein from a different gene to produce a hybrid gene that encodes the fusion protein. As used herein, a fusion protein is a subset of the hybrid VIII protein described in this application.

A "corresponding" nucleic acid or amino acid or sequence of either, as used herein, is one present at a site in a factor VIII or hybrid factor VIII molecule or fragment thereof that has the same structure and/or function as a site in the factor VIII molecule of another species, although the nucleic acid or amino acid number may not be identical. A sequence "corresponding to" another factor VIII sequence substantially corresponds to such sequence, and hybridizes to the sequence of the designated SEQ ID NO. under stringent conditions. A sequence "corresponding to" another factor VIII sequence also includes a sequence that results in the expression of a factor VIII or claimed procoagulant hybrid factor VIII or fragment thereof and would hybridize to the designated SEQ ID NO. but for the redundancy of the genetic code.

A "unique" amino acid residue or sequence, as used herein, refers to an amino acid sequence or residue in the factor VIII molecule of one species that is different from the homologous residue or sequence in the factor VIII molecule of another species.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Hybrid human/porcine factor VIII has coagulation activity in a human factor VIII assay. This activity, as well as that of other hybrid or hybrid equivalent factor VIII molecules or fragments thereof, may be less than, equal to, or greater than that of either plasma-derived or recombinant human factor VIII.

The human factor VIII cDNA nucleotide and predicted amino acid sequences are shown in SEQ ID NOs:1 and 2, respectively. Factor VIII is synthesized as an approximately 300 kDa single chain protein with internal sequence homology that defines the "domain" sequence NH$_2$-A1-A2-B-A3-C1-C2-COOH. In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO:2): A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

"Subunits" of human or animal factor VIII, as used herein, are the heavy and light chains of the protein. The heavy chain of factor VIII contains three domains, A1, A2, and B. The light chain of factor VIII also contains three domains, A3, C1, and C2.

The hybrid factor VIII or fragment thereof can be made (1) by substitution of isolated, plasma-derived animal subunits or human subunits (heavy or light chains) for corresponding human subunits or animal subunits; (2) by substitution of human domains or animal domains (A1, A2, A3, B, C1, and C2) for corresponding animal domains or human domains; (3) by substitution of parts of human domains or animal domains for parts of animal domains or human domains; (4) by substitution of at least one specific sequence including one or more unique human or animal amino acid(s) for the corresponding animal or human amino acid(s); or (5) by substitution of amino acid sequence that has no known sequence identity to factor VIII for at least one sequence including one or more specific amino acid residue(s) in human, animal, or hybrid factor VIII or fragments thereof. A "B-domainless" hybrid factor VIII, hybrid equivalent factor VIII, or fragment of either, as used herein, refers to any one of the hybrid factor VIII constructs described herein that lacks the B domain.

The terms "epitope", "antigenic site", and "antigenic determinant", as used herein, are used synonymously and are defined as a portion of the human, animal, hybrid, or hybrid equivalent factor VIII or fragment thereof that is specifically recognized by an antibody. It can consist of any number of amino acid residues, and it can be dependent upon the primary, secondary, or tertiary structure of the protein. In accordance with this disclosure, a hybrid factor VIII, hybrid factor VIII equivalent, or fragment of either that includes at least one epitope may be used as a reagent in the diagnostic assays described below. In some embodiments, the hybrid or hybrid equivalent factor VIII or fragment thereof is not cross-reactive or is less cross-reactive with all naturally occurring inhibitory factor VIII antibodies than human or porcine factor VIII.

The term "immunogenic site", as used herein, is defined as a region of the human or animal factor VIII, hybrid or hybrid equivalent factor VIII, or fragment thereof that specifically elicits the production of antibody to the factor VIII, hybrid, hybrid equivalent, or fragment in a human or animal, as measured by routine protocols, such as immunoassay, e.g. ELISA, or the Bethesda assay, described herein. It can consist of any number of amino acid residues, and it can be dependent upon the primary, secondary, or tertiary structure of the protein. In some embodiments, the hybrid or hybrid equivalent factor VIII or fragment thereof is nonimmunogenic or less immunogenic in an animal or human than human or porcine factor VIII.

As used herein, a "hybrid factor VIII equivalent molecule or fragment thereof" or "hybrid equivalent factor VIII or fragment thereof" is an active factor VIII or hybrid factor VIII molecule or fragment thereof comprising at least one sequence including one or more amino acid residues that have no known identity to human or animal factor VIII sequence substituted for at least one sequence including one or more specific amino acid residues in the human, animal, or hybrid factor VIII or fragment thereof. The sequence of one or more amino acid residues that have no known identity to human or animal factor VIII sequence is also referred to herein as "non-factor VIII amino acid sequence". In a preferred embodiment, the amino acid(s) having no known sequence identity to factor VIII sequence are alanine residues. In another preferred embodiment, the specific factor VIII sequence for which the amino acid(s) having no known sequence identity to factor VIII sequence are substituted includes an antigenic site that is immunoreactive with naturally occurring factor VIII inhibitory antibodies, such that the resulting hybrid factor VIII equivalent molecule or fragment thereof is less immunoreactive or not immunoreactive with factor VIII inhibitory antibodies. In yet another preferred embodiment, the specific hybrid factor VIII sequence for which the amino acid(s) having no known sequence identity to factor VIII sequence are substituted includes an immunogenic site that elicits the formation of factor VIII inhibitory antibodies in an animal or human, such that the resulting hybrid factor VIII equivalent molecule or fragment thereof is less immunogenic.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, however, the hybrid or hybrid equivalent factor VIII DNA or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the hybrid or hybrid equivalent factor VIII DNA or fragment thereof or protein expressed therefrom, that permits modification of known assays for detection of antibodies to human or animal factor VIII or to hybrid human/animal factor VIII. Such assays include, but are not limited to ELISAs, immunodiffusion assays, and immunoblots. Suitable methods for practicing any of these assays are known to those of skill in the art. As used herein, the hybrid or hybrid equivalent factor VIII or fragment thereof that includes at least one epitope of the protein can be used as the diagnostic reagent. Examples of other assays in which the hybrid or hybrid equivalent factor VIII or fragment thereof can be used include the Bethesda assay and anticoagulation assays.

General Description of Methods

U.S. Ser. No. 07/864,004 describes the discovery of hybrid human/porcine factor VIII molecules having coagulant activity, in which elements of the factor VIII molecule of human or pig are substituted for corresponding elements of the factor VIII molecule of the other species. U.S. Ser. No. 08/212,133 and PCT/US94/13200 describe procoagulant hybrid human/animal and hybrid equivalent factor VIII molecules, in which elements of the factor VIII molecule of one species are substituted for corresponding elements of the factor VIII molecule of the other species.

The present invention provides hybrid human/animal, animal/animal, and equivalent factor VIII molecules and fragments thereof, and the nucleic acid sequences encoding such hybrids, some of which have greater coagulant activity in a standard clotting assay when compared to highly-purified human factor VIII; and/or are less immunoreactive to inhibitory antibodies to human or porcine factor VIII than human or porcine factor VIII; and/or are less immunogenic in a human or animal than human or porcine factor VIII. These hybrid factor VIII molecules can be constructed as follows.

At least five types of active hybrid human/porcine or hybrid equivalent factor VIII molecules or fragments thereof, the nucleic acid sequences encoding these hybrid factor VIII molecules, and the methods for preparing them are disclosed herein: those obtained (1) by substituting a human or porcine subunit (i.e., heavy chain or light chain) for the corresponding porcine or human subunit; (2) by substituting one or more human or porcine domain(s) (i.e., A1, A2, A3, B, C1, and C2) for the corresponding porcine or human domain(s); (3) by substituting a continuous part of one or more human or porcine domain(s) for the corresponding part of one or more porcine or human domain(s); (4) by substituting at least one specific sequence including one or more unique amino acid residue(s) in human or porcine factor VIII for the corresponding porcine or human sequence; and (5) by substituting at least one sequence including one or more amino acid residue(s) having no known sequence identity to factor VIII ("non-factor VIII amino acid sequence") for at least one specific sequence of one or more amino acids in human, porcine, or hybrid human/porcine factor VIII.

At least five types of active hybrid human/non-human, non-porcine mammalian or hybrid equivalent factor VIII molecules or fragments thereof, and the nucleic acid sequences encoding them, can also be prepared by the same methods: those obtained (1) by substituting a human or non-human, non-porcine mammalian subunit (i.e., heavy chain or light chain) for the corresponding non-human, non-porcine mammalian or human subunit; (2) by substituting one or more human or non-human, non-porcine mammalian domain(s) (i.e., A1, A2, A3, B, C1, and C2) for the corresponding non-human, non-porcine mammalian or human domain(s); (3) by substituting a continuous part of one or more human or non-human, non-porcine mammalian domain(s) for the corresponding part of one or more non-human, non-porcine mammalian or human domain(s); (4) by substituting at least one specific sequence including one or more unique amino acid residue(s) in human or non-human, non-porcine mammalian factor VIII for the corresponding non-human, non-porcine mammalian or human sequence; and (5) by substituting at least one sequence including one or more amino acid residue(s) having no known sequence identity to factor VIII ("non-factor VIII amino acid sequence") for at least one specific sequence of one or more amino acids in human, non-human, non-porcine mammalian, or hybrid human/non-human, non-porcine mammalian factor VIII.

Further, one skilled in the art will readily recognize that the same methods can be used to prepare at least five types of active hybrid factor VIII molecules or fragments thereof, corresponding to types (1)–(5) in the previous two paragraphs, comprising factor VIII amino acid sequence from two or more non-human mammals, such as porcine/mouse, and further comprising non-factor VIII amino acid sequence.

Hybrid human/animal, animal/animal, and equivalent factor VIII proteins or fragments thereof listed above under groups (1)–(3) are made by isolation of subunits, domains, or continuous parts of domains of plasma-derived factor VIII, followed by reconstitution and purification. Hybrid human/animal, animal/animal, and equivalent factor VIII proteins or fragments thereof described under groups (3)–(5) above are made by recombinant DNA methods. The hybrid molecule may contain a greater or lesser percentage of human than animal sequence, depending on the origin of the various regions, as described in more detail below.

Since current information indicates that the B domain has no inhibitory epitope and has no known effect on factor VIII function, in some embodiments the B domain is deleted in the active hybrid or hybrid equivalent factor VIII molecules or fragments thereof ("B(−) factor VIII") prepared by any of the methods described herein.

It is shown in Example 4 that hybrid human/porcine factor VIII comprising porcine heavy chain and human light chain and corresponding to the first type of hybrid listed above has greater specific coagulant activity in a standard clotting assay compared to human factor VIII. The hybrid human/animal or equivalent factor VIII with coagulant activity, whether the activity is higher, equal to, or lower than that of human factor VIII, can be useful in treating patients with inhibitors, since these inhibitors can react less with hybrid human/animal or equivalent factor VIII than with either human or porcine factor VIII.

Preparation of hybrid factor VIII molecules from isolated human and animal factor VIII subunits by reconstitution The present invention provides hybrid human/animal factor VIII molecules or fragments thereof, with subunit substitutions, the nucleic acid sequences encoding these hybrids, methods for preparing and isolating them, and methods for characterizing their procoagulant activity. One method, modified from procedures reported by Fay, P. J., et al., 265 *J. Biol. Chem.* 6197 (1990); and Lollar, J. S., et al., 263 *J. Biol. Chem.* 10451 (1988), involves the isolation of subunits (heavy and light chains) of human and animal factor VIII, followed by recombination of human heavy chain and animal light chain or by recombination of human light chain and animal heavy chain.

Isolation of both human and animal individual subunits involves dissociation of the light chain/heavy chain dimer. This is accomplished, for example, by chelation of calcium with ethylenediaminetetraacetic acid (EDTA), followed by monoS™ HPLC (Pharmacia-LKB, Piscataway, N.J.). Hybrid human/animal factor VIII molecules are reconstituted from isolated subunits in the presence of calcium. Hybrid human light chain/animal heavy chain or animal light chain/human heavy chain factor VIII is isolated from unreacted heavy chains by monoS™ HPLC by procedures for the isolation of porcine factor VIII, such as described by Lollar, J. S., et al., 71 *Blood* 137–143 (1988).

These methods, used in one embodiment to prepare active hybrid human/porcine factor VIII, described in detail in the examples below, result in hybrid human light chain/porcine heavy chain molecules with greater than six times the procoagulant activity of human factor VIII.

Other hybrid human/non-human, non-porcine mammalian factor VIII molecules can be prepared, isolated, and characterized for activity by the same methods. One skilled in the art will readily recognize that these methods can also be used to prepare, isolate, and characterize for activity hybrid animal/animal factor VIII, such as porcine/mouse, comprising the light or heavy chain or one species is combined with the heavy or light chain of the other species.

Preparation of hybrid factor VIII molecules from isolated human and animal factor VIII domains by reconstitution The present invention provides hybrid human/animal factor VIII molecules or fragments thereof with domain substitutions, the nucleic acid sequences encoding them, methods for preparing and isolating them, and methods for characterizing their procoagulant activity. One method involves the isolation of one or more domains of human and one or more domains of animal factor VIII, followed by recombination of human and animal domains to form hybrid human/animal factor VIII with coagulant activity, as described by Lollar, P., et al., 267(33) *J. Biol. Chem.* 23652–23657 (Nov. 25, 1992), for hybrid human/porcine factor VIII.

Specifically provided is a hybrid human/porcine factor VIII with substitution of the porcine A2 domain for the human A2 domain, which embodiment illustrates a method by which domain-substituted hybrid human/non-human, non-porcine mammalian factor VIII can be constructed. Plasma-derived non-human, non-porcine mammalian and human A1/A3-C1-C2 dimers are isolated by dissociation of the A2 domain from factor VIIIa. This is accomplished, for example, in the presence of NaOH, after which the mixture is diluted and the dimer is eluted using monos HPLC (Pharmacia-LKB, Piscataway, N.J.). The A2 domain is isolated from factor VIIIa as a minor component in the monoS™ HPLC. Hybrid human/animal factor VIII molecules are reconstituted by mixing equal volumes of the A2 domain of one species and the A1/A3-C1-C2 dimer of the other species.

Hybrid human/animal factor VIII or fragments thereof with one or more domain substitutions is isolated from the mixture of unreacted dimers and A2 by monoS™ HPLC by procedures for the isolation of porcine factor VIII, as described by Lollar, J. S., et al., 71 *Blood* 137–143 (1988). Routine methods can also be used to prepare and isolate the A1, A3, C1, C2, and B domains of the factor VIII of one species, any one or more of which can be substituted for the corresponding domain in the factor VIII of the other species. One skilled in the art will readily recognize that these methods can also be used to prepare, isolate, and characterize for activity domain-substituted hybrid animal/animal factor VIII, such as porcine/mouse.

These methods, described in detail in the examples below, result in hybrid factor VIII molecules with procoagulant activity.

Preparation of hybrid factor VIII molecules by recombinant engineering of the sequences encoding human, animal, and hybrid factor VIII subunits, domains, or parts of domains Substitution of subunits, domains, continuous parts of domains:

The present invention provides active, recombinant hybrid human/animal and hybrid equivalent factor VIII molecules and fragments thereof with subunit, domain, and amino acid sequence substitutions, the nucleic acid sequences encoding these hybrids, methods for preparing and isolating them, and methods for characterizing their coagulant, immunoreactive, and immunogenic properties.

The human factor VIII gene was isolated and expressed in mammalian cells, as reported by Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech); WO 87/04187; WO 88/08035; WO 88/03558; U.S. Pat. No. 4,757,006, and the amino acid sequence was deduced from cDNA. U.S. Pat. No. 4,965,199 to Capon et al. discloses a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part or all of the B domain (U.S. Pat. No. 4,868,112), and replacement of the human factor VIII B domain with the human factor V B domain has been attempted (U.S. Pat. No.

5,004,803). The cDNA sequence encoding human factor VIII and predicted amino acid sequence are shown in SEQ ID NOs:1 and 2, respectively.

Porcine factor VIII has been isolated and purified from plasma (Fass, D. N., et al., 59 *Blood* 594 (1982)). Partial amino acid sequence of porcine factor VIII corresponding to portions of the N-terminal light chain sequence having homology to ceruloplasmin and coagulation factor V and largely incorrectly located were described by Church et al., 81 *Proc. Natl. Acad. Sci. USA* 6934 (1984). Toole, J. J., et al., 312 *Nature* 342–347 (1984) described the partial sequencing of the N-terminal end of four amino acid fragments of porcine factor VIII but did not characterize the fragments as to their positions in the factor VIII molecule. The amino acid sequence of the B and part of the A2 domains of porcine factor VIII were reported by Toole, J. J., et al., 83 *Proc. Natl. Acad. Sci. U.S.A.* 5939–5942 (1986). The cDNA sequence encoding the complete A2 domain of porcine factor VIII and predicted amino acid sequence and hybrid human/porcine factor VIII having substitutions of all domains, all subunits, and specific amino acid sequences were disclosed in U.S. Ser. No. 07/864,004 entitled "Hybrid Human/Porcine Factor VIII" filed Apr. 7, 1992 by John S. Lollar and Marschall S. Runge, which issued as U.S. Pat. No. 5,364,771 on Nov. 15, 1994, and in WO 93/20093. The cDNA sequence encoding the A2 domain of porcine factor VIII having sequence identity to residues 373–740 in mature human factor VIII, as shown in SEQ ID NO:1, and the predicted amino acid sequence are shown in SEQ ID NOs:3 and 4, respectively. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503.

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII ("factor VIIIa") have three subunits due to cleavage of the heavy chain between the A1 and A2 domains. This structure is designated A1/A2/A3-C1-C2. Human factor VIIIa is not stable under the conditions that stabilize porcine factor VIIIa, presumably because of the weaker association of the A2 subunit of human factor VIIIa. Dissociation of the A2 subunit of human and porcine factor VIIIa is associated with loss of activity in the factor VIIIa molecule.

Using as probes the known sequence of parts of the porcine factor VIII molecule, the domains of the porcine factor VIII molecule that have not been sequenced to date can be sequenced by standard, established cloning techniques, such as those described in Weis, J. H., "Construction of recombinant DNA libraries," in *Current Protocols in Molecular Biology*, F. M. Ausubel et al., eds. (1991); and Sambrook, J., et al., *Molecular Cloning, A Laboratory Manual*, so that full length hybrids can be constructed.

Specifically provided as an exemplary and a preferred embodiment is active recombinant hybrid human/porcine factor VIII having substituted A2 domain, the nucleic acid sequence encoding it, and the methods for preparing, isolating, and characterizing its activity. The methods by which this hybrid construct is prepared can also be used to prepare active recombinant hybrid human/porcine factor VIII or fragments thereof having substitution of subunits, continuous parts of domains, or domains other than A2. One skilled in the art will recognize that these methods also demonstrate how other recombinant hybrid human/non-human, non-porcine mammalian or animal/animal hybrid factor VIII molecules or fragments thereof can be prepared in which subunits, domains, or continuous parts of domains are substituted.

Recombinant hybrid human/porcine factor VIII is prepared starting with human cDNA (Biogen, Inc.) encoding the factor VIII sequence. In a preferred embodiment, the factor VIII encoded by this cDNA includes domains A1-A2-A3-C1-C2, lacking the entire B domain, and corresponds to amino acid residues 1–740 and 1649–2332 of single chain human factor VIII (see SEQ ID NO:2), according to the numbering system of Wood et al., 312 *Nature* 330–337 (1984).

Individual subunits, domains, or continuous parts of domains of porcine or human factor VIII cDNA can be cloned and substituted for the corresponding human or porcine subunits, domains, or parts of domains by established mutagenesis techniques. For example, Lubin, I. M., et al., 269(12) *J. Biol Chem.* 8639–8641 (March 1994) describes techniques for substituting the porcine A2 domain for the human domain using convenient restriction sites. Other methods for substituting any arbitrary region of the factor VIII cDNA of one species for the factor VIII cDNA of another species include splicing by overlap extension ("SOE"), as described by Horton, R. M., et al., 217 *Meth. Enzymol.* 270–279 (1993).

The hybrid factor VIII cDNA encoding subunits, domains, or parts of domains or the entire hybrid cDNA molecules are cloned into expression vectors for ultimate expression of active hybrid human/porcine factor VIII protein molecules in cultured cells by established techniques, as described by Selden, R. F., "Introduction of DNA into mammalian cells," in *Current Protocols in Molecular Biology*, F. M. Ausubel et al., eds (1991).

In a preferred embodiment, a hybrid human/porcine cDNA encoding factor VIII, in which the porcine sequence encodes a domain or part domain, such the A2 domain or part domain, is inserted in a mammalian expression vector, such as ReNeo, to form a hybrid factor VIII construct. Preliminary characterization of the hybrid factor VIII is accomplished by insertion of the hybrid cDNA into the ReNeo mammalian expression vector and transient expression of the hybrid protein in COS-7 cells. A determination of whether active hybrid protein is expressed can then be made. The expression vector construct is used further to stably transfect cells in culture, such as baby hamster kidney cells, using methods that are routine in the art, such as liposome-mediated transfection (Lipofectin™, Life Technologies, Inc.). Expression of recombinant hybrid factor VIII protein can be confirmed, for example, by sequencing, Northern and Western blotting, or polymerase chain reaction (PCR). Hybrid factor VIII protein in the culture media in which the transfected cells stably expressing the protein are maintained can be precipitated, pelleted, washed, and resuspended in an appropriate buffer, and the recombinant hybrid factor VIII protein purified by standard techniques, including immunoaffinity chromatography using, for example, monoclonal anti-A2-Sepharose™.

In a further embodiment, the hybrid factor VIII comprising subunit, domain, or amino acid sequence substitutions is expressed as a fusion protein from a recombinant molecule in which sequence encoding a protein or peptide that enhances, for example, stability, secretion, detection, isolation, or the like is inserted in place adjacent to the factor VIII encoding sequence. Established protocols for use of homologous or heterologous species expression control sequences including, for example, promoters, operators, and regulators, in the preparation of fusion proteins are known and routinely used in the art. See *Current Protocols in Molecular Biology* (Ausubel, F. M., et al., eds), Wiley Interscience, New York.

The purified hybrid factor VIII or fragment thereof can be assayed for immunoreactivity and coagulation activity by standard assays including, for example, the plasma-free factor VIII assay, the one-stage clotting assay, and the enzyme-linked immunosorbent assay using purified recombinant human factor VIII as a standard.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). Other vectors and expression systems, including bacterial, yeast, and insect cell systems, can be used but are not preferred due to differences in, or lack of, glycosylation.

Recombinant hybrid factor VIII protein can be expressed in a variety of cells commonly used for culture and recombinant mammalian protein expression. A preferred cell line, available from the American Type Culture Collection, Rockville, Md., is baby hamster kidney cells, which are cultured using routine procedure and media.

The same methods employed for preparing hybrid human/porcine factor VIII having subunit, domain, or amino acid sequence substitution can be used to prepare other recombinant hybrid factor VIII protein and fragments thereof and the nucleic acid sequences encoding these hybrids, such as human/non-human, non-porcine mammalian or animal/animal. Starting with primers from the known human DNA sequence, the murine and part of the porcine factor VIII cDNA have been cloned. Factor VIII sequences of other species for use in preparing a hybrid human/animal or animal/animal factor VIII molecule can be obtained using the known human and porcine DNA sequences as a starting point. Other techniques that can be employed include PCR amplification methods with animal tissue DNA, and use of a cDNA library from the animal to clone out the factor VIII sequence.

As an exemplary embodiment, hybrid human/mouse factor VIII protein can be made as follows. DNA clones corresponding to the mouse homolog of the human factor VIII gene have been isolated and sequenced and the amino acid sequence of mouse factor VIII protein predicted, as described in Elder, G., et al., 16(2) *Genomics* 374–379 (May 1993), which also includes a comparison of the predicted amino acid sequences of mouse, human, and part of porcine factor VIII molecules. The mouse factor VIII cDNA sequence and predicted amino acid sequence are shown in SEQ ID NO:5 and SEQ ID NO:8, respectively. In a preferred embodiment, the RNA amplification with transcript sequencing (RAWTS) methods described in Sarkar, G., and S. S. Sommer, 244 *Science* 331–334 (1989), can be used. Briefly, the steps are (1) cDNA synthesis with oligo(dT) or an mRNA-specific oligonucleotide primer; (2) polymerase chain reaction (PCR) in which one or both oligonucleotides contains a phage promoter attached to a sequence complementary to the region to be amplified; (3) transcription with a phage promoter; and (4) reverse transcriptase-mediated dideoxy sequencing of the transcript, which is primed with a nested (internal) oligonucleotide. In addition to revealing sequence information, this method can generate an in vitro translation product by incorporating a translation initiation signal into the appropriate PCR primer; and can be used to obtain novel mRNA sequence information from other species.

Substitution of amino acid(s):

The present invention provides active recombinant hybrid human/animal and animal/animal factor VIII molecules or fragments thereof comprising at least one sequence including one or more unique amino acids of one species substituted for the corresponding amino acid sequence of the other species or fragments thereof, nucleic acid sequences encoding these hybrids, methods for preparing and isolating them, and methods for characterizing their coagulant, immunogenic, and immunoreactive properties.

The A2 domain is necessary for the procoagulant activity of the factor VIII molecule. Studies show that porcine factor VIII has six-fold greater procoagulant activity than human factor VIII (Lollar, P., and E. T. Parker 266 *J. Biol. Chem.* 12481–12486 (1991)), and that the difference in coagulant activity between human and porcine factor VIII appears to be based on a difference in amino acid sequence between one or more residues in the human and porcine A2 domains (Lollar, P., et al., 267 *J. Biol. Chem.* 23652–23657 (1992)). Further, the A2 and C2 domains and possibly a third light chain region in the human factor VIII molecule are thought to harbor the epitopes to which most, if not all, inhibitory antibodies react, according to Hoyer, L. W., and D. Scandella, 31 *Semin. Hematol.* 1–5 (1994).

Recombinant hybrid human/animal, animal/animal, or equivalent factor VIII molecules or fragments thereof can be made by substitution of at least one specific sequence including one or more unique amino acids from the A2, C2, and/or other domains of the factor VIII of one species for the corresponding sequence of the other species, wherein the amino acid sequences differ, as illustrated in more detail below, between the molecules of the two species. In an exemplary preferred embodiment described herein, the present invention provides active recombinant hybrid human/porcine factor VIII comprising porcine amino acid sequence substituted for corresponding human amino acid sequence that includes an epitope, wherein the hybrid factor VIII has decreased or no immunoreactivity with inhibitory antibodies to factor VIII. In a further embodiment, active recombinant hybrid factor VIII molecules can also be made comprising amino acid sequence from more than one species substituted for the corresponding sequence in a third species. Recombinant hybrid equivalent molecules can also be made, comprising human, animal, or hybrid factor VIII including at least one sequence including one or more amino acids that have no known sequence identity to factor VIII, as further described below.

Any hybrid factor VIII construct having specific amino acid substitution as described can be assayed by standard procedures for coagulant activity and for reactivity with inhibitory antibodies to factor VIII for identification of hybrid factor VIII molecules with enhanced coagulant activity and/or decreased antibody immunoreactivity. Hybrid molecules may also be identified that have reduced coagulant activity compared to human or porcine factor VIII but also have decreased antibody reactivity. One skilled in the art will recognize that hybrid factor VIII molecules or fragments thereof having less, equal, or greater coagulant activity, compared to human or porcine factor VIII, is useful for treating patients who have a factor VIII deficiency. The methods described herein to prepare active recombinant hybrid human/porcine factor VIII with substitution of specific amino acids can be used to prepare active recombinant hybrid human/non-human, non-porcine mammalian factor VIII protein, hybrid animal-1/animal-2 factor VIII, and hybrid equivalent factor VIII or fragments thereof.

Hybrid factor VIII molecules with altered coagulant activity.

The present invention provides procoagulant recombinant hybrid human/animal, animal/animal, or equivalent factor VIII molecules or fragments thereof comprising at least one specific sequence including one or more unique amino acids having procoagulant activity in the factor VIII of one species substituted for the corresponding amino acid sequence of the factor VIII of the other species, using established site-directed mutagenesis techniques as described herein. The specific sequences to be used in the substitution are selected and the hybrid constructs are prepared and assayed for coagulant activity, as follows. Specifically provided as a preferred and exemplary embodiment is a hybrid human/porcine factor VIII comprising amino acid substitutions in the A2 domain. It is understood that one skilled in the art can use these methods to prepare other hybrid human/animal, animal/animal, and equivalent factor VIII molecules or fragments thereof having altered coagulant activity, preferably increased coagulant activity compared to human factor VIII.

The basis for the greater coagulant activity in porcine factor VIII appears to be the more rapid spontaneous dissociation of the A2 subunit of human factor VIIIa than porcine factor VIIIa, which leads to loss of activity, according to Lollar, P., and C. G. Parker, 265 *J. Biol. Chem.* 1688–1692 (1990); Lollar, P., et al. 267 *J. Biol. Chem.* 23652–23657 (1992); Fay, P. J., and T. M. Smudzin, 267 *J. Biol.Chem.* 13246–13250 (1992).

A comparison of the alignment of the amino acid sequences of the human and porcine factor VIII A2 domains (residue numbering starts at position 373 with respect to the full length amino acid sequence of human factor VIII, SEQ ID NO:2) is shown in FIG. 1A–1B. For preparation of a hybrid human/porcine factor VIII molecule with altered coagulant activity, the initial target candidates for mutagenesis, which were revealed upon comparison of the human and porcine A2 amino acid sequences (SEQ ID NOs:2 and 4, respectively) within the human A2 domain, are shown in Table I.

TABLE I

HUMAN AMINO ACID SEQUENCE TARGET CANDIDATES FOR MUTAGENESIS (SEQ ID NO: 2)

| Sequence | Residues | Mismatches | Charge Changes |
|---|---|---|---|
| 398–403 | 6 | 4 | 1 |
| 434–444 | 10 | 4 | 3 |
| 484–496 | 13 | 7 | 3 |
| 598–603 | 6 | 4 | 2 |
| 536–541 | 6 | 4 | 0 |
| 713–722 | 10 | 6 | 2 |
| 727–737 | 11 | 6 | 2 |

Table I and the bold letters of FIG. 1A–1B illustrate seven sequences in the human and pig A2 domain amino acid sequences (SEQ ID NOs:2 and 4, respectively) that constitute only 17 percent of the A2 domain but include 70 percent of the sequence differences between human and porcine A2 domains.

A recombinant hybrid human/porcine construct is described in which amino acids Ser373-Glu604 in the A2 domain (Ser373-Arg740) of human factor VIII have been replaced with the homologous porcine sequence. This construct does not react with A2 inhibitors and has the same coagulant activity as human B(−) factor VIII. A plasma-derived hybrid molecule is described that comprises a complete porcine A2 domain substitution in the human factor VIII that has increased coagulant activity compared to human factor VIII. Comparison of these constructs indicates that a region between residues Asp605 and Arg740 is responsible for the difference in activity between human and porcine factor VIII. This region can be defined more specifically by systematically making recombinant hybrid human/porcine factor VIII molecules with porcine substitutions in the region between Asp605 and Arg740 by using established site-directed mutagenesis techniques, for example, the "splicing by overlap extension" (SOE) method that has been used extensively to make hybrid factor VIII molecules containing porcine substitutions in the $NH_2$-terminal region of A2. These molecules can be expressed in COS-7 cells and baby hamster kidney cells as described above. They can be purified to homogeneity using methods known in the art, such as heparin-Sepharose™ and immunoaffinity chromatography. Protein concentration can be estimated by absorption of ultraviolet light at $A_{280}$, and the specific activity of the constructs can be determined by dividing coagulant activity (measured in units per ml by single stage clotting assay) by $A_{280}$. Human factor VIII has a specific activity of approximately 3000–4000 U/$A_{280}$, whereas porcine factor VIII has a specific activity of approximately 20,000 U/$A_{280}$. In a preferred embodiment, the procoagulant recombinant hybrid human/porcine factor VIII has a specific activity of 20,000 U/$A_{280}$ and contains a minimal amount of porcine substitution in the A2 domain.

As described herein, site-directed mutagenesis techniques are used to identify hybrid protein with coagulant activity that can be enhanced, equal to, or reduced, compared to human factor VIII, but preferably is enhanced. In the hybrid human/porcine embodiment, specific human sequences are replaced with porcine sequences, preferably using the splicing by overlap extension method (SOE), as described by Ho, S. N., et al., 77 *Gene* 51–59 (1994), and in Examples 7 and 8. Oligonucleotide-directed mutagenesis can also be used, as was done to loop out the amino acid sequence for part of the human A2 domain (see Example 7). As functional analysis of the hybrids reveals coagulant activity, the sequence can be further dissected and mapped for procoagulant sequence by standard point mutation analysis techniques.

The present invention contemplates that hybrid factor VIII cDNA and protein can be characterized by methods that are established and routine, such as DNA sequencing, coagulant activity assays, mass by ELISA and by UV absorbance at 280 nm of purified hybrid factor VIII, specific coagulant activity (U/mg), SDS-PAGE of purified hybrid factor VIII, and the like. Other known methods of testing for clinical effectiveness may be required, such as amino acid, carbohydrate, sulfate, or metal ion analysis.

A recombinant hybrid factor VIII having superior coagulant activity, compared to human factor VIII, may be less expensive to make than plasma-derived factor VIII and may decrease the amount of factor VIII required for effective treatment of factor VIII deficiency.

Hybrid factor VIII molecules with reduced immunoreactivity.

Epitopes that are immunoreactive with antibodies that inhibit the coagulant activity of factor VIII ("inhibitors" or "inhibitory antibodies") have been characterized based on known structure-function relationships in factor VIII. Presumably, inhibitors could act by disrupting any of the macromolecular interactions associated with the domain structure of factor VIII or its associations with von Willebrand factor, thrombin, factor Xa, factor IXa, or factor X. However, over 90 percent of inhibitory antibodies to human factor VIII act by binding to epitopes located in the 40 kDa A2 domain or 20 kDa C2 domain of factor VIII, disrupting specific functions associated with these domains, as described by Fulcher et al., 82 Proc. Natl. Acad. Sci. USA 7728–7732 (1985), and Scandella et al., 85 Proc. Natl. Acad. Sci. USA 6152–6156 (1988). In addition to the A2 and C2 epitopes, there may be a third epitope in the A3 or C1 domain of the light chain of factor VIII, according to Scandella et al., 82 Blood 1767–1775 (1993). The significance of this putative third epitope is unknown, but it appears to account for a minor fraction of the epitope reactivity in factor VIII.

Anti-A2 antibodies block factor X activation, as shown by Lollar et al., 93 J. Clin. Invest. 2497–2504 (1994). Previous mapping studies by deletion mutagenesis described by Ware et al., 3 Blood Coagul. Fibrinolysis 703–716 (1992), located the A2 epitope to within a 20 kDa region at the $NH_2$-terminal end of the 40 kDa A2 domain. Competition immunoradiometric assays have indicated that A2 inhibitors recognize either a common epitope or narrowly clustered epitopes, as described by Scandella et al., 67 Thromb. Haemostas. 665–671 (1992), and as demonstrated in Example 8.

The present invention provides active recombinant hybrid and hybrid equivalent factor VIII molecules or fragments thereof, the nucleic acid sequences encoding these hybrids, methods of preparing and isolating them, and methods for characterizing them. These hybrids comprise human/animal, animal/animal, or equivalent hybrid factor VIII molecules, further comprising at least one specific amino acid sequence including one or more unique amino acids of the factor VIII of one species substituted for the corresponding amino acid sequence of the factor VIII of the other species; or comprises at least one sequence including one or more amino acids having no known sequence identity to factor VIII substituted for specific amino acid sequence in human, animal, or hybrid factor VIII. The resulting hybrid factor VIII has reduced or no immunoreactivity to factor VIII inhibitory antibodies, compared to human or porcine factor VIII.

Using the approach described in the previous section for substitution of amino acids in the factor VIII molecule, mutational analysis is employed to select corresponding factor VIII amino acid sequence of one species, preferably porcine, which is substituted for at least one sequence including one or more amino acids in the factor VIII of another species, preferably human, or for amino acid sequence of a hybrid equivalent factor VIII molecule, that includes one or more critical region(s) in the A2, C2, or any other domain to which inhibitory antibodies are directed. The methods are described in more detail below. The resulting procoagulant recombinant hybrid construct has reduced or no immunoreactivity to inhibitory antibodies, compared in human factor VIII, using standard assays. Through systematic substitution of increasingly smaller amino acid sequences followed by assay of the hybrid construct for immunoreactivity, as described below, the epitope in any domain of a factor VIII molecule is mapped, substituted by amino acid sequence having less or no immunoreactivity, and a hybrid factor VIII is prepared.

It is understood that one skilled in the art can use this approach combining epitope mapping, construction of hybrid factor VIII molecules, and mutational analysis of the constructs to identify and replace at least one sequence including one or more amino acids comprising an epitope in the A2, C2, and/or other domains to which inhibitory antibodies are directed and to construct procoagulant recombinant hybrid human/animal, animal/animal, or equivalent factor VIII or fragments thereof having decreased or no immunoreactivity compared to human, or porcine factor VIII. This approach is used, as described in Example 8, to prepare a recombinant procoagulant hybrid human/porcine factor VIII having porcine amino acid substitutions in the human A2 domain and no antigenicity to anti-factor VIII antibodies as an exemplary embodiment.

Usually, porcine factor VIII has limited or no reaction with inhibitory antibodies to human factor VIII. The recombinant hybrid human/porcine factor VIII molecules having decreased or no reactivity with inhibitory antibodies based on amino acid substitution in the A2 domain are prepared, as an example of how hybrid factor VIII can be prepared using the factor VIII of other species and substitutions in domains other than the A2, as follows. The porcine A2 domain is cloned by standard cloning techniques, such as those described above and in Examples 6, 7, and 8, and then cut and spliced within the A2 domain using routine procedures, such as using restriction sites to cut the cDNA or splicing by overlap extension (SOE). The resulting porcine amino acid sequence is substituted into the human A2 domain to form a hybrid factor VIII construct, which is inserted into a mammalian expression vector, preferably ReNeo, stably transfected into cultured cells, preferably baby hamster kidney cells, and expressed, as described above. The hybrid factor VIII is assayed for immunoreactivity, for example with anti-A2 antibodies by the routine Bethesda assay or by plasma-free chromogenic substrate assay. The Bethesda unit (BU) is the standard method for measuring inhibitor titers. If the Bethesda titer is not measurable (<0.7 BU/mg IgG) in the hybrid, then a human A2 epitope was eliminated in the region of substituted corresponding porcine sequence. The epitope is progressively narrowed, and the specific A2 epitope can thus be determined to produce a hybrid human/porcine molecule with as little porcine sequence as possible. As described herein, a 25-residue sequence corresponding to amino acids Arg484–Ile508 that is critical for inhibitory immunoreactivity has been identified and substituted in the human A2 domain. Within this sequence are only nine differences between human and porcine factor VIII. This region can be further analyzed and substituted.

Hybrid human/porcine factor VIII molecules having decreased or no reactivity with inhibitory antibodies based on substitution of amino acid sequence in the C1, C2, or other domain, with or without substitution in the A2 domain, can also be prepared. The C2 epitope, for example, can be mapped using the homolog scanning approach combined with site-directed mutagenesis. More specifically, the procedures can be the same or similar to those described herein for amino acid substitution in the A2 domain, including cloning the porcine C2 or other domain, for example by using RT-PCR or by probing a porcine liver CDNA library with human C2 or other domain DNA; restriction site techniques and/or successive SOE to map and simultaneously replace epitopes in the C2 or other domain; substitution for the human C2 or other domain in B(−) factor VIII; insertion into an expression vector, such as pBluescript; expression in cultured cells; and routine assay for immunoreactivity. For the assays, the reactivity of C2 hybrid factor VIII with a C2-specific inhibitor, MR (Scandella, D., et al., Thromb. Haemostasis 67:665–671 (1992) and Lubin et al. (1994)), and/or other C2 specific antibodies prepared by affinity chromatography can be performed.

The C2 domain consists of amino acid residues 2173–2332 (SEQ ID NO:2). Within this 154 amino acid region, inhibitor activity appears to be directed to a 65 amino acid region between residues 2248 and 2312, according to Shima, M., et al., 69 *Thromb. Haemostas.* 240–246 (1993). If the C2 sequence of human and porcine factor VIII is approximately 85 percent identical in this region, as it is elsewhere in the functionally active regions of factor VIII, there will be approximately ten differences between human and porcine factor VIII C2 amino acid sequence, which can be used as initial targets to construct hybrids with substituted C2 sequence.

It is likely that clinically significant factor VIII epitopes are confined to the A2 and C2 domains. However, if antibodies to other regions (A1, A3, B, or C1 domains) of factor VIII are identified, the epitopes can be mapped and eliminated by using the approach described herein for the nonantigenic hybrid human/porcine factor VIII molecules.

More specifically, mapping of the putative second light chain epitope and/or any other epitope in any other animal or human factor VIII domain can also be accomplished. Initially, determination of the presence of a third inhibitor epitope in the A3 or C1 domains can be made as follows. Using human ("H") and porcine ("p") factor VIII amino acid sequences as a model, $A1_p$-$A2_p$-$A3_p$-$C1_H$-$C2^P$ and $A1_p$-$A2_p$-$A3_H$-$C1_p$-$C2_p$ B-domainless hybrids will be constructed. Inhibitor IgG from approximately 20 patient plasmas (from Dr. Dorothea Scandella, American Red Cross) who have low or undetectable titers against porcine factor VIII will be tested against the hybrids. If the third epitope is in the A3 domain, inhibitory IgG is expected to react with $A1_p$-$A2_p$-$A3_H$-$C1_p$-$C2_p$ but not $A1_p$-$A2_p$-$A3_p$-$C1_H$-$C2_p$. Conversely, if the third epitope is in the C1 domain, then inhibitory IgG is expected to react with $A1_p$-$A2_p$-$A3_p$-$C1_H$-$C2_p$ but not $A1_p$-$A2_p$-$A3_H$-$C1_p$-$C2_p$. If a third epitope is identified it will be characterized by the procedures described herein for the A2 and C2 epitopes.

For example, antibodies specific for the C1 or A3 domain epitope can be isolated from total patient IgG by affinity chromatography using the $A1_p$-$A2_p$-$A3_H$-$C1_p$-$C2_p$ and $A1_p$-$A2_p$-$A3_p$-$C1H$-$C2_p$ hybrids, and by elimination of C2 specific antibodies by passage over recombinant factor VIII C2-Sepharose™. The putative third epitope will be identified by SOE constructs in which, in a preferred embodiment, portions of the human factor VIII A3 or C1 domain are systematically replaced with porcine sequence.

Hybrid factor VIII molecules with reduced immunogenicity.

A molecule is immunogenic when it can induce the production of antibodies in human or animal. The present invention provides a procoagulant recombinant hybrid human/animal or animal/animal factor VIII molecule, hybrid factor VIII equivalent molecule, or fragment of either that is less immunogenic than wild-type human porcine factor VIII in human or animal, comprising at least one specific amino acid sequence including one or more unique amino acids of the factor VIII of one species substituted for the corresponding amino acid sequence that has immunogenic activity of the factor VIII of the other species; or at least one amino acid sequence including one or more amino acids having no known identity to factor VIII substituted for amino acid sequence of the human, animal, or hybrid factor. This hybrid can be used to lower the incidence of inhibitor development in an animal or human and to treat factor VIII deficiency, and would be preferred in treating previously untreated patients with hemophilia. In a preferred embodiment, the hybrid factor VIII comprises human factor VIII amino acid sequence, further comprising one or more alanine residues substituted for human amino acid sequence having immunogenic activity, resulting in a procoagulant recombinant hybrid equivalent molecule or fragment thereof having reduced or no immunogenicity in human or animal.

The process described herein of epitope mapping and mutational analysis combined with substitution of non-antigenic amino acid sequence in a factor VIII molecule, using hybrid human/porcine factor VIII, produces hybrid molecules with low antigenicity. Using this model and the associated methods, any of the hybrid constructs described herein can be altered by site-directed mutagenesis techniques to remove as much of any functional epitope as possible to minimize the ability of the immune system to recognize the hybrid factor VIII, thereby decreasing its immunogenicity.

One method that can be used to further reduce the antigenicity and to construct a less immunogenic hybrid factor VIII is alanine scanning mutagenesis, described by Cunningham, B. C., and J. A. Wells, 244 *Science* 1081–1085 (1989), of selected specific amino acid sequences in human, animal, or hybrid equivalent factor VIII. In alanine scanning mutagenesis, amino acid side chains that are putatively involved in an epitope are replaced by alanine residues by using site-directed mutagenesis. By comparing antibody binding of alanine mutants to wild-type protein, the relative contribution of individual side chains to the binding interaction can be determined. Alanine substitutions are likely to be especially useful, since side chain contributions to antibody binding are eliminated beyond the β carbon, but, unlike glycine substitution, main chain conformation is not usually altered. Alanine substitution does not impose major steric, hydrophobic or electrostatic effects that dominate protein-protein interactions.

In protein antigen-antibody interactions, there usually are about 15–20 antigen side chains in contact with the antibody. Side chain interactions, as opposed to main chain interactions, dominate protein-protein interactions. Recent studies have suggested that only a few (approximately 3 to 5) of these side-chain interactions contribute most: of the binding energy. See Clackson, T., and J. A. Wells, 267 *Science* 383–386 (1995). An extensive analysis of growth hormone epitopes for several murine monoclonal antibodies revealed the following hierarchy for side chain contributions to the binding energy: Arg>Pro>Glu~Asp~Phe~Ile, with Trp, Ala, Gly, and Cys not tested (Jin, L., et al., 226 *J. Mol. Biol.* 851–865 (1992)). Results with the A2 epitope described herein are consistent with this, since twelve of the 25 residues in the 484–508 A2 segment contain these side chains (Table 1).

The finding that certain amino acid residues are particularly well recognized by antibodies, indicates that elimination of these residues from a known epitope can decrease the ability of the immune system to recognize these epitopes, i.e., can make a molecule less immunogenic. In the case of the A2 epitope, immunogenic residues can be replaced without loss of factor VIII coagulant activity. For example, in HP9, Arg484 is replaced by Ser, Pro485 is replaced by Ala, Arg489 is replaced by Gly, Pro492 is replaced by Leu, and Phe501 is replaced by Met. Further, results from the patient plasmas used to test immunoreactivity in hybrid human/porcine factor VIII constructs, described in Example 8, indicate that antibodies from different patients recognize the same or a very similar structural region in the A2 domain and that the residues in the A2 domain that participate in binding A2 inhibitors appear to show little variation. Thus, the A2 epitope included in human factor VIII residues 484–508 is an immunodominant epitope in that it is recognized by the human immune system better than other structural regions of factor VIII. Replacing this structure by nonantigenic factor VIII sequence from another species or by non-factor VIII amino acid sequence, while retaining full procoagulant activity, is expected to alter recognition of hybrid or hybrid equivalent factor VIII by the immune system.

It is anticipated that site-directed mutagenesis to replace bulky and/or charged residues that tend to dominate epitopes with small, neutral side chains (e.g., alanine) may produce a less immunogenic region. It is expected that a molecule containing a few of these substitutions at each significant inhibitor epitope will be difficult for the immune system to fit by the lock-and-key mechanism that is typical of antigen-antibody interactions. Because of its low antigenicity, such a hybrid molecule could be useful in treating factor VIII deficiency patients with inhibitors, and because of its low immunogenicity, it could useful in treating previously untreated patients with hemophilia A.

A general result is that mutation of one of a few key residues is sufficient to decrease the binding constant for a given protein-protein interaction by several orders of magnitude. Thus, it appears likely that all factor VIII epitopes contain a limited number of amino acids that are critical for inhibitor development. For each epitope in factor VIII, alanine substitutions for at least one sequence including one or more specific amino acids having immunogenic activity, may produce an active molecule that is less immunogenic than wild-type factor VIII. In a preferred embodiment, the hybrid factor VIII is B-domainless.

The methods for preparing active recombinant hybrid or hybrid equivalent factor VIII with substitution of amino acid sequence having little or no immunogenic activity for amino acid sequence in the factor VIII having immunogenic activity are as follows, using hybrid human/porcine factor VIII with amino acid substitutions in the A2 domain as an exemplary embodiment. There are 25 residues in the human factor VIII region 484–508. Site-directed mutagenesis can be used to make single mutants in which any of these residues is replaced by any of the other 19 amino acids for a total of 475 mutants. Furthermore, hybrid molecules having more than one mutation can be constructed.

The hybrid constructs can be assayed for antigenicity by measuring the binding constant for inhibitor antibodies, as described by Friguet, B., et al., 77 *J. Immunol. Methods* 77:305–319 (1985). In a preferred embodiment, the binding constant will be reduced by at least three orders of magnitude, which would lower the Bethesda titer to a level that is clinically insignificant. For example, the $IC_{50}$ (a crude measure of the binding constant) of inhibition by A2 antibodies was reduced in hybrid human/porcine factor VIII constructs HP2, HP4, HP5, HP7, and HP9, described in Example 8, and this was associated with a reduction in Bethesda titer to an unmeasurable level. It is anticipated, for example, that a double or triple alanine mutant of human factor VIII (e.g., a human factor VIII Arg484→Ala, Arg489→Ala, Phe501→Ala triple mutant) will produce a molecule with sufficiently low antigenicity for therapeutic use. Similar mutations can be made in the C2 epitope and the putative third epitope. In a preferred embodiment comprises two or three alanine substitutions into two or three factor VIII epitopes. Other substitutions into these regions can be also be done.

In a preferred embodiment, hybrid equivalent factor VIII molecules will be identified that are less antigenic and/or immunogenic in human and animal than either human or porcine factor VIII. Such hybrid equivalent constructs can be tested in animals for their reduced antigenicity and/or immunogenicity. For example, control and factor VIII deficient rabbits, pigs, dogs, mice, primates, and other mammals can be used as animal models. In one experimental protocol, the hybrid or hybrid equivalent factor VIII can be administered systematically over a period of six months to one year to the animal, preferably by intravenous infusion, and in a dosage range between 5 and 50 Units/kg body weight, preferably 10–50 Units/kg, and most preferably 40 Units/kg body weight. Antibodies can be measured in plasma samples taken at intervals after the infusions over the duration of the testing period by routine methods, including immunoassay and the Bethesda assay. Coagulant activity can also be measured in samples with routine procedures, including a one-stage coagulation assay.

The hybrid equivalent factor VIII molecules can be tested in humans for their reduced antigenicity and/or immunogenicity in at least two types of clinical trials. In one type of trial, designed to determine whether the hybrid or hybrid equivalent factor VIII is immunoreactive with inhibitory antibodies, hybrid or hybrid equivalent factor VIII is administered, preferably by intravenous infusion, to approximately 25 patients having factor VIII deficiency who have antibodies to factor VIII that inhibit the coagulant activity of therapeutic human or porcine factor VIII. The dosage of the hybrid or hybrid equivalent factor VIII is in a range between 5 and 50 Units/kg body weight, preferably 10–50 Units/kg, and most preferably 40 Units/kg body weight. Approximately 1 hour after each administration, the recovery of factor VIII from blood samples is measured in a one-stage coagulation assay. Samples are taken again approximately 5 hours after infusion, and recovery is measured. Total recovery and the rate of disappearance of factor VIII from the samples is predictive of the antibody titre and inhibitory activity. If the antibody titre is high, factor VIII recovery usually cannot be measured. The recovery results are compared to the recovery of recovery results in patients treated with plasma-derived human factor VIII, recombinant human factor VIII, porcine factor VIII, and other commonly used therapeutic forms of factor VIII or factor VIII substitutes.

In a second type of clinical trial, designed to determine whether the hybrid or hybrid equivalent factor VIII is immunogenic, i.e., whether patients will develop inhibitory antibodies, hybrid or hybrid equivalent factor VIII is administered, as described in the preceeding paragraph, to approximately 100 previously untreated hemophiliac patients who have not developed antibodies to factor VIII. Treatments are given approximately every 2 weeks over a period of 6 months to 1 year. At 1 to 3 month intervals during this period, blood samples are drawn and Bethesda assays or other antibody assays are performed to determine the presence of inhibitory antibodies. Recovery assays can also be done, as described above, after each infusion. Results are compared to hemophiliac patients who receive plasma-derived human factor VIII, recombinant human factor VIII, porcine factor VIII, or other commonly used therapeutic forms of factor VIII or factor VIII substitutes.

Preparation of hybrid factor VIII molecules using human and non-porcine, non-human mammalian factor VIII amino acid sequence.

The methods used to prepare hybrid human/porcine factor VIII with substitution of specific amino acids can be used to prepare recombinant hybrid human/non-human, non-porcine mammalian or animal/animal factor VIII protein that has, compared to human or porcine factor VIII, altered or the same coagulant activity and/or equal or reduced immunoreactivity and/or immunogenicity, based on substitution of one or more amino acids in the A2, C2, and/or other domains.

Similar comparisons of amino acid sequence identity can be made between human and non-human, non-porcine mammalian factor VIII proteins to determine the amino acid sequences in which procoagulant activity, anti-A2 and anti-C2 immunoreactivity, and or immunogenicity, or immunoreactivity and/or immunogenicity in other domains reside. Similar methods can then be used to prepare hybrid human/non-human, non-porcine mammalian factor VIII molecules. As described above, functional analysis of each hybrid will reveal those with decreased reactivity to inhibitory antibodies, and/or reduced immunogenicity, and/or increased coagulant activity, and the sequence can be further dissected by point mutation analysis.

For example, hybrid human/mouse factor VIII molecules can be prepared as described above. The amino acid sequence alignment of the A2 domain of human (SEQ ID NO:2) and mouse (SEQ ID NO:6) is shown in FIG. 1A–1B. As reported by Elder et al., the factor VIII protein encoded by the mouse cDNA (SEQ ID NO:5) has 2319 amino acids, with 74% sequence identity overall to the human sequence (SEQ ID NO:2) (87 percent identity when the B domain is excluded from the comparison), and is 32 amino acids shorter than human factor VIII. The amino acid sequences in the mouse A and C domains (SEQ ID NO:6) are highly conserved, with 84–93 percent sequence identity to the human sequence (SEQ ID NO:2), while the B and the two short acidic domains have 42–70 percent sequence identity. Specifically, the A1, A2, and A3 mouse amino acid sequences (SEQ ID NO:6) are 85, 85, and 90 percent identical to the corresponding human amino acid sequences (SEQ ID NO:2). The C1 and C2 mouse amino acid sequences are 93 and 84 percent identical to the corresponding human amino acid sequences. In the predicted mouse factor VIII amino acid sequence (SEQ ID NO:6), the A1, A2, and A3 domains are homologous to human factor VIII amino acids 1–372, 373–740, and 1690–2032, respectively, using amino acid sequence identity for numbering purposes.

The thrombin/factor Xa and all but one activated protein C cleavage sites are conserved in mouse factor VIII. The tyrosine residue for von Willebrand factor binding is also conserved.

According to Elder et al., the nucleotide sequence (SEQ ID NO:5) of mouse factor VIII contains 7519 bases and has 67 percent identity overall with the human nucleotide sequence (SEQ ID NO:1). The 6957 base pairs of murine coding sequence have 82 percent sequence identity with the 7053 base pairs of coding sequence in human factor VIII. When the B domain is not included in the comparison, there is an 88 percent nucleotide sequence identity.

Elder et al. report that human and mouse factor VIII molecules are 74 percent identical overall, and that 95 percent of the human residues that lead to hemophilia when altered are identical in the mouse. These data support the application of the same techniques used to identify amino acid sequence with coagulant activity and/or immunoreactivity to antibodies in the porcine factor VIII molecule to the mouse or other animal factor VIII to identify similar amino acid sequences and prepare hybrid molecules.

Preparation of hybrid factor VIII molecules having reduced cross-reactivity using human and non-human, non-porcine mammalian factor VIII amino acid sequence and non-factor VIII amino acid sequence.

Porcine factor VIII is used clinically to treat factor VIII deficiency patients who have inhibitory antibodies to human factor VIII. Cross-reactivity, in which human plasma reacts with porcine factor VIII, can be reduced by preparation of hybrid porcine/non-human, non-porcine mammalian or hybrid equivalent factor VIII. In a preferred embodiment, a determination of whether human A2, C2, or other domain-specific inhibitors react with non-human, non-porcine mammalian ("other mammalian") factor VIII is made, using the routine Bethesda assay and the particular other mammalian plasma as the standard. Inhibitor titers are usually measured in plasma, so purified other mammalian factor VIII is not necessary. If the inhibitors do not react with the other mammalian factor VIII, such as murine factor VIII, the sequence of which is known, then corresponding other mammalian sequence can be substituted into the porcine epitope region, as identified by using human/porcine hybrids. Once the animal sequence is known, site directed mutagenesis techniques, such as oligonucleotide-mediated mutagenesis described by Kunkel, T. A., et al., 204 Meth. Enzymol. 125–139 (1991), can be used to prepare the hybrid porcine/animal factor VIII molecule. If other animal plasmas are less reactive with A2, C2, or other factor VIII inhibitors than murine or porcine factor VIII, the animal sequence corresponding to the porcine epitope can be determined by routine procedures, such as RT-PCR, and a hybrid human/animal or porcine/animal factor VIII constructed by site directed mutagenesis. Also, hybrid human/animal or porcine/non-porcine mammalian factor VIII having reduced cross-reactivity with human plasma compared to porcine factor VIII can be prepared that has corresponding amino acid sequence substitution from one or more other animals. In a further embodiment, cross-reactivity can be reduced by substitution of amino acid sequence having no known identity to factor VIII amino acid sequence, preferably alanine residues using alanine scanning mutagenesis techniques, for porcine epitope sequence.

After identification of clinically significant epitopes, recombinant hybrid factor VIII molecules will be expressed that have less than or equal cross-reactivity compared with porcine factor VIII when tested in vitro against a broad survey of inhibitor plasmas. Preferably these molecules will be combined A2/C2 hybrids in which immunoreactive amino acid sequence in these domains is replaced by other mammalian sequence. Additional mutagenesis in these regions may be done to reduce cross-reactivity. Reduced cross-reactivity, although desirable, is not necessary to produce a product that may have advantages over the existing porcine factor VIII concentrate, which produces side effects due to contaminant porcine proteins and may produce untoward effects due to the immunogenicity of porcine factor VIII sequences. A hybrid human/other mammalian or porcine/other mammalian factor VIII molecule will not contain foreign porcine proteins. Additionally, the extensive epitope mapping accomplished in the porcine A2 domain indicates that greater than 95% of the therapeutic hybrid human/porcine factor VIII sequence will be human.

Preparation of hybrid factor VIII equivalents

The methods for amino acid substitution in factor VIII molecules described above and in the examples can also be used to prepare procoagulant recombinant hybrid factor VIII equivalent molecules or fragments thereof comprising at least one amino acid sequence including one or more amino acids having no known amino acid sequence identity to factor VIII ("non-factor VIII sequence") substituted for at least one specific amino acid sequence that includes an antigenic and/or immunogenic site in human, animal, or hybrid factor VIII. The resulting active hybrid factor VIII equivalent molecule has equal or less reactivity with factor VIII inhibitory antibodies and/or less immunogenicity in human and animals than the unsubstituted human, animal, or hybrid factor VIII.

Suitable amino acid residues that can be substituted for those sequences of amino acids critical to coagulant and/or antigenic and/or immunogenic activity in human or animal factor VIII or hybrid human/animal factor VIII to prepare a hybrid equivalent factor VIII molecule include any amino acids having no known sequence identity to animal or human factor VIII amino acid sequence that has coagulant, antigenic, or immunogenic activity. In a preferred embodiment, the amino acids that can be substituted include alanine residues using alanine scanning mutagenesis techniques.

Hybrid factor VIII equivalent molecules described herein also include those molecules in which amino acid residues having no known identity to animal factor VIII sequence are substituted for amino acid residues not critical to coagulant, antigenic, or immunogenic activity.

As described above, in one embodiment of a hybrid factor VIII equivalent molecule, the molecule has reduced cross-reactivity with inhibitor plasmas. One or more epitopes in the cross-reactive factor VIII are identified, as described above, and then replaced by non-factor VIII amino acid sequence, preferably alanine residues, using, for example, the alanine scanning mutagenesis method.

In a preferred embodiment, a procoagulant recombinant hybrid factor VIII equivalent molecule is prepared comprising at least one sequence including one or more amino acids having no known sequence identity to factor VIII, preferably alanine residues, substituted for at least one sequence including one or more amino acids including an epitope, and/or for at least one sequence including one or more amino acids including an immunogenic site, preferably in human factor VIII. The resulting hybrid equivalent factor VIII molecule or fragment thereof has reduced or no immunoreactivity with inhibitory antibodies to factor VIII and/or reduced or no immunogenicity in human or animals. The methods for identifying specific antigenic amino acid sequence in the A2 domain of human factor VIII for substitution by nonantigenic porcine unique amino acid sequence are described in Examples 7 and 8 and are exemplary for identifying antigenic sequence in the A2 and other domains of human and animal factor VIII and for using site-directed mutagenesis methods such as alanine scanning mutagenesis to substitute non-factor VIII amino acid sequence.

Since the human A2 epitope has been narrowed to 25 or fewer amino acids, as described in Example 8, alanine scanning mutagenesis can be performed on a limited number of hybrid factor VIII constructs having human amino acid sequence to determine which are procoagulant, non-immunoreactive and/or nonimmunogenic hybrid factor VIII constructs based on A2 amino acid substitutions. In the A2 domain, the most likely candidates for alanine substitutions to achieve both reduced antigenicity and immunogenicity in the hybrid construct are Arg484, Pro485, Tyr487, Ser488, Arg489, Pro492, Val495, Phe501, and Ile508. The binding affinity of a hybrid construct comprising each of these mutants for mAb413 and a panel of A2 specific patient IgGs will be determined by ELISA. Any mutant that is active and has a binding affinity for A2 inhibitors that is reduced by more than 2 orders of magnitude is a candidate for the A2 substituted factor VIII molecule. Constructs having more than one mutation will be selected, based on the assumption that the more the epitope is altered, the less immunogenic it will be. It is possible that there are other candidate residues in the region between Arg484-Ile508, since there may be key residues for the epitope that are common to both human and porcine factor VIII. For example, charged residues are frequently involved in protein-protein interactions, so an alanine substitution for Lys493 is a possible candidate.

This procedure will be carried out in the C2 epitope and the putative third epitope, which is thought to be in the A3 or C1 domains, as well as any other epitopes identified in factor VIII, to prepare hybrid equivalent factor VIII constructs.

Diagnostic Assays

The hybrid human/animal, animal/animal, or equivalent factor VIII cDNA and/or protein expressed therefrom, in whole or in part, can be used in assays as diagnostic reagents for the detection of inhibitory antibodies to human or animal factor VIII or to hybrid human/animal factor or equivalent VIII in substrates, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Techniques for preparing these reagents and methods for use thereof are known to those skilled in the art. For example, an immunoassay for detection of inhibitory antibodies in a patient serum sample can include reacting the test sample with a sufficient amount of the hybrid human/animal factor VIII that contains at least one antigenic site, wherein the amount is sufficient to form a detectable complex with the inhibitory antibodies in the sample.

Nucleic acid and amino acid probes can be prepared based on the sequence of the hybrid human/porcine, human/non-human, non-porcine mammalian, animal/animal, or equivalent factor VIII cDNA or protein molecule or fragments thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with a hybrid human/animal or hybrid equivalent factor VIII. The cDNA probes can be used, for example, for research purposes in screening DNA libraries.

Pharmaceutical Compositions

Pharmaceutical compositions containing hybrid human/animal, porcine/non-human, non-porcine mammalian, animal-1/animal-2, or equivalent factor VIII, alone or in combination with appropriate pharmaceutical stabilization compounds, delivery vehicles, and/or carrier vehicles, are prepared according to known methods, as described in Remington's *Pharmaceutical Sciences* by E. W. Martin.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid factor VIII is then introduced into the container. The container is then swirled by hand to free lipid material from the sides of the container and to disperse lipid aggregates, thereby forming the liposomal suspension.

The hybrid factor or hybrid equivalent VIII can be combined with other suitable stabilization compounds, delivery vehicles, and/or carrier vehicles, including vitamin K dependent clotting factors, tissue factor, and von Willebrand factor (vWf) or a fragment of vwf that contains the factor VIII binding site, and polysaccharides such as sucrose.

Hybrid or hybrid equivalent factor VIII can also be delivered by gene therapy in the same way that human factor VIII can be delivered, using delivery means such as retroviral vectors. This method consists of incorporation of factor VIII CDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (e.g., Kohn, D. B., and P. W. Kantoff, 29 Transfusion 812–820, 1989).

Hybrid factor VIII can be stored bound to vwf to increase the half-life and shelf-life of the hybrid molecule. Additionally, lyophilization of factor VIII can improve the yields of active molecules in the presence of vWf. Current methods for storage of human and animal factor VIII used by commercial suppliers can be employed for storage of hybrid factor VIII. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, hybrid factor VIII has been indefinitely stable at 40° C. in 0.6M NaCl, 20 mM MES, and 5 mM CaCl$_2$ at pH 6.0 and also can be stored frozen in these buffers and thawed with minimal loss of activity.

Methods of Treatment

Hybrid or hybrid equivalent factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

Additionally, hybrid or hybrid equivalent factor VIII can be administered by transplant of cells genetically engineered to produce the hybrid or by implantation of a device containing such cells, as described above.

In a preferred embodiment, pharmaceutical compositions of hybrid or hybrid equivalent factor VIII alone or in combination with stabilizers, delivery vehicles, and/or carriers are infused into patients intravenously according to the same procedure that is used for infusion of human or animal factor VIII.

The treatment dosages of hybrid or hybrid equivalent factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the hybrid factor VIII is included in the pharmaceutically acceptable carrier, delivery vehicle, or stabilizer in an amount sufficient to deliver to a patient a therapeutically effective amount of the hybrid to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, J. M., et al., 328 *New. Engl. J. Med.* 453–459 (1993); Pittman, D. D., et al., 79 *Blood* 389–397 (1992), and Brinkhous et al., 82 *Proc. Natl. Acad. Sci.* 8752–8755 (1985).

Usually, the desired plasma factor VIII level to be achieved in the patient through administration of the hybrid or hybrid equivalent factor VIII is in the range of 30–100% of normal. In a preferred mode of administration of the hybrid or hybrid equivalent factor VIII, the composition is given intravenously at a preferred dosage in the range from about 5 to 50 units/kg body weight, more preferably in a range of 10–50 units/kg body weight, and most preferably at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in *Hematology*, Williams, W. J., et al., ed. (1990). Patients with inhibitors may require more hybrid or hybrid equivalent factor VIII, or patients may require less hybrid or hybrid equivalent factor VIII because of its higher specific activity than human factor VIII or decreased antibody reactivity or immunogenicity. As in treatment with human or porcine factor VIII, the amount of hybrid or hybrid equivalent factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required.

Alternatively, hybrid or hybrid equivalent factor VIII can be administered subcutaneously or orally with liposomes in one or several doses at varying intervals of time.

Hybrid or hybrid equivalent factor VIII can also be used to treat uncontrolled bleeding due to factor VIII deficiency in hemophiliacs who have developed antibodies to human factor VIII. In this case, coagulant activity that is superior to that of human or animal factor VIII alone is not necessary. Coagulant activity that is inferior to that of human factor VIII (i.e., less than 3,000 units/mg) will be useful if that activity is not neutralized by antibodies in the patient's plasma.

The hybrid or hybrid equivalent factor VIII molecule and the methods for isolation, characterization, making, and using it generally described above will be further understood with reference to the following non-limiting examples.

EXAMPLE 1
Assay of porcine factor VIII and hybrid human/porcine factor VIII

Porcine factor VIII has more coagulant activity than human factor VIII, based on specific activity of the molecule. These results are shown in Table III in Example 4. This conclusion is based on the use of appropriate standard curves that allow human and porcine factor VIII to be fairly compared. Coagulation assays are based on the ability of factor VIII to shorten the clotting time of plasma derived from a patient with hemophilia A. Two types of assays were employed: the one-stage and the two-stage assay.

In the one-stage assay, 0.1 ml hemophilia A plasma (George King Biomedical, Inc.) was incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation was followed by addition of 0.1 ml 20 mM $CaCl_2$, and the time for development of a fibrin clot was determined by visual inspection.

A unit of factor VIII is defined as the amount present in 1 ml of citrated normal human plasma. With human plasma as the standard, porcine and human factor VIII activity were compared directly. Dilutions of the plasma standard or purified proteins were made into 0.15M NaCl, 0.02M HEPES, pH 7.4. The standard curve was constructed based on 3 or 4 dilutions of plasma, the highest dilution being 1/50, and on $log_{10}$ clotting time plotted against $log_{10}$ plasma concentration, which results in a linear plot. The units of factor VIII in an unknown sample were determined by interpolation from the standard curve.

The one-stage assay relies on endogenous activation of factor VIII by activators formed in the hemophilia A plasma, whereas the two-stage assay measures the procoagulant activity of preactivated factor VIII. In the two-stage assay, samples containing factor VIII that had been reacted with thrombin were added to a mixture of activated partial thromboplastin and human hemophilia A plasma that had been preincubated for 5 min at 37° C. The resulting clotting times were then converted to units/ml, based on the same human standard curve described above. The relative activity in the two-stage assay was higher than in the one-stage assay because the factor VIII had been preactivated.

EXAMPLE 2
Characterization of the functional difference between human and porcine factor VIII The isolation of porcine and human plasma-derived factor VIII and human recombinant factor VIII have been described in the literature in Fulcher, C. A., and T. S. Zimmerman, 79 *Proc. Natl. Acad. Sci. U.S.A.* 1648–1652 (1982); Toole, J. J., et al., 312 *Nature* 342–347 (1984) ((Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech); Fass, D. N., et al., 59 *Blood* 594 (1982); Toole, J. J., et al., 83 *Proc. Nat'l. Acad. Sci. U.S.A.* 5939–5942 (1986). This can be accomplished in several ways. All these preparations are similar in subunit composition, although there is a functional difference in stability between human and porcine factor VIII.

For comparison of human recombinant and porcine factor VIII, preparations; of highly-purified human recombinant factor VIII (Cutter Laboratories, Berkeley, Calif.) and porcine factor VIII (immunopurified as described in Fass, D. N., et al., 59 *Blood* 594 (1982)) were subjected to high-pressure liquid chromatography (HPLC) over a Mono Q™ (Pharmacia-LKB, Piscataway, N.J.) anion-exchange column (Pharmacia, Inc.). The purposes of the Mono Q™ HPLC step were elimination of minor impurities and exchange of human and porcine factor VIII into a common buffer for comparative purposes. Vials containing 1000–2000 units of factor VIII were reconstituted with 5 ml $H_2O$. Hepes (2M at pH 7.4) was then added to a final concentration of 0.02M. Factor VIII was applied to a Mono Q™ HR 5/5 column equilibrated in 0.15M NaCl, 0.02M Hepes, 5 mM $CaCl_2$, at pH 7.4 (Buffer A plus 0.15M NaCl); washed with 10 ml Buffer A+0.15M NaCl; and eluted with a 20 ml linear gradient, 0.15M to 0.90M NaCl in Buffer A at a flow rate of 1 ml/min.

For comparison of human plasma-derived factor VIII (purified by Mono Q™ HPLC) and porcine factor VIII, immunoaffinity-purified, plasma-derived porcine factor VIII was diluted 1:4 with 0.04M Hepes, 5 mM $CaCl_2$, 0.01% Tween-80, at pH 7.4, and subjected to Mono Q™ HPLC under the same conditions described in the previous paragraph for human factor VIII. These procedures for the isolation of human and porcine factor VIII are standard for those skilled in the art.

Column fractions were assayed for factor VIII activity by a one-stage coagulation assay. The average results of the assays, expressed in units of activity per $A_{280}$ of material, are given in Table II, and indicate that porcine factor VIII has at least six times greater activity than human factor VIII when the one-stage assay is used.

TABLE II

COMPARISON OF HUMAN AND PORCINE FACTOR VIII COAGULANT ACTIVITY

|  | Activity (U/$A_{280}$) |
|---|---|
| Porcine | 21,300 |
| Human plasma-derived | 3,600 |
| Human recombinant | 2,400 |

EXAMPLE 3
Comparison of the stability of human and porcine factor VIII

The results of the one-stage assay for factor VIII reflect activation of factor VIII to factor VIIIa in the sample and possibly loss of formed factor VIIIa activity. A direct comparison of the stability of human and porcine factor VIII was made. Samples from Mono Q™ HPLC (Pharmacia, Inc., Piscataway, N.J.) were diluted to the same concentration and buffer composition and reacted with thrombin. At various times, samples were removed for two-stage coagulation assay. Typically, peak activity (at 2 min) was 10-fold greater for porcine than human factor VIIIa, and the activities of both porcine and human factor VIIIa subsequently decreased, with human factor VIIIa activity decreasing more rapidly.

Generally, attempts to isolate stable human factor VIIIa are not successful even when conditions that produce stable porcine factor VIIIa are used. To demonstrate this, Mono Q™ HPLC-purified human factor VIII was activated with thrombin and subjected to Mono S™ cation-exchange (Pharmacia, Inc.) HPLC under conditions that produce stable porcine factor VIIIa, as described by Lollar, J. S., and C. G. Parker, 28 *Biochemistry* 666 (1989).

Human factor VIII, 43 µg/ml (0.2 µM) in 0.2M NaCl, 0.01M Hepes, 2.5 mM $CaCl_2$, at pH 7.4, in 10 ml total volume, was reacted with thrombin (0.036 µM) for 10 min, at which time FPR-$CH_2Cl$ D-phenyl-prolyl-arginyl-chloromethyl ketone was added to a concentration of 0.2 µM for irreversible inactivation of thrombin. The mixture then was diluted 1:1 with 40 mM 2-(N-morpholino)ethane sulfonic acid (MES), 5 mM $CaCl_2$, at pH 6.0, and loaded at 2 ml/min onto a Mono S™ HR 5/5 HPLC column (Pharmacia, Inc.) equilibrated in 5 mM MES, 5 mM $CaCl_2$, at pH 6.0 (Buffer B) plus 0.1M NaCl. Factor VIIIa was eluted without column washing with a 20 ml gradient from 0.1M NaCl to 0.9M NaCl in Buffer B at 1 ml/min.

The fraction with coagulant activity in the two-stage assay eluted as a single peak under these conditions. The specific activity of the peak fraction was approximately 7,500 $U/A_{280}$. Sodium dodecyl sulfate-polyacrylamide gel electrophoresis (SDS-PAGE) of the Mono S™ factor VIIIa peak, followed by silver staining of the protein, revealed two bands corresponding to a heterodimeric (A3-C1-C2/A1) derivative of factor VIII. Although the A2 fragment was not identified by silver staining under these conditions because of its low concentration, it was identified as a trace constituent by $^{125}I$-labeling.

In contrast to the results with human factor VIII, porcine factor VIIIa isolated by Mono S™ HPLC under the same conditions had a specific activity $1.6 \times 10^6$ $U/A_{280}$. Analysis of porcine factor VIIIa by SDS-PAGE revealed 3 fragments corresponding to A1, A2, and A3-C1-C2 subunits, demonstrating that porcine factor VIIIa possesses three subunits.

The results of Mono S™ HPLC of human thrombin-activated factor VIII preparations at pH 6.0 indicate that human factor VIIIa is labile under conditions that yield stable porcine factor VIIIa. However, although trace amounts of A2 fragment were identified in the peak fraction, determination of whether the coagulant activity resulted from small amounts of heterotrimetic factor VIIIa or from heterodimeric factor VIIIa that has a low specific activity was not possible from this method alone.

A way to isolate human factor VIIIa before it loses its A2 subunit is desirable to resolve this question. To this end, isolation was accomplished in a procedure that involves reduction of the pH of the Mono S™ buffers to pH 5. Mono Q™-purified human factor VIII (0.5 mg) was diluted with $H_2O$ to give a final composition of 0.25 mg/ml (1 µM) factor VIII in 0.25M NaCl, 0.01M Hepes, 2.5 mM $CaCl_2$, 0.005% Tween-80, at pH 7.4 (total volume 7.0 ml). Thrombin was added to a final concentration of 0.072 µM and allowed to react for 3 min. Thrombin was then inactivated with FPR-$CH_2Cl$ (0.2 µM). The mixture then was diluted 1:1 with 40 mM sodium acetate, 5 mM $CaCl_2$, 0.01% Tween-80, at pH 5.0, and loaded at 2 ml/min onto a Mono S™ HR 5/5 HPLC column equilibrated in 0.01M sodium acetate, 5 mM $CaCl_2$, 0.01% Tween-80, at pH 5.0, plus 0.1M NaCl. Factor VIIIa was eluted without column washing with a 20 ml gradient from 0.1M NaCl to 1.0M NaCl in the same buffer at 1 ml/min. This resulted in recovery of coagulant activity in a peak that contained detectable amounts of the A2 fragment as shown by SDS-PAGE and silver staining. The specific activity of the peak fraction was ten-fold greater than that recovered at pH 6.0 (75,000 $U/A_{280}$ v. 7,500 $U/A_{280}$). However, in contrast to porcine factor VIIIa isolated at pH 6.0, which is indefinitely stable at 4° C., human factor VIIIa activity decreased steadily over a period of several hours after elution from Mono S™. Additionally, the specific activity of factor VIIIa purified at pH 5.0 and assayed immediately is only 5% that of porcine factor VIIIa, indicating that substantial dissociation occurred prior to assay.

These results demonstrate that both human and porcine factor VIIIa are composed of three subunits (A1, A2, and A3-C1-C2). Dissociation of the A2 subunit is responsible for the loss of activity of both human and porcine factor VIIIa under certain conditions, such as physiological ionic strength, pH, and concentration. The relative stability of porcine factor VIIIa under certain conditions is because of stronger association of the A2 subunit.

EXAMPLE 4
Preparation of hybrid human/porcine factor VIII by reconstitution with subunits.

Porcine factor VIII light chains and factor VIII heavy chains were isolated as follows. A 0.5M solution of EDTA at pH 7.4 was added to Mono Q™-purified porcine factor VIII to a final concentration of 0.05M and was allowed to stand at room temperature for 18-24 h. An equal volume of 10 mM histidine-Cl, 10 mM EDTA, 0.02% v/v Tween 80, at pH 6.0 (Buffer B), was added, and the solution was applied at 1 ml/min to a Mono S™ HR 5/5 column previously equilibrated in Buffer A plus 0.25M NaCl. Factor VIII heavy chains did not bind the resin, as judged by SDS-PAGE. Factor VIII light chain was eluted with a linear, 20 ml, 0.1–0.7M NaCl gradient in Buffer A at 1 ml/min and was homogeneous by SDS-PAGE. Factor VIII heavy chains were isolated by mono Q™ HPLC (Pharmacia, Inc., Piscataway, N.J.) in the following way. Factor VIII heavy chains do not adsorb to mono S™ during the purification of factor VIII light chains. The fall-through material that contained factor VIII heavy chains was adjusted to pH 7.2 by addition of 0.5M Hepes buffer, pH 7.4, and applied to a mono Q∩ HR5/5 HPLC column (Pharmacia, Inc.) equilibrated in 0.1M NaCl, 0.02M Hepes, 0.0% Tween-80, pH 7.4. The column was washed with 10 ml of this buffer, and factor VIII heavy chains were eluted with a 20 ml 0.1–1.0M NaCl gradient in this buffer. Human light chains and heavy chains were isolated in the same manner.

Human and porcine light and heavy chains were reconstituted according to the following steps. Ten µl human or porcine factor VIII light chain, 100 µg/ml, was mixed in 1M NaCl, 0.02M Hepes, 5 mM $CaCl_2$, 0.01% Tween-80, pH 7.4, with (1) 25 µl heterologous heavy chain, 60 µg/ml, in the same buffer; (2) 10 µl 0.02M Hepes, 0.01% Tween-80, pH 7.4; (3) 5 µl 0.6M $CaCl_2$, for 14 hr at room temperature. The mixture was diluted 1/4 with 0.02M MES, 0.01% Tween-80, 5 mM $CaCl_2$, pH 6, and applied to Mono S™ Hr5/5 equilibrated in 0.1M NaCl, 0.02M MES, 0.01% Tween-80, 5 mM $CaCl_2$, pH 6.0. A 20 ml gradient was run from 0.1–1.0M NaCl in the same buffer at 1 ml/min, and 0.5 ml fractions were collected. Absorbance was read at 280 nm of fractions, and fractions were assayed with absorbance for factor VIII activity by the one-stage clotting assay. Heavy chains were present in excess, because free light chain (not associated with heavy chain) also binds Mono S™; excess heavy chains ensure that free light chains are not part of the preparation. Reconstitution experiments followed by Mono S™ HPLC purification were performed with all four possible combinations of chains: human light chain/human heavy chain, human light chain/porcine heavy chain, porcine light chain/porcine heavy chain, porcine light chain/human heavy chain. Table III shows that human light chain/porcine heavy chain factor VIII has activity comparable to native porcine factor VIII (Table II), indicating that structural elements in the porcine heavy chain are responsible for the increased coagulant activity of porcine factor VIII compared to human factor VIII.

TABLE III

COMPARISON OF HYBRID HUMAN/PORCINE
FACTOR VIII COAGULANT ACTIVITY WITH
HUMAN AND PORCINE FACTOR VIII

|  | Activity (U/A$_{280}$) |
| --- | --- |
| Porcine light chain/porcine heavy chain | 30,600 |
| Human light chain/porcine heavy chain | 44,100 |
| Porcine light chain/human heavy chain | 1,100 |
| Human light chain/human heavy chain | 1,000 |

EXAMPLE 5

Preparation of active hybrid human/porcine factor VIII by reconstitution with domains.

The porcine A1/A3-C1-C2 dimer, the porcine A2 domain, the human A1/A3-C1-C2 dimer, and the human A2 domain were each isolated from porcine or human blood, according to the method described in Lollar, P., et al., 267(33) *J. Biol. Chem.* 23652–23657 (Nov. 25, 1992). For example, to isolate the porcine A1/A3-C1-C2 dimer, porcine factor VIIIa (140 µg) at pH 6.0 was raised to pH 8.0 by addition of 5N NaOH for 30 minutes, producing dissociation of the A2 domain and 95 percent inactivation by clotting assay. The mixture was diluted 1:8 with buffer B (20 mM HEPES, 5 mM CaCl$_2$, 0.01 % Tween 80, pH 7.4) and applied to a monos column equilibrated in buffer B. The A1/A3-C1-C2 dimer eluted as a single sharp peak at approximately 0.4M NaCl by using a 0.1–1.0M Nacl gradient in buffer B. To isolate the porcine A2 domain, porcine factor VIIIa was made according to the method of Lollar, P., and C. G. Parker, 28 *Biochem.* 666–674 (1989), starting with 0.64 mg of factor VIII. Free porcine A2 domain w as isolated as a minor component (50 µg) at 0.3M NaCl in the monoS™ chromatogram.

Hybrid human/porcine factor VIII molecules were reconstituted from the dimers and domains as follows. The concentrations and buffer conditions for the purified components were as follows: porcine A2, 0.63 µM in buffer A (5 mM MES; 5 mM CaCl$_2$, 0.01% Tween 80, pH 6.0) plus 0.3M NaCl; porcine A1/A3-C1-C2, 0.27 µM in buffer B plus 0.4M NaCl, pH 7.4; human A2, 1 µM in 0.3M NaCl, 10 mM histidine-HCl, 5 mM CaCl$_2$, 0.01 % Tween 20, pH 6.0; human A1/A3-C1-C2, 0.18 µM in 0.5M NaCl, 10 mM histidine-Cl, 2.5 mM CaCl$_2$, 0.1 % Tween 20, pH 6.0. Reconstitution experiments were done by mixing equal volumes of A2 domain and A1/A3-C1-C2 dimer. In mixing experiments with porcine A1/A3-C1-C2 dimer, the pH was lowered to 6.0 by addition of 0.5M MES, pH 6.0, to 70 mM.

The coagulation activities of all four possible hybrid factor VIIIa molecules-[pA2/(hA1/A3-C1-C2)], [hA2/(pA1/A3-C1-C2)], [pA2/(pA1/pA3-C1-C2)], and [hA2/(hA1/A3-C1-C2)]-were obtained by a two-stage clotting assay at various times.

The generation of activity following mixing the A2 domains and A1/A3-C1-C2 dimers was nearly complete by one hour and was stable for at least 24 hours at 37° C. Table IV shows the activity of reconstituted hybrid factor VIIIa molecules when assayed at 1 hour. The two-stage assay, by which the specific activities of factor VIIIa molecules were obtained, differs from the one-stage assay, and the values cannot be compared to activity values of factor VIII molecules obtained by a one-stage assay.

TABLE IV

COMPARISON OF COAGULANT ACTIVITIES
OF DOMAIN-SUBSTITUTED HYBRID
HUMAN/PORCINE FACTOR VIIIa

| Hybrid fVIIIa | Specific Activity (U/mg) |
| --- | --- |
| Porcine A2 + Human A1/A3-C1-C2 | 140,000 |
| Porcine A2 + Porcine A1/A3-C1-C2 | 70,000 |
| Human A2 + Porcine A1/A3-C1-C2 | 40,000 |
| Human A2 + Human A1/A3-C1-C2 | 40,000 |

Table IV shows that the greatest activity was exhibited by the porcine A2 domain/human A1/A3-C1-C2 dimer, followed by the porcine A2 domain/porcine A1/A3-C1-C2 dimer.

Thus, when the A2 domain of porcine factor VIIIa was mixed with the A1/A3-C1-C2 dimer of human factor VIIIa, coagulant activity was obtained. Further, when the A2 domain of human factor VIIIa was mixed with the A1/A3-C1-C2 dimer of porcine factor VIIIa, coagulant activity was obtained. By themselves, the A2, A1, and A3-C1-C2 regions have no coagulant activity.

EXAMPLE 6

Isolation and sequencing of the A2 domain of porcine factor VIII

Only the nucleotide sequence encoding the B domain and part of the A2 domain of porcine factor VIII has been sequenced previously (Toole, J. J., et al., 83 *Proc. Nat'l. Acad. Sci. U.S.A.* 5939–5942 (1986)). The cDNA and predicted amino acid sequences (SEQ ID NOs:5 and 6, respectively) for the entire porcine factor VIII A2 domain are disclosed herein.

The porcine factor VIII A2 domain was cloned by reverse transcription of porcine spleen total RNA and PCR amplification; degenerate primers based on the known human factor VIII cDNA sequence and an exact porcine primer based on a part of the porcine factor VIII sequence were used. A 1 kb PCR product was isolated and amplified by insertion into a Bluescript™ (Stratagene) phagemid vector.

The porcine A2 domain was completely sequenced by dideoxy sequencing. The cDNA and predicted amino acid sequences are as described in SEQ ID NOs:5 and 6, respectively.

EXAMPLE 7

Preparation of recombinant hybrid human/animal factor VIII

The nucleotide and predicted amino acid sequences (SEQ ID NOs:1 and 2, respectively) of human factor VIII have been described in the literature (Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech)).

Making recombinant hybrid human/animal factor VIII requires that a region of human factor VIII cDNA (Biogen Corp.) be removed and the animal cDNA sequence having sequence identity be inserted. Subsequently, the hybrid cDNA is expressed in an appropriate expression system. As an example, hybrid factor VIII cDNAs were cloned in which some or all of the porcine A2 domain was substituted for the corresponding human A2 sequences. Initially, the entire cDNA sequence corresponding to the A2 domain of human factor VIII and then a smaller part of the A2 domain was looped out by oligonucleotide-mediated mutagenesis, a method commonly known to those skilled in the art (see, e.g., Sambrook, J., E. F. Fritsch, and T. Maniatis, *Molecular Cloning: A Laboratory Manual*, Chapter 15, Cold Spring Harbor Press, Cold Spring Harbor, 1989). The steps were as follows.

Materials.

Methoxycarbonyl-D-cyclohexylglycyl-glyclarginine-p-nitroanilide (Spectrozyme™ Xa) and anti-factor VIII monoclonal antibodies ESH4 and ESH8 were purchased from American Diagnostica (Greenwich, Conn.). Unilamellar phosphatidylcholine/phosphatidylserine (75/25, w/w) vesicles were prepared according to the method of Barenholtz, Y., et al., 16 *Biochemistry* 2806–2810 (1977). Recombinant desulfatohirudin was obtained from Dr. R. B. Wallis, Ciba-Geigy Pharmaceuticals (Cerritos, Calif.). Porcine factors IXa, X, Xa, and thrombin were isolated according to the methods of Lollar, P., et al., 63 *Blood* 1303–1306 (1984), and Duffy, E. J., and P. Lollar, 207 *J. Biol. Chem.* 7621–7827 (1992). Albumin-free pure recombinant human factor VIII was obtained from Baxter-Biotech (Deerfield, Ill.).

Cloning of the porcine factor VIII A2 domain.

The cDNA encoding the porcine A2 domain was obtained following PCR of reverse-transcribed porcine spleen MRNA isolated as described by Chomczyneki, P., and Sacohi, N., 162 *Anal. Biochem.* 156–159 (1987). cDNA was prepared using the first-strand cDNA synthesis kit with random hexamers as primers (Pharmacia, Piscataway, N.J.). PCR was carried out using a 5'-terminal degenerate primer 5' AARCAYCCNAARACNTGGG 3' (SEQ ID NO:11), based on known limited porcine A2 amino acid sequence, and a 3'-terminal exact primer, 5' GCTCGCACTAGGGGGTCT-TGAATTC 3' (SEQ ID NO:12), based on known porcine DNA sequence immediately 3' of the porcine A2 domain. These oligonucleotides correspond to nucleotides 1186–1203 and 2289–2313 in the human sequence (SEQ ID NO:1). Amplification was carried out for 35 cycles (1 minute 94° C., 2 minutes 50° C., 2 minutes 72° C.) using Taq DNA polymerase (Promega Corp., Madison, Wis). The 1.1-kilobase amplified fragment was cloned into pBluescript II KS-(Stratagene) at the EcoRV site using the T-vector procedure, as described by Murchuk, D., et al., 19 *Nucl. Acids Res.* 1154 (1991). *Escherichia coli* XL1-Blue-competent cella were transformed, and plasmid DNA was isolated. Sequencing was carried out in both directions using Sequenase™ version 2.0 (U.S. Biochemical Corp., a Division of Amersham LifeScience, Inc., Arlington Hts, Ill.). This sequence was confirmed by an identical sequence that was obtained by direct sequencing of the PCR product from an independent reverse transcription of spleen RNA from the same pig (CircumVent™, New England Biolabs, Beverly, Mass.). The region containing the epitope for autoantibody RC was identified as 373–536 in human factor VIII (SEQ ID NO:2).

Construction and expression of a hybrid human/porcine factor VIII cDNA.

B-domainless human factor VIII (HB-, from Biogen, Inc. Cambridge, Mass.), which lacks sequences encoding for amino acid residues 741–1648 (SEQ ID NO:2), was used as the starting material for construction of a hybrid human/porcine factor VIII. HB- was cloned into the expression vector ReNeo. To facilitate manipulation, the cDNA for factor VIII was isolated as a XhoI/HpaI fragment from ReNeo and cloned into XhoI/EcoRV digested pBlueSsript II KS. An oligonucleotide, 5' CCTTCCTTTATCCAAATACG-TAGATCAAGAGGAAATTGAC 3' (SEQ ID NO:7), was used in a site-directed mutagenesis reaction using uracil-containing phage DNA, as described by Kunkel, T. A., et al., 204 *Meth. Enzymol.* 125–139 (1991), to simultaneously loop-out the human A2 sequence (nucleotides 1169–2304 in SEQ ID NO:1) and introduce a SnaBI restriction site. The A2-domainless human factor VIII containing plasmid was digested with SnaBI followed by addition of ClaI linkers. The porcine A2 domain was then amplified by PCR using the phosphorylated 5' primer 5' GTAGCGTTGCCAA-GAAGCACCCTAAGACG 3' (SEQ ID NO:8) and 3' primer 5' GAAGAGTAGTACGAGT-TATTTCTCTGGGTTCAATGAC 3' (SEQ ID NO:9), respectively. ClaI linkers were added to the PCR product followed by ligation into the human factor VIII-containing vector. The A1/A2 and A2/A3 junctions were corrected to restore the precise thrombin cleavage and flanking sequences by site-directed mutagenesis using the oligonucleotide shown in SEQ ID NO:8 and nucleotides 1–22 (5' GAA . . . TTC in SEQ ID NO:9) to correct the 5'- and 3'-terminal junctions, respectively. In the resulting construct, designated HP1, the human A2 domain was exactly substituted with the porcine A2 domain. A preliminary product contained an unwanted thymine at the A1-A2 junction as a result of the PCR amplification of the porcine A2 domain. This single base can be looped out by use of the mutagenic oligonucleotide 5' CCTTTATCCAAATACGTAGCGTTTGCCAA(;AAG 3' (SEQ ID NO:10).

A region containing 63% of the porcine NH$_2$-terminal A2 domain, which encompasses the putative A2 epitope, was substituted for the homologous human sequence of B-domainless cDNA by exchanging SpeI/BamHI fragments between the pBluescript plasmids containing human factor VIII and human/porcine A2 factor VIII cDNA. The sequence was confirmed by sequencing the A2 domain and splice sites. Finally, a SpeI/ApaI fragment, containing the entire A2 sequence, was substituted in place of the corresponding sequence in HB-, producing the HP2 construct.

Preliminary expression of HB- and HP2 in COS-7 cells was tested after DEAE-dextran-mediated DNA transfection, as described by Seldon, R. F., in *Current Protocols in Molecular Biology* (Ausubel, F. M., et al., eds), pp. 9.21–9.26, Wiley Interscience, New York. After active factor VIII expression was confirmed and preliminary antibody inhibition studies were done, HB- and HP2 DNA were then stably transfected into baby hamster kidney cells using liposome-mediated transfection (Lipofectin®, Life Technologies, Inc., Gaithersburg, Md.). Plasmid-containing clones were selected for G418 resistance in Dulbecco's modified Eagle's medium-F12, 10% fetal calf serum (DMEM-F12/10% fetal calf serum) containing 400 µg/ml G418, followed by maintenance in DMEM-F12/10% fetal calf serum containing 100 µg/ml G418. Colonies showing maximum expression of HB- and HP2 factor VIII activity were selected by ring cloning and expanded for further characterization.

HB- and HP2 factor VIII expression was compared by plasma-free factor VIII assay, one-stage clotting assay, and enzyme-linked immunosorbent assay using purified recombinant human factor VIII as a standard. Specific coagulant activities of 2600 and 2580 units/mg were obtained for HB- and HP2, respectively. HB- and HP2 produced 1.2 and 1.4 units/ml/48 hours/10$^7$ cells, respectively. This is identical to that of the wild type construct (2,600±200 units/mg). The specific activities of HB- and HP2 were indistinguishable in the plasma-free factor VIII assay.

Construction and expression of hybrid human/non-human, non-porcine mammalian and hybrid equivalent factor VIII.

Cloning of other animal A1, A3, C1, and C2 domains and part domains is feasible with the same strategy that was used for cloning the porcine A2 domain. Fragments of these domains can be cloned by the looping out mutagenesis technique. Excision of the corresponding domains in human factor VIII and any fragments thereof, including single amino acid eliminations, is feasible by looping out mutagenesis as described above. All possible domain replacements, fragments of domain replacements, or single amino acid residue replacements are possible by this approach combined with site-directed mutagenesis techniques, such as splicing by overlap extension and alanine scanning mutagenesis.

The biological activity of recombinant hybrid human/animal and equivalent factor VIII with A1, A2, A3, C1, and/or C2 domain substitutions can be evaluated initially by use of a COS-cell mammalian transient expression system. Hybrid human/animal and equivalent cDNA can be transfected into COS cells, and supernatants can be analyzed for factor VIII activity by use of one-stage and two-stage coagulation assays as described above. Additionally, factor VIII activity can be measured by use of a chromogenic substrate assay, which is more sensitive and allows analysis of larger numbers of samples. Similar assays are standard in the assay of factor VIII activity (Wood, W. I., et al., 312 *Nature* 330–337, 1984; Toole, J. J., et al., 312 *Nature* 342–347, 1984). Expression of recombinant factor VIII in COS cells is also a standard procedure (Toole, J. J., et al., 312 *Nature* 342–347, 1984; Pittman, D. D., and R. J. Kaufman, 85 *Proc. Nat'l. Acad. Sci. U.S.A.* 2429–2433, 1988). The human factor VIII CDNA used as starting material for the recombinant molecules described herein has been expressed in COS cells yielding a product with biological activity. This material, as described above, can be used as a standard to compare hybrid human/animal factor VIII molecules. The activity in the assays is converted to a specific activity for proper comparison of the hybrid molecules. For this, a measurement of the mass of factor VIII produced by the cells is necessary and can be done by immunoassay with purified human and/or animal factor VIII as standards. Immunoassays for factor VIII are routine for those skilled in the art (See, e.g., Lollar, P., et al., 71 *Blood* 137–143, 1988).

EXAMPLE 8

Determination of inhibitory activity in hybrid human/animal and equivalent factor VIII Sequences of human and animal factor VIII likely to be involved as epitopes (i.e., as recognition sites for inhibitory antibodies that react with factor VIII) can be determined using routine procedures, for example through use of assay with antibodies to factor VIII combined with site directed mutagenesis techniques such as splicing by overlap extension methods (SOE), as shown below. Sequences of animal factor VIII that are not antigenic compared to corresponding antigenic human sequences can be identified, and substitutions can be made to insert animal sequences and delete human sequences according to standard recombinant DNA methods. Sequences of amino acids such as alanine residues having no known sequence identity to factor VIII can also be substituted by standard recombinant DNA methods or by alanine scanning mutagenesis. Porcine factor VIII reacts less than human factor VIII with some inhibitory antibodies; this provides a basis for current therapy for patients with inhibitors. After the recombinant hybrids are made, they can be tested in vitro for reactivity with routine assays, including the Bethesda inhibitor assay. Those constructs that are less reactive than native human factor VIII and native animal factor VIII are candidates for replacement therapy.

The epitopes to which most, if not all, inhibitory antibodies reactive with human factor VIII are directed are thought to reside in two regions in the 2332 amino acid human factor VIII molecule, the A2 domain (amino acid residues 373–740) and the C2 domain (amino acid residues 2173–2332, both sequences shown in SEQ ID NO:2). The A2 epitope has been eliminated by making a recombinant hybrid human/porcine factor VIII molecule in which part of the human A2 domain is replaced by the porcine sequence having sequence identity to the replaced human amino acid sequence. This was accomplished, as described in Example 7, by cloning the porcine A2 domain by standard molecular biology techniques and then cutting and splicing within the A2 domain using restriction sites. In the resulting construct, designated HP2, residues 373–604 (SEQ ID NO:4) of porcine factor VIII were substituted into the human A2 domain. HP2 was assayed for immunoreactivity with anti-human factor VIII antibodies using the following methods.

Factor VIII enzyme-linked immunosorbent assay.

Microtiter plate wells were coated with 0.15 ml of 6 μg/ml ESH4, a human factor VIII light-chain antibody, and incubated overnight. After the plate was washed three times with $H_2O$ the wells were blocked for 1 hour with 0.15M NaCl, 10 mM sodium phosphate, 0.05% Tween 20, 0.05% nonfat dry milk, 0.05% sodium azide, pH 7.4. To increase sensitivity, samples containing factor VIII were activated with 30 nM thrombin for 15 minutes. Recombinant desulfatohirudin then was added at 100 nM to inhibit thrombin. The plate was washed again and 0.1 ml of sample or pure recombinant human factor VIII (10–600 ng/ml), used as the standard, were added. Following a 2 hour incubation, the plate was washed and 0.1 ml of biotinylated ESH8, another factor VIII light-chain antibody, was added to each well. ESH8 was biotinylated using the Pierce sulfosuccinimidyl-6-(biotinamide)hexanoate biotinylation kit. After a 1 hour incubation, the plate was washed and 0.1 ml of strepavidin alkaline phosphatase was added to each well. The plate was developed using the Bio-Rad alkaline phosphatase substrate reagent kit, and the resulting absorbance at 405 nm for each well was determined by using a Vmax microtiter plate reader (Molecular Devices, Inc., Sunnyville, Calif.). Unknown factor VIII concentrations were determined from the linear portion of the factor VIII standard curve.

Factor VIII assays.

HB- and HB2 factor VIII were measured in a one-stage clotting assay, which was performed as described above (Bowie, E. J. W., and C. A. Owen, in *Disorders of Hemostasis* (Ratnoff and Forbes, eds) pp. 43–72, Grunn & Stratton, Inc., Orlando, Fla. (1984)), or by a plasma-free assay as follows. HB- or HP2 factor VIII was activated by 40 nM thrombin in 0.15M NaCl, 20 nM HEPES, 5 mM $CaCl_2$, 0.01% Tween 80, pH 7.4, in the presence of 10 nM factor IXa, 425 nM factor X, and 50 μM unilamellar phosphatidylserine/phosphatidylcholine (25/75, w/w) vesicles. After 5 minutes, the reaction was stopped with 0.05M EDTA and 100 nM recombinant desulfatohirudin, and the resultant factor Xa was measured by chromogenic substrate assay, according to the method of Hill-Eubanks, D. C., and P. Lollar, 265 *J. Biol. Chem.* 17854–17858 (1990). Under these conditions, the amount of factor Xa formed was linearly proportional to the starting factor VIII concentration as judged by using purified recombinant human factor VIII (Baxter Biotech, Deerfield, Ill.) as the standard.

Prior to clotting assay, HB- or HP2 factor VIII were concentrated from 48 hour conditioned medium to 10–15 units/ml by heparin-Sepharose™ chromatography. HB- or HP2 factor VIII were added to hemophilia A plasma (George King Biomedical) to a final concentration of 1 unit/mil. Inhibitor titers in RC or MR plasma or a stock solution of mAb 413 IgG (4 µM) were measured by the Bethesda assay as described by Kasper, C. K., et al., 34 *Thromb. Diath. Haemorrh.* 869–872 (1975). Inhibitor IgG was prepared as described by Leyte, A., et al., 266 *J. Biol. Chem.* 740–746 (1991).

HP2 does not react with anti-A2 antibodies. Therefore, residues 373–603 must contain an epitope for anti-A2 antibodies.

Preparation of hybrid human/porcine factor VIII and assay by splicing by overlap extension (SOE).

Several more procoagulant recombinant hybrid human/porcine factor VIII B-domainless molecules with porcine amino acid substitutions in the human A2 region have been prepared to further narrow the A2 epitope. Besides restriction site techniques, the "splicing by overlap extension" method (SOE) as described by Ho, S. N., et al., 77 *Gene* 51–59 (1989), has been used to substitute any arbitrary region of porcine factor VIII cDNA. In SOE, the splice site is defined by overlapping oligonucleotides that can be amplified to produce the desired cDNA by PCR. Ten cDNA constructs, designated HP4 through HP13, have been made. They were inserted into the ReNeo expression vector, stably transfected into baby hamster kidney cells, and expressed to high levels [0.5–1 µg (approximately 3–6 units) /$10^7$ cells/24 hours, as described in Example 7. Factor VIII coagulant activity was determined in the presence and absence of a model murine monoclonal inhibitory antibody specific for the A2 domain, mAb413. In the absence of inhibitor, all of the constructs had a specific coagulant activity that was indistinguishable from B(−) human factor VIII.

The hybrid human/porcine factor VIII constructs were assayed for reactivity with the anti-A2 inhibitor mAb413 using the Bethesda assay (Kasper, C. K., et al., 34 *Thromb Diath. Haemorrh.* 869–872 (1975)). The Bethesda unit (BU) is the standard method for measuring inhibitor titers. The results are shown in Table V, and are compared to recombinant human factor VIII.

TABLE V

COMPARISON OF IMMUNOREACTIVITY OF AMINO ACID-SUBSTITUTED HYBRID HUMAN/PORCINE FACTOR VIII

| Construct | Porcine Substitution | Inhibition mAb413 (BU/mg IgG) |
|---|---|---|
| Human B(−) fVIII | None | 1470 |
| HP4 | 373–540 | <0.7 |
| HP5 | 373–508 | <0.7 |
| HP6 | 373–444 | 1450 |
| HP7 | 445–508 | <0.7 |
| HP8 | 373–483 | 1250 |
| HP9 | 484–508 | <0.7 |

TABLE V-continued

COMPARISON OF IMMUNOREACTIVITY OF AMINO ACID-SUBSTITUTED HYBRID HUMAN/PORCINE FACTOR VIII

| Construct | Porcine Substitution | Inhibition mAb413 (BU/mg IgG) |
|---|---|---|
| HP10 | 373–403 | 1170 |
| HP11 | 404–508 | <0.7 |
| HP12 | 489–508 | <0.7 |
| HP13 | 484–488 | <0.7 |

The boundaries of porcine substitutions are defined by the first amino acids that differ between human and porcine factor VIII at the $NH_2$-terminal and C-terminal ends of the insertion. As shown in Table V, if the Bethesda titer is not measurable (<0.7 BU/mg IgG), then an A2 epitope lies in the region of substituted porcine sequence. The epitope has been progressively narrowed to residues 484–509 (SEQ ID NO:2), consisting of only 25 residues, as exemplified by non-reactivity of mAb413 with HP9. Among constructs HP4 through HP11, HP9 was the most "humanized" construct that did not react with the inhibitor. This indicates that a critical region in the A2 epitope is located within the sequence Arg484-Ile508.

Based on a comparison between human and porcine factor VIII of the amino acid sequence in this critical region, two more constructs, HP12 and HP13, were made, in which corresponding porcine amino acid sequence was substituted for human amino acids 489–508 and 484–488, respectively. Neither reacts with mAb413. This indicates that residues on each side of the Arg488-Ser489 bond are important for reaction with A2 inhibitors. In HP12 only 5 residues are non-human, and in HP13 only 4 residues are non-human. The 484–508, 484–488, and 489–508 porcine substituted hybrids displayed decreased inhibition by A2 inhibitors from four patient plasmas, suggesting that there is little variation in the structure of the A2 epitope according to the inhibitor population response.

The reactivity of the most humanized constructs, HP9, HP12, and HP13, with two anti-A2 IgG5 preparations prepared from inhibitor plasmas was determined. Like mAb413, these antibodies did not react with HP9, HP12, and HP13, but did react with the control constructs HB(−) and HP8.

The region between 484–508 can be further analyzed for final identification of the critical A2 epitope, using the same procedures.

The methods described in Examples 7 and 8 can be used to prepare other hybrid human/non-porcine mammalian factor VIII with amino acid substitution in the human A2 or other domains, hybrid human/animal or animal/animal factor VIII with amino acid substitution in any domain, or hybrid factor VIII equivalent molecules or fragments of any of these, such hybrid factor VIII having reduced or absent immunoreactivity with anti-factor VIII antibodies.

Although only preferred embodiments are specifically illustrated and described herein, it will be appreciated that many modifications and variations of the present invention are possible in light of the above teachings and within the purview of the appended claims without departing from the spirit and intended scope of the invention.

We claim:

1. A procoagulant hybrid factor VIII comprising human factor VIII having a sequence of amino acids substituted for a sequence selected from the group of A2 domain fragments consisting of amino acids 373–540, 373–508, 445–508, 484–508, 404–508, 489–508 and 484–489 according to SEQ ID NO:2, the substitution being a corresponding sequence of a non-human mammalian factor VIII.

2. The hybrid factor VIII of claim 1 wherein the corresponding non-human mammalian sequence substituted for amino acids 373–540 of SEQ ID NO: 2 is amino acids 1–168 of SEQ ID NO: 4.

3. The hybrid factor VIII of claim 1 wherein the corresponding non-human mammalian sequence substituted for amino acids 373–508 of SEQ ID NO: 2 is amino acids 1–136 of SEQ ID NO: 4.

4. The hybrid factor VIII of claim 1 wherein the corresponding non-human mammalian sequence substituted for amino acids 445–508 of SEQ ID NO: 2 is amino acids 73–136 of SEQ ID NO: 4.

5. The hybrid factor VIII of claim 1 wherein the corresponding non-human mammalian sequence substituted for amino acids 484–508 of SEQ ID NO: 2 is amino acids 112–136 of SEQ ID NO: 4.

6. The hybrid factor VIII of claim 1 wherein the corresponding non-human mammalian sequence substituted for amino acids 404–508 of SEQ ID NO: 2 is amino acids 32–136 of SEQ ID NO: 4.

7. The hybrid factor VIII of claim 1 wherein the corresponding non-human mammalian sequence substituted for amino acids 489–508 of SEQ ID NO: 2 is amino acids 117–136 of SEQ ID NO: 4.

8. The hybrid factor VIII of claim 1 wherein the corresponding non-human mammalian sequence substituted for amino acids 484–488 of SEQ ID NO: 2 is amino acids 112–116 of SEQ ID NO: 4.

9. The hybrid factor VIII of claim 1 wherein the corresponding non-human mammalian sequence substituted for amino acids 373–540 of SEQ ID NO: 2 is amino acids 392–559 of SEQ ID NO: 6.

10. The hybrid factor VIII of claim 1 wherein the corresponding non-human mammalian sequence substituted for amino acids 445–508 of SEQ ID NO: 2 is amino acids 464–527 of SEQ ID NO: 6.

11. The hybrid factor VIII of claim 1 wherein the corresponding non-human mammalian sequence substituted for amino acids 484–508 of SEQ ID NO: 2 is amino acids 503–527 of SEQ ID NO: 6.

12. The hybrid factor VIII of claim 1 wherein the corresponding non-human mammalian sequence substituted for amino acids 404–508 of SEQ ID NO: 2 is amino acids 423–527 of SEQ ID NO: 6.

13. The hybrid factor VIII of claim 1 wherein the corresponding non-human mammalian sequence substituted for amino acids 489–508 of SEQ ID NO: 2 is amino acids 508–527 of SEQ ID NO: 6.

14. The hybrid factor VIII of claim 1 wherein the corresponding non-human mammalian sequence substituted for amino acids 484–488 of SEQ ID NO: 2 is amino acids 503–507 of SEQ ID NO: 6.

15. A method for treating factor VIII deficiency comprising administering a therapeutically effective dose of a hybrid factor VIII having a sequence of amino acids substituted for a sequence selected from the group consisting of amino acids 373–540, 373–508, 445–508, 484–508, 404–508, 489–508 and 484–489 according to SEQ ID NO:2, the substitution being a corresponding sequence of a non-human mammalian factor VIII, in a pharmaceutically acceptable carrier.

16. The method of claim 15 wherein the administered dose is in the range of 5–50 units/kg body weight.

17. The method of claim 15 wherein the administered dose is in the range of 10–50 units/kg body weight.

18. The method of claim 15 wherein the administered dose is in the range of 20–40 units/kg body weight.

19. The method of claim 15 wherein the carrier comprises von Willeb and factor.

20. The method of claim 15 wherein the factor VIII deficiency has not been previously treated with human factor VIII.

* * * * *

UNITED STATES PATENT AND TRADEMARK OFFICE
CERTIFICATE OF CORRECTION

PATENT NO. : 5,744,446

DATED : April 28, 1998

INVENTOR(S) : Lollar et al.

It is certified that error appears in the above-identified patent and that said Letters Patent is hereby corrected as shown below:

In Col. 19, line 27, replace "$A1_p\text{-}A2_p\text{-}A3_p\text{-}C1_H\text{-}C2^p$" with --$A1_p\text{-}A2_p\text{-}A3_p\text{-}C1_H\text{-}C2_p$--.
In Col. 19, line 43, replace "$A2_p\text{-}A3_p\text{-}C1H\text{-}C2_p$" with --$A2_p\text{-}A3_p\text{-}C1_H\text{-}C2_p$--.
In Col. 27, line 53, rewrite "40° C." as --4° C.--.
In Col. 32, line 43, replace "Qn" with --Q™--.
In Col. 33, line 38, rewrite "monos" as --monoS--.
In Col. 36, line 35, replace "CCTTTATCCAAATACGTAGCGTTTGCCAA(;AAG" with
--CCTTTATCCAAATACGTAGCGTTTGCCAAGAAG--.

In the Claims:

Claim 19, line 2, "Willeb and" should read ---Willebrand---

Signed and Sealed this

Eighth Day of September, 1998

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 9009 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapien
        ( F ) TISSUE TYPE: Liver ( i x ) FEATURE:
        ( A ) NAME/KEY: misc_feature (Domain Structure)
        ( B ) LOCATION: 5125 ... 7053
        ( D ) OTHER INFORMATION: /note="Equivalent to the A3-C1-C2
            domain"

( i x ) FEATURE:
        ( A ) NAME/KEY: misc_feature (Domain Structure)
        ( B ) LOCATION: 1 ... 2277
        ( D ) OTHER INFORMATION: /note="Equivalent to the A1-A2
            domain."

( i x ) FEATURE:
        ( A ) NAME/KEY: Domain
        ( B ) LOCATION: 1..2277
        ( D ) OTHER INFORMATION: /note="cDNA encoding human factor
            VIII."

( x i ) SEQUENCE DESCRIPTION: SEQ ID NO:1:

```
CAGTGGGTAA GTTCCTTAAA TGCTCTGCAA AGAAATTGGG ACTTTTCATT AAATCAGAAA      60
TTTTACTTTT TTCCCCTCCT GGGAGCTAAA GATATTTTAG AGAAGAATTA ACCTTTTGCT     120
TCTCCAGTTG AACATTTGTA GCAATAAGTC ATGCAAATAG AGCTCTCCAC CTGCTTCTTT     180
CTGTGCCTTT TGCGATTCTG CTTTAGTGCC ACCAGAAGAT ACTACCTGGG TGCAGTGGAA     240
CTGTCATGGG ACTATATGCA AAGTGATCTC GGTGAGCTGC TGTGGACGC  AAGATTTCCT     300
CCTAGAGTGC CAAAATCTTT TCCATTCAAC ACCTCAGTCG TGTACAAAAA GACTCTGTTT     360
GTAGAATTCA CGGTTCACCT TTTCAACATC GCTAAGCCAA GGCCACCCTG GATGGGTCTG     420
CTAGGTCCTA CCATCCAGGC TGAGGTTTAT GATACAGTGG TCATTACACT TAAGAACATG     480
GCTTCCCATC CTGTCAGTCT TCATGCTGTT GGTGTATCCT ACTGGAAAGC TTCTGAGGGA     540
GCTGAATATG ATGATCAGAC CAGTCAAAGG GAGAAAGAAG ATGATAAAGT CTTCCCTGGT     600
GGAAGCCATA CATATGTCTG GCAGGTCCTG AAAGAGAATG GTCCAATGGC CTCTGACCCA     660
CTGTGCCTTA CCTACTCATA TCTTTCTCAT GTGGACCTGG TAAAAGACTT GAATTCAGGC     720
CTCATTGGAG CCCTACTAGT ATGTAGAGAA GGGAGTCTGG CCAAGGAAAA GACACAGACC     780
TTGCACAAAT TTATACTACT TTTTGCTGTA TTTGATGAAG GGAAAAGTTG GCACTCAGAA     840
ACAAAGAACT CCTTGATGCA GGATAGGGAT GCTGCATCTG CTCGGGCCTG GCCTAAAATG     900
CACACAGTCA ATGGTTATGT AAACAGGTCT CTGCCAGGTC TGATTGGATG CCACAGGAAA     960
TCAGTCTATT GGCATGTGAT TGGAATGGGC ACCACTCCTG AAGTGCACTC AATATTCCTC    1020
```

```
GAAGGTCACA CATTTCTTGT GAGGAACCAT CGCCAGGCGT CCTTGGAAAT CTCGCCAATA    1080
ACTTTCCTTA CTGCTCAAAC ACTCTTGATG GACCTTGGAC AGTTTCTACT GTTTTGTCAT    1140
ATCTCTTCCC ACCAACATGA TGGCATGGAA GCTTATGTCA AAGTAGACAG CTGTCCAGAG    1200
GAACCCCAAC TACGAATGAA AAATAATGAA GAAGCGGAAG ACTATGATGA TGATCTTACT    1260
GATTCTGAAA TGGATGTGGT CAGGTTTGAT GATGACAACT CTCCTTCCTT TATCCAAATT    1320
CGCTCAGTTG CCAAGAAGCA TCCTAAAACT TGGGTACATT ACATTGCTGC TGAAGAGGAG    1380
GACTGGGACT ATGCTCCCTT AGTCCTCGCC CCCGATGACA GAAGTTATAA AAGTCAATAT    1440
TTGAACAATG GCCCTCAGCG GATTGGTAGG AAGTACAAAA AAGTCCGATT TATGGCATAC    1500
ACAGATGAAA CCTTTAAGAC TCGTGAAGCT ATTCAGCATG AATCAGGAAT CTTGGGACCT    1560
TTACTTTATG GGAAGTTGG AGACACACTG TTGATTATAT TTAAGAATCA AGCAAGCAGA    1620
CCATATAACA TCTACCCTCA CGGAATCACT GATGTCCGTC CTTTGTATTC AAGGAGATTA    1680
CCAAAAGGTG TAAAACATTT GAAGGATTTT CCAATTCTGC CAGGAGAAAT ATTCAAATAT    1740
AAATGGACAG TGACTGTAGA AGATGGGCCA ACTAAATCAG ATCCTCGGTG CCTGACCCGC    1800
TATTACTCTA GTTCGTTAA TATGGAGAGA GATCTAGCTT CAGGACTCAT TGGCCCTCTC    1860
CTCATCTGCT ACAAAGAATC TGTAGATCAA AGAGGAAACC AGATAATGTC AGACAAGAGG    1920
AATGTCATCC TGTTTTCTGT ATTTGATGAG AACCGAAGCT GGTACCTCAC AGAGAATATA    1980
CAACGCTTTC TCCCCAATCC AGCTGGAGTG CAGCTTGAGG ATCCAGAGTT CCAAGCCTCC    2040
AACATCATGC ACAGCATCAA TGGCTATGTT TTTGATAGTT TGCAGTTGTC AGTTTGTTTG    2100
CATGAGGTGG CATACTGGTA CATTCTAAGC ATTGGAGCAC AGACTGACTT CCTTTCTGTC    2160
TTCTTCTCTG GATATACCTT CAAACACAAA ATGGTCTATG AAGACACACT CACCCTATTC    2220
CCATTCTCAG GAGAAACTGT CTTCATGTCG ATGGAAAACC CAGGTCTATG GATTCTGGGG    2280
TGCCACAACT CAGACTTTCG GAACAGAGGC ATGACCGCCT TACTGAAGGT TTCTAGTTGT    2340
GACAAGAACA CTGGTGATTA TTACGAGGAC AGTTATGAAG ATATTTCAGC ATACTTGCTG    2400
AGTAAAAACA ATGCCATTGA ACCAAGAAGC TTCTCCCAGA ATTCAAGACA CCCTAGCACT    2460
AGGCAAAAGC AATTTAATGC CACCACAATT CCAGAAAATG ACATAGAGAA GACTGACCCT    2520
TGGTTTGCAC ACAGAACACC TATGCCTAAA ATACAAAATG TCTCCTCTAG TGATTTGTTG    2580
ATGCTCTTGC GACAGAGTCC TACTCCACAT GGGCTATCCT TATCTGATCT CCAAGAAGCC    2640
AAATATGAGA CTTTTTCTGA TGATCCATCA CCTGGAGCAA TAGACAGTAA TAACAGCCTG    2700
TCTGAAATGA CACACTTCAG GCCACAGCTC CATCACAGTG GGACATGGT ATTTACCCCT    2760
GAGTCAGGCC TCCAATTAAG ATTAAATGAG AAACTGGGGA CAACTGCAGC AACAGAGTTG    2820
AAGAAACTTG ATTTCAAAGT TTCTAGTACA TCAAATAATC TGATTTCAAC AATTCCATCA    2880
GACAATTTGG CAGCAGGTAC TGATAATACA AGTTCCTTAG GACCCCAAG TATGCCAGTT    2940
CATTATGATA GTCAATTAGA TACCACTCTA TTTGGCAAAA AGTCATCTCC CCTTACTGAG    3000
TCTGGTGGAC CTCTGAGCTT GAGTGAAGAA ATAATGATT CAAAGTTGTT AGAATCAGGT    3060
TTAATGAATA GCCAAGAAAG TTCATGGGGA AAAAATGTAT CGTCAACAGA GAGTGGTAGG    3120
TTATTTAAAG GGAAAAGAGC TCATGGACCT GCTTGTTGA CTAAAGATAA TGCCTTATTC    3180
AAAGTTAGCA TCTCTTTGTT AAAGACAAAC AAAACTTCCA ATAATTCAGC AACTAATAGA    3240
AAGACTCACA TTGATGGCCC ATCATTATTA ATTGAGAATA GTCCATCAGT CTGGCAAAAT    3300
ATATTAGAAA GTGACACTGA GTTTAAAAAA GTGACACCTT TGATTCATGA CAGAATGCTT    3360
ATGGACAAAA ATGCTACAGC TTTGAGGCTA AATCATATGT CAAATAAAAC TACTTCATCA    3420
```

| | | | | | |
|---|---|---|---|---|---|
| AAAAACATGG | AAATGGTCCA | ACAGAAAAAA | GAGGGCCCCA | TTCCACCAGA | TGCACAAAAT | 3480
| CCAGATATGT | CGTTCTTTAA | GATGCTATTC | TTGCCAGAAT | CAGCAAGGTG | GATACAAAGG | 3540
| ACTCATGGAA | AGAACTCTCT | GAACTCTGGG | CAAGGCCCCA | GTCCAAAGCA | ATTAGTATCC | 3600
| TTAGGACCAG | AAAAATCTGT | GGAAGGTCAG | AATTTCTTGT | CTGAGAAAAA | CAAAGTGGTA | 3660
| GTAGGAAAGG | GTGAATTTAC | AAAGGACGTA | GGACTCAAAG | AGATGGTTTT | TCCAAGCAGC | 3720
| AGAAACCTAT | TTCTTACTAA | CTTGGATAAT | TTACATGAAA | ATAATACACA | CAATCAAGAA | 3780
| AAAAAAATTC | AGGAAGAAAT | AGAAAGAAG | GAAACATTAA | TCCAAGAGAA | TGTAGTTTTG | 3840
| CCTCAGATAC | ATACAGTGAC | TGGCACTAAG | AATTTCATGA | AGAACCTTTT | CTTACTGAGC | 3900
| ACTAGGCAAA | ATGTAGAAGG | TTCATATGAG | GGGCATATG | CTCCAGTACT | TCAAGATTTT | 3960
| AGGTCATTAA | ATGATTCAAC | AAATAGAACA | AAGAAACACA | CAGCTCATTT | CTCAAAAAAA | 4020
| GGGGAGGAAG | AAAACTTGGA | AGGCTTGGGA | AATCAAACCA | AGCAAATTGT | AGAGAAATAT | 4080
| GCATGCACCA | CAAGGATATC | TCCTAATACA | AGCCAGCAGA | ATTTGTCAC | GCAACGTAGT | 4140
| AAGAGAGCTT | TGAAACAATT | CAGACTCCCA | CTAGAAGAAA | CAGAACTTGA | AAAAGGATA | 4200
| ATTGTGGATG | ACACCTCAAC | CCAGTGGTCC | AAAAACATGA | AACATTTGAC | CCCGAGCACC | 4260
| CTCACACAGA | TAGACTACAA | TGAGAAGGAG | AAAGGGGCCA | TTACTCAGTC | TCCCTTATCA | 4320
| GATTGCCTTA | CGAGGAGTCA | TAGCATCCCT | CAAGCAAATA | GATCTCCATT | ACCCATTGCA | 4380
| AAGGTATCAT | CATTTCCATC | TATTAGACCT | ATATATCTGA | CCAGGGTCCT | ATTCCAAGAC | 4440
| AACTCTTCTC | ATCTTCCAGC | AGCATCTTAT | AGAAAGAAAG | ATTCTGGGGT | CCAAGAAAGC | 4500
| AGTCATTTCT | TACAAGGAGC | CAAAAAAAAT | AACCTTTCTT | TAGCCATTCT | AACCTTGGAG | 4560
| ATGACTGGTG | ATCAAAGAGA | GGTTGGCTCC | CTGGGGACAA | GTGCCACAAA | TTCAGTCACA | 4620
| TACAAGAAAG | TTGAGAACAC | TGTTCTCCCG | AAACCAGACT | TGCCCAAAAC | ATCTGGCAAA | 4680
| GTTGAATTGC | TTCCAAAAGT | TCACATTTAT | CAGAAGGACC | TATTCCCTAC | GGAAACTAGC | 4740
| AATGGGTCTC | CTGGCCATCT | GGATCTCGTG | GAAGGGAGCC | TTCTTCAGGG | AACAGAGGGA | 4800
| GCGATTAAGT | GGAATGAAGC | AAACAGACCT | GGAAAAGTTC | CCTTTCTGAG | AGTAGCAACA | 4860
| GAAAGCTCTG | CAAAGACTCC | CTCCAAGCTA | TTGGATCCTC | TTGCTTGGGA | TAACCACTAT | 4920
| GGTACTCAGA | TACCAAAAGA | AGAGTGGAAA | TCCCAAGAGA | AGTCACCAGA | AAAAACAGCT | 4980
| TTTAAGAAAA | AGGATACCAT | TTTGTCCCTG | AACGCTTGTG | AAAGCAATCA | TGCAATAGCA | 5040
| GCAATAAATG | AGGGACAAAA | TAAGCCCGAA | ATAGAAGTCA | CCTGGGCAAA | GCAAGGTAGG | 5100
| ACTGAAAGGC | TGTGCTCTCA | AAACCCACCA | GTCTTGAAAC | GCCATCAACG | GGAAATAACT | 5160
| CGTACTACTC | TTCAGTCAGA | TCAAGAGGAA | ATTGACTATG | ATGATACCAT | ATCAGTTGAA | 5220
| ATGAAGAAGG | AAGATTTTGA | CATTTATGAT | GAGGATGAAA | ATCAGAGCCC | CGCAGCTTTT | 5280
| CAAAAGAAAA | CACGACACTA | TTTTATTGCT | GCAGTGGAGA | GGCTCTGGGA | TTATGGGATG | 5340
| AGTAGCTCCC | CACATGTTCT | AAGAAACAGG | GCTCAGAGTG | CAGTGTCCC | TCAGTTCAAG | 5400
| AAAGTTGTTT | TCCAGGAATT | TACTGATGGC | TCCTTTACTC | AGCCCTTATA | CCGTGGAGAA | 5460
| CTAAATGAAC | ATTTGGGACT | CCTGGGGCCA | TATATAAGAG | CAGAAGTTGA | AGATAATATC | 5520
| ATGGTAACTT | TCAGAAATCA | GGCCTCTCGT | CCCTATTCCT | TCTATTCTAG | CCTTATTTCT | 5580
| TATGAGGAAG | ATCAGAGGCA | AGGAGCAGAA | CCTAGAAAAA | ACTTTGTCAA | GCCTAATGAA | 5640
| ACCAAAACTT | ACTTTTGGAA | AGTGCAACAT | CATATGGCAC | CCACTAAAGA | TGAGTTTGAC | 5700
| TGCAAAGCCT | GGGCTTATTT | CTCTGATGTT | GACCTGGAAA | AAGATGTGCA | CTCAGGCCTG | 5760
| ATTGGACCCC | TTCTGGTCTG | CCACACTAAC | ACACTGAACC | CTGCTCATGG | GAGACAAGTG | 5820

```
ACAGTACAGG AATTTGCTCT GTTTTTCACC ATCTTTGATG AGACCAAAAG CTGGTACTTC   5880
ACTGAAAATA TGGAAAGAAA CTGCAGGGCT CCCTGCAATA TCCAGATGGA AGATCCCACT   5940
TTTAAAGAGA ATTATCGCTT CCATGCAATC AATGGCTACA TAATGGATAC ACTACCTGGC   6000
TTAGTAATGG CTCAGGATCA AAGGATTCGA TGGTATCTGC TCAGCATGGG CAGCAATGAA   6060
AACATCCATT CTATTCATTT CAGTGGACAT GTGTTCACTG TACGAAAAAA AGAGGAGTAT   6120
AAAATGGCAC TGTACAATCT CTATCCAGGT GTTTTTGAGA CAGTGGAAAT GTTACCATCC   6180
AAAGCTGGAA TTTGGCGGGT GGAATGCCTT ATTGGCGAGC ATCTACATGC TGGGATGAGC   6240
ACACTTTTTC TGGTGTACAG CAATAAGTGT CAGACTCCCC TGGGAATGGC TTCTGGACAC   6300
ATTAGAGATT TTCAGATTAC AGCTTCAGGA CAATATGGAC AGTGGGCCCC AAAGCTGGCC   6360
AGACTTCATT ATTCCGGATC AATCAATGCC TGGAGCACCA AGGAGCCCTT TTCTTGGATC   6420
AAGGTGGATC TGTTGGCACC AATGATTATT CACGGCATCA AGACCCAGGG TGCCCGTCAG   6480
AAGTTCTCCA GCCTCTACAT CTCTCAGTTT ATCATCATGT ATAGTCTTGA TGGGAAGAAG   6540
TGGCAGACTT ATCGAGGAAA TTCCACTGGA ACCTTAATGG TCTTCTTTGG CAATGTGGAT   6600
TCATCTGGGA TAAAACACAA TATTTTTAAC CCTCCAATTA TTGCTCGATA CATCCGTTTG   6660
CACCCAACTC ATTATAGCAT TCGCAGCACT CTTCGCATGG AGTTGATGGG CTGTGATTTA   6720
AATAGTTGCA GCATGCCATT GGGAATGGAG AGTAAAGCAA TATCAGATGC ACAGATTACT   6780
GCTTCATCCT ACTTTACCAA TATGTTTGCC ACCTGGTCTC CTTCAAAAGC TCGACTTCAC   6840
CTCCAAGGGA GGAGTAATGC CTGGAGACCT CAGGTGAATA ATCCAAAAGA GTGGCTGCAA   6900
GTGGACTTCC AGAAGACAAT GAAAGTCACA GGAGTAACTA CTCAGGGAGT AAAATCTCTG   6960
CTTACCAGCA TGTATGTGAA GGAGTTCCTC ATCTCCAGCA GTCAAGATGG CCATCAGTGG   7020
ACTCTCTTTT TTCAGAATGG CAAAGTAAAG GTTTTTCAGG GAAATCAAGA CTCCTTCACA   7080
CCTGTGGTGA ACTCTCTAGA CCCACCGTTA CTGACTCGCT ACCTTCGAAT TCACCCCCAG   7140
AGTTGGGTGC ACCAGATTGC CCTGAGGATG GAGGTTCTGG GCTGCGAGGC ACAGGACCTC   7200
TACTGAGGGT GGCCACTGCA GCACCTGCCA CTGCCGTCAC CTCTCCCTCC TCAGCTCCAG   7260
GGCAGTGTCC CTCCCTGGCT TGCCTTCTAC CTTTGTGCTA AATCCTAGCA GACACTGCCT   7320
TGAAGCCTCC TGAATTAACT ATCATCAGTC CTGCATTTCT TTGGTGGGGG GCCAGGAGGG   7380
TGCATCCAAT TTAACTTAAC TCTTACCTAT TTCTGCAGC TGCTCCCAGA TTACTCCTTC   7440
CTTCCAATAT AACTAGGCAA AAAGAAGTGA GGAGAAACCT GCATGAAAGC ATTCTTCCCT   7500
GAAAAGTTAG GCCTCTCAGA GTCACCACTT CCTCTGTTGT AGAAAAACTA TGTGATGAAA   7560
CTTTGAAAAA GATATTTATG ATGTTAACAT TCAGGTTAA GCCTCATACG TTTAAAATAA   7620
AACTCTCAGT TGTTTATTAT CCTGATCAAG CATGGAACAA AGCATGTTTC AGGATCAGAT   7680
CAATACAATC TTGGAGTCAA AAGGCAAATC ATTTGGACAA TCTGCAAAAT GGAGAGAATA   7740
CAATAACTAC TACAGTAAAG TCTGTTTCTG CTTCCTTACA CATAGATATA ATTATGTTAT   7800
TTAGTCATTA TGAGGGGCAC ATTCTTATCT CCAAAACTAG CATTCTTAAA CTGAGAATTA   7860
TAGATGGGGT TCAAGAATCC CTAAGTCCCC TGAAATTATA TAAGGCATTC TGTATAAATG   7920
CAAATGTGCA TTTTTCTGAC GAGTGTCCAT AGATATAAAG CCATTGGTCT TAATTCTGAC   7980
CAATAAAAAA ATAAGTCAGG AGGATGCAAT TGTTGAAAGC TTTGAAATAA AATAACATGT   8040
CTTCTTGAAA TTTGTGATGG CCAAGAAAGA AAATGATGAT GACATTAGGC TTCTAAAGGA   8100
CATACATTTA ATATTTCTGT GGAAATATGA GGAAAATCCA TGGTTATCTG AGATAGGAGA   8160
TACAAACTTT GTAATTCTAA TAATGCACTC AGTTACTCT CTCCCTCTAC TAATTTCCTG   8220
```

| CTGAAAATAA | CACAACAAAA | ATGTAACAGG | GGAAATTATA | TACCGTGACT | GAAAACTAGA | 8280 |
| GTCCTACTTA | CATAGTTGAA | ATATCAAGGA | GGTCAGAAGA | AAATTGGACT | GGTGAAAACA | 8340 |
| GAAAAAACAC | TCCAGTCTGC | CATATCACCA | CACAATAGGA | TCCCCCTTCT | TGCCCTCCAC | 8400 |
| CCCCATAAGA | TTGTGAAGGG | TTTACTGCTC | CTTCCATCTG | CCTGCACCCC | TTCACTATGA | 8460 |
| CTACACAGAA | CTCTCCTGAT | AGTAAAGGGG | GCTGGAGGCA | AGGATAAGTT | ATAGAGCAGT | 8520 |
| TGGAGGAAGC | ATCCAAAGAC | TGCAACCCAG | GGCAAATGGA | AAACAGGAGA | TCCTAATATG | 8580 |
| AAAGAAAAAT | GGATCCCAAT | CTGAGAAAAG | GCAAAGAAT | GGCTACTTTT | TTCTATGCTG | 8640 |
| GAGTATTTTC | TAATAATCCT | GCTTGACCCT | TATCTGACCT | CTTTGGAAAC | TATAACATAG | 8700 |
| CTGTCACAGT | ATAGTCACAA | TCCACAAATG | ATGCAGGTGC | AAATGGTTTA | TAGCCCTGTG | 8760 |
| AAGTTCTTAA | AGTTTAGAGG | CTAACTTACA | GAAATGAATA | AGTTGTTTTG | TTTTATAGCC | 8820 |
| CGGTAGAGGA | GTTAACCCCA | AAGGTGATAT | GGTTTTATTT | CCTGTTATGT | TTAACTTGAT | 8880 |
| AATCTTATTT | TGGCATTCTT | TTCCCATTGA | CTATATACAT | CTCTATTTCT | CAAATGTTCA | 8940 |
| TGGAACTAGC | TCTTTTATTT | TCCTGCTGGT | TTCTTCAGTA | ATGAGTTAAA | TAAAACATTG | 9000 |
| ACACATACA | | | | | | 9009 |

( 2 ) INFORMATION FOR SEQ ID NO:2:

( i ) SEQUENCE CHARACTERISTICS:
        ( A ) LENGTH: 2332 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
        ( A ) ORGANISM: Homo sapien
        ( F ) TISSUE TYPE: Liver cDNA sequence ( x i ) SEQUENCE DESCRIPTION: SEQ ID NO:2:

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Val His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                     85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
        130                 135                 140

Gly Pro Met Ala Ser Asp Pro Leu Cys Leu Thr Tyr Ser Tyr Leu Ser
145                 150                 155                 160
```

```
His  Val  Asp  Leu  Val  Lys  Asp  Leu  Asn  Ser  Gly  Leu  Ile  Gly  Ala  Leu
               165                 170                      175

Leu  Val  Cys  Arg  Glu  Gly  Ser  Leu  Ala  Lys  Glu  Lys  Thr  Gln  Thr  Leu
               180                 185                      190

His  Lys  Phe  Ile  Leu  Leu  Phe  Ala  Val  Phe  Asp  Glu  Gly  Lys  Ser  Trp
          195                      200                 205

His  Ser  Glu  Thr  Lys  Asn  Ser  Leu  Met  Gln  Asp  Arg  Asp  Ala  Ala  Ser
     210                      215                 220

Ala  Arg  Ala  Trp  Pro  Lys  Met  His  Thr  Val  Asn  Gly  Tyr  Val  Asn  Arg
225                      230                 235                           240

Ser  Leu  Pro  Gly  Leu  Ile  Gly  Cys  His  Arg  Lys  Ser  Val  Tyr  Trp  His
               245                      250                      255

Val  Ile  Gly  Met  Gly  Thr  Thr  Pro  Glu  Val  His  Ser  Ile  Phe  Leu  Glu
               260                 265                      270

Gly  His  Thr  Phe  Leu  Val  Arg  Asn  His  Arg  Gln  Ala  Ser  Leu  Glu  Ile
          275                      280                 285

Ser  Pro  Ile  Thr  Phe  Leu  Thr  Ala  Gln  Thr  Leu  Leu  Met  Asp  Leu  Gly
     290                      295                 300

Gln  Phe  Leu  Leu  Phe  Cys  His  Ile  Ser  Ser  His  Gln  His  Asp  Gly  Met
305                      310                 315                           320

Glu  Ala  Tyr  Val  Lys  Val  Asp  Ser  Cys  Pro  Glu  Glu  Pro  Gln  Leu  Arg
               325                      330                      335

Met  Lys  Asn  Asn  Glu  Glu  Ala  Glu  Asp  Tyr  Asp  Asp  Asp  Leu  Thr  Asp
               340                      345                 350

Ser  Glu  Met  Asp  Val  Val  Arg  Phe  Asp  Asp  Asp  Asn  Ser  Pro  Ser  Phe
          355                      360                 365

Ile  Gln  Ile  Arg  Ser  Val  Ala  Lys  Lys  His  Pro  Lys  Thr  Trp  Val  His
     370                      375                 380

Tyr  Ile  Ala  Ala  Glu  Glu  Glu  Asp  Trp  Asp  Tyr  Ala  Pro  Leu  Val  Leu
385                      390                 395                           400

Ala  Pro  Asp  Asp  Arg  Ser  Tyr  Lys  Ser  Gln  Tyr  Leu  Asn  Asn  Gly  Pro
               405                      410                      415

Gln  Arg  Ile  Gly  Arg  Lys  Tyr  Lys  Lys  Val  Arg  Phe  Met  Ala  Tyr  Thr
               420                      425                 430

Asp  Glu  Thr  Phe  Lys  Thr  Arg  Glu  Ala  Ile  Gln  His  Glu  Ser  Gly  Ile
          435                      440                 445

Leu  Gly  Pro  Leu  Leu  Tyr  Gly  Glu  Val  Gly  Asp  Thr  Leu  Leu  Ile  Ile
     450                      455                 460

Phe  Lys  Asn  Gln  Ala  Ser  Arg  Pro  Tyr  Asn  Ile  Tyr  Pro  His  Gly  Ile
465                      470                 475                           480

Thr  Asp  Val  Arg  Pro  Leu  Tyr  Ser  Arg  Arg  Leu  Pro  Lys  Gly  Val  Lys
               485                      490                      495

His  Leu  Lys  Asp  Phe  Pro  Ile  Leu  Pro  Gly  Glu  Ile  Phe  Lys  Tyr  Lys
               500                      505                      510

Trp  Thr  Val  Thr  Val  Glu  Asp  Gly  Pro  Thr  Lys  Ser  Asp  Pro  Arg  Cys
          515                      520                 525

Leu  Thr  Arg  Tyr  Tyr  Ser  Ser  Phe  Val  Asn  Met  Glu  Arg  Asp  Leu  Ala
     530                      535                 540

Ser  Gly  Leu  Ile  Gly  Pro  Leu  Leu  Ile  Cys  Tyr  Lys  Glu  Ser  Val  Asp
545                      550                 555                           560

Gln  Arg  Gly  Asn  Gln  Ile  Met  Ser  Asp  Lys  Arg  Asn  Val  Ile  Leu  Phe
               565                      570                      575

Ser  Val  Phe  Asp  Glu  Asn  Arg  Ser  Trp  Tyr  Leu  Thr  Glu  Asn  Ile  Gln
```

-continued

|     |     |     |     |     | 580 |     |     |     |     | 585 |     |     |     |     | 590 |     |     |
|-----|-----|-----|-----|-----|-----|-----|-----|-----|-----|-----|-----|-----|-----|-----|-----|-----|-----|
| Arg | Phe | Leu | Pro | Asn | Pro | Ala | Gly | Val | Gln | Leu | Glu | Asp | Pro | Glu | Phe |
|     |     | 595 |     |     |     |     | 600 |     |     |     |     | 605 |     |     |     |
| Gln | Ala | Ser | Asn | Ile | Met | His | Ser | Ile | Asn | Gly | Tyr | Val | Phe | Asp | Ser |
|     |     | 610 |     |     |     | 615 |     |     |     |     | 620 |     |     |     |     |
| Leu | Gln | Leu | Ser | Val | Cys | Leu | His | Glu | Val | Ala | Tyr | Trp | Tyr | Ile | Leu |
| 625 |     |     |     |     | 630 |     |     |     |     | 635 |     |     |     |     | 640 |
| Ser | Ile | Gly | Ala | Gln | Thr | Asp | Phe | Leu | Ser | Val | Phe | Phe | Ser | Gly | Tyr |
|     |     |     |     | 645 |     |     |     |     | 650 |     |     |     |     | 655 |     |
| Thr | Phe | Lys | His | Lys | Met | Val | Tyr | Glu | Asp | Thr | Leu | Thr | Leu | Phe | Pro |
|     |     |     | 660 |     |     |     |     | 665 |     |     |     |     | 670 |     |     |
| Phe | Ser | Gly | Glu | Thr | Val | Phe | Met | Ser | Met | Glu | Asn | Pro | Gly | Leu | Trp |
|     |     | 675 |     |     |     |     | 680 |     |     |     |     | 685 |     |     |     |
| Ile | Leu | Gly | Cys | His | Asn | Ser | Asp | Phe | Arg | Asn | Arg | Gly | Met | Thr | Ala |
|     |     | 690 |     |     |     | 695 |     |     |     |     | 700 |     |     |     |     |
| Leu | Leu | Lys | Val | Ser | Ser | Cys | Asp | Lys | Asn | Thr | Gly | Asp | Tyr | Tyr | Glu |
| 705 |     |     |     |     | 710 |     |     |     |     | 715 |     |     |     |     | 720 |
| Asp | Ser | Tyr | Glu | Asp | Ile | Ser | Ala | Tyr | Leu | Leu | Ser | Lys | Asn | Asn | Ala |
|     |     |     |     | 725 |     |     |     |     | 730 |     |     |     |     | 735 |     |
| Ile | Glu | Pro | Arg | Ser | Phe | Ser | Gln | Asn | Ser | Arg | His | Pro | Ser | Thr | Arg |
|     |     |     | 740 |     |     |     |     | 745 |     |     |     |     | 750 |     |     |
| Gln | Lys | Gln | Phe | Asn | Ala | Thr | Thr | Ile | Pro | Glu | Asn | Asp | Ile | Glu | Lys |
|     |     | 755 |     |     |     |     | 760 |     |     |     |     | 765 |     |     |     |
| Thr | Asp | Pro | Trp | Phe | Ala | His | Arg | Thr | Pro | Met | Pro | Lys | Ile | Gln | Asn |
|     | 770 |     |     |     |     | 775 |     |     |     |     | 780 |     |     |     |     |
| Val | Ser | Ser | Ser | Asp | Leu | Leu | Met | Leu | Leu | Arg | Gln | Ser | Pro | Thr | Pro |
| 785 |     |     |     |     | 790 |     |     |     |     | 795 |     |     |     |     | 800 |
| His | Gly | Leu | Ser | Leu | Ser | Asp | Leu | Gln | Glu | Ala | Lys | Tyr | Glu | Thr | Phe |
|     |     |     |     | 805 |     |     |     |     | 810 |     |     |     |     | 815 |     |
| Ser | Asp | Asp | Pro | Ser | Pro | Gly | Ala | Ile | Asp | Ser | Asn | Asn | Ser | Leu | Ser |
|     |     |     | 820 |     |     |     |     | 825 |     |     |     |     | 830 |     |     |
| Glu | Met | Thr | His | Phe | Arg | Pro | Gln | Leu | His | His | Ser | Gly | Asp | Met | Val |
|     |     | 835 |     |     |     |     | 840 |     |     |     |     | 845 |     |     |     |
| Phe | Thr | Pro | Glu | Ser | Gly | Leu | Gln | Leu | Arg | Leu | Asn | Glu | Lys | Leu | Gly |
|     | 850 |     |     |     |     | 855 |     |     |     |     | 860 |     |     |     |     |
| Thr | Thr | Ala | Ala | Thr | Glu | Leu | Lys | Lys | Leu | Asp | Phe | Lys | Val | Ser | Ser |
| 865 |     |     |     |     | 870 |     |     |     |     | 875 |     |     |     |     | 880 |
| Thr | Ser | Asn | Asn | Leu | Ile | Ser | Thr | Ile | Pro | Ser | Asp | Asn | Leu | Ala | Ala |
|     |     |     |     | 885 |     |     |     |     | 890 |     |     |     |     | 895 |     |
| Gly | Thr | Asp | Asn | Thr | Ser | Ser | Leu | Gly | Pro | Pro | Ser | Met | Pro | Val | His |
|     |     |     | 900 |     |     |     |     | 905 |     |     |     |     | 910 |     |     |
| Tyr | Asp | Ser | Gln | Leu | Asp | Thr | Thr | Leu | Phe | Gly | Lys | Lys | Ser | Ser | Pro |
|     |     | 915 |     |     |     |     | 920 |     |     |     |     | 925 |     |     |     |
| Leu | Thr | Glu | Ser | Gly | Gly | Pro | Leu | Ser | Leu | Ser | Glu | Glu | Asn | Asn | Asp |
|     | 930 |     |     |     |     | 935 |     |     |     |     | 940 |     |     |     |     |
| Ser | Lys | Leu | Leu | Glu | Ser | Gly | Leu | Met | Asn | Ser | Gln | Glu | Ser | Ser | Trp |
| 945 |     |     |     |     | 950 |     |     |     |     | 955 |     |     |     |     | 960 |
| Gly | Lys | Asn | Val | Ser | Ser | Thr | Glu | Ser | Gly | Arg | Leu | Phe | Lys | Gly | Lys |
|     |     |     |     | 965 |     |     |     |     | 970 |     |     |     |     | 975 |     |
| Arg | Ala | His | Gly | Pro | Ala | Leu | Leu | Thr | Lys | Asp | Asn | Ala | Leu | Phe | Lys |
|     |     |     | 980 |     |     |     |     | 985 |     |     |     |     | 990 |     |     |
| Val | Ser | Ile | Ser | Leu | Leu | Lys | Thr | Asn | Lys | Thr | Ser | Asn | Asn | Ser | Ala |
|     |     | 995 |     |     |     |     | 1000|     |     |     |     | 1005|     |     |     |

```
Thr Asn Arg Lys Thr His Ile Asp Gly Pro Ser Leu Leu Ile Glu Asn
    1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
            1045                1050                1055

Thr Ala Leu Arg Leu Asn His Met Ser Asn Lys Thr Thr Ser Ser Lys
            1060                1065                1070

Asn Met Glu Met Val Gln Gln Lys Lys Glu Gly Pro Ile Pro Pro Asp
    1075                1080                1085

Ala Gln Asn Pro Asp Met Ser Phe Phe Lys Met Leu Phe Leu Pro Glu
    1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
            1125                1130                1135

Ser Val Glu Gly Gln Asn Phe Leu Ser Glu Lys Asn Lys Val Val Val
            1140                1145                1150

Gly Lys Gly Glu Phe Thr Lys Asp Val Gly Leu Lys Glu Met Val Phe
            1155                1160                1165

Pro Ser Ser Arg Asn Leu Phe Leu Thr Asn Leu Asp Asn Leu His Glu
            1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
            1205                1210                1215

Val Thr Gly Thr Lys Asn Phe Met Lys Asn Leu Phe Leu Leu Ser Thr
            1220                1225                1230

Arg Gln Asn Val Glu Gly Ser Tyr Glu Gly Ala Tyr Ala Pro Val Leu
    1235                1240                1245

Gln Asp Phe Arg Ser Leu Asn Asp Ser Thr Asn Arg Thr Lys Lys His
            1250                1255                1260

Thr Ala His Phe Ser Lys Lys Gly Glu Glu Glu Asn Leu Glu Gly Leu
1265                1270                1275                1280

Gly Asn Gln Thr Lys Gln Ile Val Glu Lys Tyr Ala Cys Thr Thr Arg
            1285                1290                1295

Ile Ser Pro Asn Thr Ser Gln Gln Asn Phe Val Thr Gln Arg Ser Lys
            1300                1305                1310

Arg Ala Leu Lys Gln Phe Arg Leu Pro Leu Glu Glu Thr Glu Leu Glu
            1315                1320                1325

Lys Arg Ile Ile Val Asp Asp Thr Ser Thr Gln Trp Ser Lys Asn Met
            1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
            1365                1370                1375

Ser His Ser Ile Pro Gln Ala Asn Arg Ser Pro Leu Pro Ile Ala Lys
            1380                1385                1390

Val Ser Ser Phe Pro Ser Ile Arg Pro Ile Tyr Leu Thr Arg Val Leu
            1395                1400                1405

Phe Gln Asp Asn Ser Ser His Leu Pro Ala Ala Ser Tyr Arg Lys Lys
    1410                1415                1420

Asp Ser Gly Val Gln Glu Ser Ser His Phe Leu Gln Gly Ala Lys Lys
1425                1430                1435                1440
```

| | | | | | | | | | | | | | |
|---|---|---|---|---|---|---|---|---|---|---|---|---|---|
|Asn|Asn|Leu|Ser|Leu|Ala|Ile|Leu|Thr|Leu|Glu|Met|Thr|Gly|Asp|Gln|
| | | | |1445| | | | |1450| | | | |1455| |
|Arg|Glu|Val|Gly|Ser|Leu|Gly|Thr|Ser|Ala|Thr|Asn|Ser|Val|Thr|Tyr|
| | | |1460| | | | |1465| | | | |1470| | |
|Lys|Lys|Val|Glu|Asn|Thr|Val|Leu|Pro|Lys|Pro|Asp|Leu|Pro|Lys|Thr|
| | |1475| | | |1480| | | | |1485| | | | |
|Ser|Gly|Lys|Val|Glu|Leu|Leu|Pro|Lys|Val|His|Ile|Tyr|Gln|Lys|Asp|
| |1490| | | | |1495| | | | |1500| | | | |
|Leu|Phe|Pro|Thr|Glu|Thr|Ser|Asn|Gly|Ser|Pro|Gly|His|Leu|Asp|Leu|
|1505| | | | |1510| | | | |1515| | | | |1520|
|Val|Glu|Gly|Ser|Leu|Leu|Gln|Gly|Thr|Glu|Gly|Ala|Ile|Lys|Trp|Asn|
| | | | |1525| | | | |1530| | | | |1535| |
|Glu|Ala|Asn|Arg|Pro|Gly|Lys|Val|Pro|Phe|Leu|Arg|Val|Ala|Thr|Glu|
| | | |1540| | | | |1545| | | | |1550| | |
|Ser|Ser|Ala|Lys|Thr|Pro|Ser|Lys|Leu|Leu|Asp|Pro|Leu|Ala|Trp|Asp|
| | |1555| | | |1560| | | | |1565| | | | |
|Asn|His|Tyr|Gly|Thr|Gln|Ile|Pro|Lys|Glu|Glu|Trp|Lys|Ser|Gln|Glu|
| |1570| | | | |1575| | | | |1580| | | | |
|Lys|Ser|Pro|Glu|Lys|Thr|Ala|Phe|Lys|Lys|Lys|Asp|Thr|Ile|Leu|Ser|
|1585| | | | |1590| | | | |1595| | | | |1600|
|Leu|Asn|Ala|Cys|Glu|Ser|Asn|His|Ala|Ile|Ala|Ala|Ile|Asn|Glu|Gly|
| | | | |1605| | | | |1610| | | | |1615| |
|Gln|Asn|Lys|Pro|Glu|Ile|Glu|Val|Thr|Trp|Ala|Lys|Gln|Gly|Arg|Thr|
| | | |1620| | | | |1625| | | | |1630| | |
|Glu|Arg|Leu|Cys|Ser|Gln|Asn|Pro|Pro|Val|Leu|Lys|Arg|His|Gln|Arg|
| | |1635| | | |1640| | | | |1645| | | | |
|Glu|Ile|Thr|Arg|Thr|Thr|Leu|Gln|Ser|Asp|Gln|Glu|Glu|Ile|Asp|Tyr|
| |1650| | | | |1655| | | | |1660| | | | |
|Asp|Asp|Thr|Ile|Ser|Val|Glu|Met|Lys|Lys|Glu|Asp|Phe|Asp|Ile|Tyr|
|1665| | | | |1670| | | | |1675| | | | |1680|
|Asp|Glu|Asp|Glu|Asn|Gln|Ser|Pro|Arg|Ser|Phe|Gln|Lys|Lys|Thr|Arg|
| | | | |1685| | | | |1690| | | | |1695| |
|His|Tyr|Phe|Ile|Ala|Ala|Val|Glu|Arg|Leu|Trp|Asp|Tyr|Gly|Met|Ser|
| | | |1700| | | | |1705| | | | |1710| | |
|Ser|Ser|Pro|His|Val|Leu|Arg|Asn|Arg|Ala|Gln|Ser|Gly|Ser|Val|Pro|
| | |1715| | | |1720| | | | |1725| | | | |
|Gln|Phe|Lys|Lys|Val|Val|Phe|Gln|Glu|Phe|Thr|Asp|Gly|Ser|Phe|Thr|
| |1730| | | | |1735| | | | |1740| | | | |
|Gln|Pro|Leu|Tyr|Arg|Gly|Glu|Leu|Asn|Glu|His|Leu|Gly|Leu|Leu|Gly|
|1745| | | | |1750| | | | |1755| | | | |1760|
|Pro|Tyr|Ile|Arg|Ala|Glu|Val|Glu|Asp|Asn|Ile|Met|Val|Thr|Phe|Arg|
| | | | |1765| | | | |1770| | | | |1775| |
|Asn|Gln|Ala|Ser|Arg|Pro|Tyr|Ser|Phe|Tyr|Ser|Ser|Leu|Ile|Ser|Tyr|
| | | |1780| | | | |1785| | | | |1790| | |
|Glu|Glu|Asp|Gln|Arg|Gln|Gly|Ala|Glu|Pro|Arg|Lys|Asn|Phe|Val|Lys|
| | |1795| | | |1800| | | | |1805| | | | |
|Pro|Asn|Glu|Thr|Lys|Thr|Tyr|Phe|Trp|Lys|Val|Gln|His|His|Met|Ala|
| |1810| | | | |1815| | | | |1820| | | | |
|Pro|Thr|Lys|Asp|Glu|Phe|Asp|Cys|Lys|Ala|Trp|Ala|Tyr|Phe|Ser|Asp|
|1825| | | | |1830| | | | |1835| | | | |1840|
|Val|Asp|Leu|Glu|Lys|Asp|Val|His|Ser|Gly|Leu|Ile|Gly|Pro|Leu|Leu|
| | | | |1845| | | | |1850| | | | |1855| |
|Val|Cys|His|Thr|Asn|Thr|Leu|Asn|Pro|Ala|His|Gly|Arg|Gln|Val|Thr|

|     |     |     |     |     |     |     |     |     |     |     |     |     |     |     |
| --- | --- | --- | --- | --- | --- | --- | --- | --- | --- | --- | --- | --- | --- | --- |
|     |     |     | 1860 |     |     |     | 1865 |     |     |     | 1870 |     |     |     |
| Val | Gln | Glu | Phe | Ala | Leu | Phe | Phe | Thr | Ile | Phe | Asp | Glu | Thr | Lys | Ser |
|     |     |     | 1875 |     |     |     | 1880 |     |     |     | 1885 |     |     |     |
| Trp | Tyr | Phe | Thr | Glu | Asn | Met | Glu | Arg | Asn | Cys | Arg | Ala | Pro | Cys | Asn |
|     |     |     | 1890 |     |     |     | 1895 |     |     |     | 1900 |     |     |     |
| Ile | Gln | Met | Glu | Asp | Pro | Thr | Phe | Lys | Glu | Asn | Tyr | Arg | Phe | His | Ala |
| 1905 |   |   |   | 1910 |   |   |   | 1915 |   |   |   |   |   |   | 1920 |
| Ile | Asn | Gly | Tyr | Ile | Met | Asp | Thr | Leu | Pro | Gly | Leu | Val | Met | Ala | Gln |
|     |     |     |     | 1925 |     |     |     | 1930 |     |     |     |     |     | 1935 |     |
| Asp | Gln | Arg | Ile | Arg | Trp | Tyr | Leu | Leu | Ser | Met | Gly | Ser | Asn | Glu | Asn |
|     |     |     |     | 1940 |     |     |     | 1945 |     |     |     | 1950 |     |     |     |
| Ile | His | Ser | Ile | His | Phe | Ser | Gly | His | Val | Phe | Thr | Val | Arg | Lys | Lys |
|     |     |     |     | 1955 |     |     |     | 1960 |     |     |     | 1965 |     |     |     |
| Glu | Glu | Tyr | Lys | Met | Ala | Leu | Tyr | Asn | Leu | Tyr | Pro | Gly | Val | Phe | Glu |
|     |     |     | 1970 |     |     |     | 1975 |     |     |     | 1980 |     |     |     |     |
| Thr | Val | Glu | Met | Leu | Pro | Ser | Lys | Ala | Gly | Ile | Trp | Arg | Val | Glu | Cys |
| 1985 |   |   |   |   | 1990 |   |   |   |   | 1995 |   |   |   |   | 2000 |
| Leu | Ile | Gly | Glu | His | Leu | His | Ala | Gly | Met | Ser | Thr | Leu | Phe | Leu | Val |
|     |     |     |     | 2005 |     |     |     | 2010 |     |     |     |     |     | 2015 |     |
| Tyr | Ser | Asn | Lys | Cys | Gln | Thr | Pro | Leu | Gly | Met | Ala | Ser | Gly | His | Ile |
|     |     |     |     | 2020 |     |     |     | 2025 |     |     |     | 2030 |     |     |     |
| Arg | Asp | Phe | Gln | Ile | Thr | Ala | Ser | Gly | Gln | Tyr | Gly | Gln | Trp | Ala | Pro |
|     |     |     | 2035 |     |     |     | 2040 |     |     |     | 2045 |     |     |     |     |
| Lys | Leu | Ala | Arg | Leu | His | Tyr | Ser | Gly | Ser | Ile | Asn | Ala | Trp | Ser | Thr |
|     |     |     | 2050 |     |     |     | 2055 |     |     |     | 2060 |     |     |     |     |
| Lys | Glu | Pro | Phe | Ser | Trp | Ile | Lys | Val | Asp | Leu | Leu | Ala | Pro | Met | Ile |
| 2065 |   |   |   |   | 2070 |   |   |   |   | 2075 |   |   |   |   | 2080 |
| Ile | His | Gly | Ile | Lys | Thr | Gln | Gly | Ala | Arg | Gln | Lys | Phe | Ser | Ser | Leu |
|     |     |     |     | 2085 |     |     |     | 2090 |     |     |     |     |     | 2095 |     |
| Tyr | Ile | Ser | Gln | Phe | Ile | Ile | Met | Tyr | Ser | Leu | Asp | Gly | Lys | Lys | Trp |
|     |     |     |     | 2100 |     |     |     | 2105 |     |     |     | 2110 |     |     |     |
| Gln | Thr | Tyr | Arg | Gly | Asn | Ser | Thr | Gly | Thr | Leu | Met | Val | Phe | Phe | Gly |
|     |     |     | 2115 |     |     |     | 2120 |     |     |     | 2125 |     |     |     |     |
| Asn | Val | Asp | Ser | Ser | Gly | Ile | Lys | His | Asn | Ile | Phe | Asn | Pro | Pro | Ile |
|     |     |     | 2130 |     |     |     | 2135 |     |     |     | 2140 |     |     |     |     |
| Ile | Ala | Arg | Tyr | Ile | Arg | Leu | His | Pro | Thr | His | Tyr | Ser | Ile | Arg | Ser |
| 2145 |   |   |   |   | 2150 |   |   |   |   | 2155 |   |   |   |   | 2160 |
| Thr | Leu | Arg | Met | Glu | Leu | Met | Gly | Cys | Asp | Leu | Asn | Ser | Cys | Ser | Met |
|     |     |     |     |     | 2165 |     |     |     |     | 2170 |     |     |     | 2175 |     |
| Pro | Leu | Gly | Met | Glu | Ser | Lys | Ala | Ile | Ser | Asp | Ala | Gln | Ile | Thr | Ala |
|     |     |     |     | 2180 |     |     |     | 2185 |     |     |     | 2190 |     |     |     |
| Ser | Ser | Tyr | Phe | Thr | Asn | Met | Phe | Ala | Thr | Trp | Ser | Pro | Ser | Lys | Ala |
|     |     |     |     | 2195 |     |     |     | 2200 |     |     |     | 2205 |     |     |     |
| Arg | Leu | His | Leu | Gln | Gly | Arg | Ser | Asn | Ala | Trp | Arg | Pro | Gln | Val | Asn |
|     |     |     |     | 2210 |     |     |     | 2215 |     |     |     | 2220 |     |     |     |
| Asn | Pro | Lys | Glu | Trp | Leu | Gln | Val | Asp | Phe | Gln | Lys | Thr | Met | Lys | Val |
| 2225 |   |   |   |   | 2230 |   |   |   |   | 2235 |   |   |   |   | 2240 |
| Thr | Gly | Val | Thr | Thr | Gln | Gly | Val | Lys | Ser | Leu | Leu | Thr | Ser | Met | Tyr |
|     |     |     |     | 2245 |     |     |     | 2250 |     |     |     |     |     | 2255 |     |
| Val | Lys | Glu | Phe | Leu | Ile | Ser | Ser | Ser | Gln | Asp | Gly | His | Gln | Trp | Thr |
|     |     |     | 2260 |     |     |     | 2265 |     |     |     | 2270 |     |     |     |     |
| Leu | Phe | Phe | Gln | Asn | Gly | Lys | Val | Lys | Val | Phe | Gln | Gly | Asn | Gln | Asp |
|     |     |     | 2275 |     |     |     | 2280 |     |     |     | 2285 |     |     |     |     |

```
Ser  Phe  Thr  Pro  Val  Val  Asn  Ser  Leu  Asp  Pro  Pro  Leu  Leu  Thr  Arg
     2290                2295                2300

Tyr  Leu  Arg  Ile  His  Pro  Gln  Ser  Trp  Val  His  Gln  Ile  Ala  Leu  Arg
     2305                2310                2315                          2320

Met  Glu  Val  Leu  Gly  Cys  Glu  Ala  Gln  Asp  Leu  Tyr
                    2325                     2330
```

( 2 ) INFORMATION FOR SEQ ID NO:3:

( i ) SEQUENCE CHARACTERISTICS:
　　　　( A ) LENGTH: 1130 base pairs
　　　　( B ) TYPE: nucleic acid
　　　　( C ) STRANDEDNESS: single
　　　　( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
　　　　( A ) ORGANISM: Porcine
　　　　( F ) TISSUE TYPE: Blood ( i x ) FEATURE:
　　　　( A ) NAME/KEY: Region
　　　　( B ) LOCATION: 1..1130
　　　　( D ) OTHER INFORMATION: /note="cDNA encoding A2
　　　　　　　　domain of porcine factor VIII."

( x i ) SEQUENCE DESCRIPTION: SEQ ID NO:3:

```
TAAGCACCCT  AAGACGTGGG  TGCACTACAT  CTCTGCAGAG  GAGGAGGACT  GGGACTACGC    60

CCCCGCGGTC  CCCAGCCCCA  GTGACAGAAG  TTATAAAAGT  CTCTACTTGA  ACAGTGGTCC   120

TCAGCGAATT  GGTAGGAAAT  ACAAAAAAGC  TCGATTCGTC  GCTTACACGG  ATGTAACATT   180

TAAGACTCGT  AAAGCTATTC  CGTATGAATC  AGGAATCCTG  GGACCTTTAC  TTTATGGAGA   240

AGTTGGAGAC  ACACTTTTGA  TTATATTTAA  GAATAAAGCG  AGCCGACCAT  ATAACATCTA   300

CCCTCATGGA  ATCACTGATG  TCAGCGCTTT  GCACCCAGGG  AGACTTCTAA  AAGGTTGGAA   360

ACATTTGAAA  GACATGCCAA  TTCTGCCAGG  AGAGACTTTC  AAGTATAAAT  GGACAGTGAC   420

TGTGGAAGAT  GGGCCAACCA  AGTCCGATCC  TCGGTGCCTG  ACCCGCTACT  ACTCGAGCTC   480

CATTAATCTA  GAGAAAGATC  TGGCTTCGGG  ACTCATTGGC  CCTCTCCTCA  TCTGCTACAA   540

AGAATCTGTA  GACCAAAGAG  GAAACCAGAT  GATGTCAGAC  AAGAGAAACG  TCATCCTGTT   600

TTCTGTATTC  GATGAGAATC  AAAGCTGGTA  CCTCGCAGAG  AATATTCAGC  GCTTCCTCCC   660

CAATCCGGAT  GGATTACAGC  CCCAGGATCC  AGAGTTCCAA  GCTTCTAACA  TCATGCACAG   720

CATCAATGGC  TATGTTTTTG  ATAGCTTGCA  GCTGTCGGTT  TGTTTGCACG  AGGTGGCATA   780

CTGGTACATT  CTAAGTGTTG  GAGCACAGAC  GGACTTCCTC  TCCGTCTTCT  TCTCTGGCTA   840

CACCTTCAAA  CACAAAATGG  TCTATGAAGA  CACACTCACC  CTGTTCCCCT  TCTCAGGAGA   900

AACGGTCTTC  ATGTCAATGG  AAAACCCAGG  TCTCTGGGTC  CTAGGGTGCC  ACAACTCAGA   960

CTTGCGGAAC  AGAGGGATGA  CAGCCTTACT  GAAGGTGTAT  AGTTGTGACA  GGGACATTGG  1020

TGATTATTAT  GACAACACTT  ATGAAGATAT  TCCAGGCTTC  TTGCTGAGTG  GAAAGAATGT  1080

CATTGAACCC  AGAAGCTTTG  CCCAGAATTC  AAGACCCCCT  AGTGCGAGCA              1130
```

( 2 ) INFORMATION FOR SEQ ID NO:4:

( i ) SEQUENCE CHARACTERISTICS:
　　　　( A ) LENGTH: 368 amino acids
　　　　( B ) TYPE: amino acid (C) STRANDEDNESS: single
(D) TOPOLOGY: linear (ii) MOLECULE TYPE: protein (iii) HYPOTHETICAL: YES (iv) ANTI-SENSE: NO (v) FRAGMENT TYPE: N-terminal (vi) ORIGINAL SOURCE:
    (A) ORGANISM: Porcine
    (F) TISSUE TYPE: Spleen (ix) FEATURE:
    (A) NAME/KEY: Protein
    (B) LOCATION: 1..368
    (D) OTHER INFORMATION: /note="Predicted amino acid
        sequence of the porcine factor VIII A2 domain,
        defined as residues homologous to human factor
        VIII amino acid sequence 373-740.
        (Residues 1-4 are from known porcine amino acid sequence.)

(xi) SEQUENCE DESCRIPTION: SEQ ID NO:4:

```
Ser Val Ala Lys Lys His Pro Lys Thr Trp Val His Tyr Ile Ser Ala
 1               5                  10                  15

Glu Glu Glu Asp Trp Asp Tyr Ala Pro Ala Val Pro Ser Pro Ser Asp
                20                  25                  30

Arg Ser Tyr Lys Ser Leu Tyr Leu Asn Ser Gly Pro Gln Arg Ile Gly
            35                  40                  45

Arg Lys Tyr Lys Lys Ala Arg Phe Val Ala Tyr Thr Asp Val Thr Phe
        50                  55                  60

Lys Thr Arg Lys Ala Ile Pro Tyr Glu Ser Gly Ile Leu Gly Pro Leu
 65                  70                  75                  80

Leu Tyr Gly Glu Val Gly Asp Thr Leu Leu Ile Ile Phe Lys Asn Lys
                85                  90                  95

Ala Ser Arg Pro Tyr Asn Ile Tyr Pro His Gly Ile Thr Asp Val Ser
            100                 105                 110

Ala Leu His Pro Gly Arg Leu Leu Lys Gly Trp Lys His Leu Lys Asp
        115                 120                 125

Met Pro Ile Leu Pro Gly Glu Thr Phe Lys Tyr Lys Trp Thr Val Thr
130                 135                 140

Val Glu Asp Gly Pro Thr Lys Ser Asp Pro Arg Cys Leu Thr Arg Tyr
145                 150                 155                 160

Tyr Ser Ser Ser Ile Asn Leu Glu Lys Asp Leu Ala Ser Gly Leu Ile
                165                 170                 175

Gly Pro Leu Leu Ile Cys Tyr Lys Glu Ser Val Asp Gln Arg Gly Asn
            180                 185                 190

Gln Met Met Ser Asp Lys Arg Asn Val Ile Leu Phe Ser Val Phe Asp
        195                 200                 205

Glu Asn Gln Ser Trp Tyr Leu Ala Glu Asn Ile Gln Arg Phe Leu Pro
210                 215                 220

Asn Pro Asp Gly Leu Gln Pro Gln Asp Pro Glu Phe Gln Ala Ser Asn
225                 230                 235                 240

Ile Met His Ser Ile Asn Gly Tyr Val Phe Asp Ser Leu Gln Leu Ser
                245                 250                 255

Val Cys Leu His Glu Val Ala Tyr Trp Tyr Ile Leu Ser Val Gly Ala
            260                 265                 270

Gln Thr Asp Phe Leu Ser Val Phe Phe Ser Gly Tyr Thr Phe Lys His
        275                 280                 285
```

| Lys | Met | Val | Tyr | Glu | Asp | Thr | Leu | Thr | Leu | Phe | Pro | Phe | Ser | Gly | Glu |
|---|---|---|---|---|---|---|---|---|---|---|---|---|---|---|---|
| | 290 | | | | | 295 | | | | | 300 | | | | |

| Thr | Val | Phe | Met | Ser | Met | Glu | Asn | Pro | Gly | Leu | Trp | Val | Leu | Gly | Cys |
|---|---|---|---|---|---|---|---|---|---|---|---|---|---|---|---|
| 305 | | | | | 310 | | | | | 315 | | | | | 320 |

| His | Asn | Ser | Asp | Leu | Arg | Asn | Arg | Gly | Met | Thr | Ala | Leu | Leu | Lys | Val |
|---|---|---|---|---|---|---|---|---|---|---|---|---|---|---|---|
| | | | | 325 | | | | | 330 | | | | | 335 | |

| Tyr | Ser | Cys | Asp | Arg | Asp | Ile | Gly | Asp | Tyr | Tyr | Asp | Asn | Thr | Tyr | Glu |
|---|---|---|---|---|---|---|---|---|---|---|---|---|---|---|---|
| | | | 340 | | | | | 345 | | | | | 350 | | |

| Asp | Ile | Pro | Gly | Phe | Leu | Leu | Ser | Gly | Lys | Asn | Val | Ile | Glu | Pro | Arg |
|---|---|---|---|---|---|---|---|---|---|---|---|---|---|---|---|
| | | 355 | | | | | 360 | | | | | 365 | | | |

( 2 ) INFORMATION FOR SEQ ID NO:5:

( i ) SEQUENCE CHARACTERISTICS:
        ( A ) LENGTH: 7493 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Mus musculus ( i x ) FEATURE:
        ( A ) NAME/KEY: repeat_unit
        ( B ) LOCATION: 1..407
        ( D ) OTHER INFORMATION: /rpt_type="terminal"
            / note="5'UTR"

( i x ) FEATURE:
        ( A ) NAME/KEY: misc_feature
        ( B ) LOCATION: 7471..7476
        ( D ) OTHER INFORMATION: /function="PolyA_signal"

( i x ) FEATURE:
        ( A ) NAME/KEY: repeat_unit
        ( B ) LOCATION: 7368..7493
        ( D ) OTHER INFORMATION: /rpt_type="terminal"
            / note="3'UTR"

( i x ) FEATURE:
        ( A ) NAME/KEY: misc_feature
        ( B ) LOCATION: 408..7367
        ( D ) OTHER INFORMATION: /product="Coagulation Factor VIII"

( x ) PUBLICATION INFORMATION:
        ( A ) AUTHORS: Elder, F.
            Lakich, D.
            Gitschier, J.
        ( B ) TITLE: Sequence of the Murine Factor VIII cDNA.
        ( C ) JOURNAL: Genomics
        ( D ) VOLUME: 16
        ( F ) PAGES: 374-379
        ( G ) DATE: 1993
        ( K ) RELEVANT RESIDUES IN SEQ ID NO:5: FROM 1 TO 7476

( x i ) SEQUENCE DESCRIPTION: SEQ ID NO:5:

```
TCTAGAGTTT  CTTTGCTACA  GGTACCAAGG  AACAGTCTTT  TAGAATAGGC  TAGGAATTTA      60

AATACACCTG  AACGCCCCTC  CTCAGTATTC  TGTTCCTTTT  CTTAAGGATT  CAAACTTGTT     120

AGGATGCACC  CAGCAGGAAA  TGGGTTAAGC  CTTAGCTCAG  CCACTCTTCC  TATTCCAGTT     180

TTCCTGTGCC  TGCTTCCTAC  TACCCAAAAG  GAAGTAATCC  TTCAGATCTG  TTTTGTGCTA     240

ATGCTACTTT  CACTCACAGT  AGATAAACTT  CCAGAAAATC  CTCTGCAAAA  TATTTAGGAC     300

TTTTACTAA  ATCATTACAT  TTCTTTTGT  TCTTAAAAGC  TAAAGTTATT  TTAGAGAAGA      360
```

| | | | | | |
|---|---|---|---|---|---|
| GTTAAATTTT | CATTTCTTTA | GTTGAACATT | TTCTAGTAAT | AAAAGCCATG | CAAATAGCAC | 420 |
| TCTTCGCTTG | CTTCTTTCTG | AGCCTTTTCA | ATTTCTGCTC | TAGTGCCATC | AGAAGATACT | 480 |
| ACCTTGGTGC | AGTGGAATTG | TCCTGGAACT | ATATTCAGAG | TGATCTGCTC | AGTGTGCTGC | 540 |
| ATACAGACTC | AAGATTTCTT | CCTAGAATGT | CAACATCTTT | TCCATTCAAC | ACCTCCATCA | 600 |
| TGTATAAAAA | GACTGTGTTT | GTAGAGTACA | AGGACCAGCT | TTTCAACATT | GCCAAGCCCA | 660 |
| GGCCACCCTG | GATGGGTTTG | CTAGGTCCTA | CCATTTGGAC | TGAGGTTCAT | GACACAGTGG | 720 |
| TCATTACACT | TAAAAACATG | GCTTCTCATC | CTGTCAGTCT | TCATGCTGTT | GGTGTGTCCT | 780 |
| ACTGGAAAGC | TTCTGAGGGA | GATGAATATG | AAGATCAGAC | AAGCCAAATG | GAGAAGGAAG | 840 |
| ATGATAAAGT | TTTCCCTGGT | GAAAGTCATA | CTTATGTTTG | GCAAGTCCTG | AAAGAGAATG | 900 |
| GTCCAATGGC | CTCTGACCCT | CCATGTCTCA | CTTACTCATA | TATGTCTCAT | GTGGATCTGG | 960 |
| TGAAAGATTT | GAATTCAGGC | CTCATTGGAG | CTCTGCTAGT | ATGTAAAGAA | GGCAGTCTCT | 1020 |
| CCAAAGAAAG | AACACAGATG | TTGTACCAAT | TTGTACTGCT | TTTTGCTGTA | TTTGATGAAG | 1080 |
| GGAAGAGCTG | GCACTCAGAA | ACAAACGACT | CTTATACACA | GTCTATGGAT | CTGCATCTG | 1140 |
| CTAGAGACTG | GCCTAAAATG | CACACAGTCA | ATGGCTATGT | AAACAGGTCT | CTTCCAGGTC | 1200 |
| TGATTGGATG | CCATAGGAAA | TCAGTCTACT | GGCACGTGAT | TGGAATGGGC | ACCACTCCTG | 1260 |
| AAATACACTC | AATATTCCTC | GAAGGTCACA | CATTTTTTGT | GAGGAACCAC | CGTCAAGCTT | 1320 |
| CATTGGAGAT | ATCACCAATA | ACTTTCCTTA | CTGCTCAAAC | ACTCTTGATA | GATCTTGGGC | 1380 |
| AGTTCCTACT | ATTTTGTCAT | ATCTCTTCCC | ATAAACATGA | TGGCATGGAA | GCTTATGTCA | 1440 |
| AAGTAGATAG | CTGCCCTGAG | GAATCCCAAT | GGCAAAAGAA | AATAATAAT | GAGGAAATGG | 1500 |
| AAGATTATGA | TGATGATCTT | TATTCAGAAA | TGGATATGTT | CACATTGGAT | TATGACAGCT | 1560 |
| CTCCTTTTAT | CCAAATTCGC | TCGGTTGCTA | AAAAGTACCC | TAAAACTTGG | ATACATTATA | 1620 |
| TTTCTGCTGA | GGAGGAAGAC | TGGGACTATG | CACCTTCAGT | TCCTACCTCG | GATAATGGAA | 1680 |
| GTTATAAAAG | CCAGTATCTG | AGCAATGGTC | CTCATCGGAT | TGGTAGGAAA | TATAAAAAAG | 1740 |
| TCAGATTTAT | AGCATACACA | GATGAAACCT | TTAAGACTCG | TGAAACTATT | CAGCATGAAT | 1800 |
| CAGGACTCTT | GGGACCTTTA | CTTTATGGAG | AAGTTGGAGA | CACACTGTTG | ATTATTTTA | 1860 |
| AGAATCAAGC | AAGCCGACCA | TATAACATTT | ACCCTCATGG | AATCACTGAT | GTCAGTCCTC | 1920 |
| TACATGCAAG | GAGATTGCCA | AGAGGTATAA | AGCACGTGAA | GGATTTGCCA | ATTCATCCAG | 1980 |
| GAGAGATATT | CAAGTACAAG | TGGACAGTTA | CAGTAGAAGA | TGGACCAACT | AAATCAGATC | 2040 |
| CACGGTGCCT | GACCCGCTAT | TATTCAAGTT | TCATTAACCC | TGAGAGAGAT | CTAGCTTCAG | 2100 |
| GACTGATTGG | CCCTCTTCTC | ATCTGCTACA | AAGAATCTGT | AGATCAAAGG | GGAAACCAGA | 2160 |
| TGATGTCAGA | CAAAAGAAAT | GTCATCCTGT | TTTCTATATT | TGATGAGAAC | CAAAGCTGGT | 2220 |
| ACATCACAGA | GAACATGCAA | CGCTTCCTCC | CCAATGCAGC | TAAAACACAG | CCCCAGGACC | 2280 |
| CTGGGTTCCA | GGCCTCCAAC | ATCATGCACA | GCATCAATGG | CTATGTTTTT | GATAGCTTGG | 2340 |
| AGTTGACAGT | TTGTTTGCAT | GAGGTGGCAT | ACTGGCACAT | TCTCAGTGTT | GGAGCACAGA | 2400 |
| CAGACTTCTT | ATCTATCTTC | TTCTCTGGAT | ATACTTTCAA | ACACAAAATG | GTCTATGAAG | 2460 |
| ATACACTTAC | CCTGTTCCCA | TTCTCAGGAG | AAACTGTCTT | TATGTCGATG | GAAAACCCAG | 2520 |
| GTCTATGGGT | CTTGGGGTGT | CATAATTCAG | ACTTTCGGAA | GAGAGGTATG | ACAGCATTGC | 2580 |
| TGAAAGTTTC | TAGTTGTGAC | AAGAGCACTA | GTGATTATTA | TGAAGAAATA | TATGAAGATA | 2640 |
| TTCCAACACA | GTTGGTGAAT | GAGAACAATG | TCATTGATCC | CAGAAGCTTC | TTCCAGAATA | 2700 |
| CAAATCATCC | TAATACTAGG | AAAAAGAAAT | TCAAAGATTC | CACAATTCCA | AAAAATGATA | 2760 |

| | | | | | |
|---|---|---|---|---|---|
| TGGAGAAGAT | TGAGCCTCAG | TTTGAAGAGA | TAGCAGAGAT | GCTTAAAGTA | CAGAGTGTCT | 2820 |
| CAGTTAGTGA | CATGTTGATG | CTCTTGGGAC | AGAGTCATCC | TACTCCACAT | GGCTTATTTT | 2880 |
| TATCAGATGG | CCAAGAAGCC | ATCTATGAGG | CTATTCATGA | TGATCATTCA | CCAAATGCAA | 2940 |
| TAGACAGCAA | TGAAGGCCCA | TCTAAAGTGA | CCCAACTCAG | GCCAGAATCC | CATCACAGTG | 3000 |
| AGAAAATAGT | ATTTACTCCT | CAGCCCGGCC | TCCAGTTAAG | ATCCAATAAA | AGTTTGGAGA | 3060 |
| CAACTATAGA | AGTAAAGTGG | AAGAAACTTG | GTTTGCAAGT | TTCTAGTTTG | CCAAGTAATC | 3120 |
| TAATGACTAC | AACAATTCTG | TCAGACAATT | TGAAAGCAAC | TTTTGAAAAG | ACAGATTCTT | 3180 |
| CAGGATTTCC | AGATATGCCA | GTTCACTCTA | GTAGTAAATT | AAGTACTACT | GCATTTGGTA | 3240 |
| AGAAAGCATA | TTCCCTTGTT | GGGTCTCATG | TACCTTTAAA | CGCGAGTGAA | GAAATAGTG | 3300 |
| ATTCCAACAT | ATTGGATTCA | ACTTTAATGT | ATAGTCAAGA | AAGTTTACCA | AGAGATAATA | 3360 |
| TATTATCAAT | AGAGAATGAT | AGATTACTCA | GAGAGAAGAG | GTTTCATGGA | ATTGCTTTAT | 3420 |
| TGACCAAAGA | TAATACTTTA | TTCAAGACA | ATGTCTCCTT | AATGAAAACA | AACAAAACAT | 3480 |
| ATAATCATTC | AACAACTAAT | GAAAACTAC | ACACTGAGAG | CCCAACATCA | ATTGAGAATA | 3540 |
| GTACAACAGA | CTTGCAAGAT | GCCATATTAA | AGGTCAATAG | TGAGATTCAA | GAAGTAACAG | 3600 |
| CTTTGATTCA | TGATGGAACA | CTTTTAGGCA | AAAATTCTAC | ATATTTGAGA | CTAAACCATA | 3660 |
| TGCTAAATAG | AACTACCTCA | ACAAAAATA | AAGACATATT | TCATAGAAAA | GATGAAGATC | 3720 |
| CTATTCCACA | AGATGAAGAG | AATACAATCA | TGCCATTTTC | CAAGATGTTG | TTCTTGTCAG | 3780 |
| AATCTTCAAA | TTGGTTTAAA | AAGACCAATG | GAAATAATTC | CTTGAACTCT | GAGCAAGAAC | 3840 |
| ATAGTCCAAA | GCAATTAGTA | TATTTAATGT | TTAAAAAATA | TGTAAAAAAT | CAAAGTTTCT | 3900 |
| TGTCAGAGAA | AAATAAAGTC | ACAGTAGAAC | AGGATGGATT | TACAAAGAAC | ATAGGACTTA | 3960 |
| AAGACATGGC | TTTTCCACAT | AATATGAGCA | TATTTCTTAC | CACTTTGTCT | AACGTACATG | 4020 |
| AAAATGGTAG | GCACAATCAA | GAAAAAATA | TTCAGGAAGA | GATAGAGAAG | GAAGCACTAA | 4080 |
| TTGAAGAGAA | AGTAGTTTTG | CCCCAGGTGC | ACGAAGCAAC | TGGCTCTAAG | AATTTCTTGA | 4140 |
| AAGACATATT | GATACTAGGC | ACTAGGCAAA | ATATAAGTTT | ATATGAAGTA | CATGTACCAG | 4200 |
| TACTTCAAAA | CATCACATCA | ATAAACAATT | CAACAAATAC | AGTACAGATT | CACATGGAGC | 4260 |
| ATTTCTTTAA | AAGAAGGAAG | GACAAGGAAA | CAAATTCAGA | AGGCTTGGTA | AATAAAACCA | 4320 |
| GAGAAATGGT | AAAAAACTAT | CCAAGCCAGA | AGAATATTAC | TACTCAACGT | AGTAAACGGG | 4380 |
| CTTTGGGACA | ATTCAGACTG | TCAACTCAAT | GGCTTAAAAC | CATAAACTGT | TCAACACAGT | 4440 |
| GTATCATTAA | ACAGATAGAC | CACAGCAAGG | AAATGAAAAA | GTTCATTACT | AAATCTTCCT | 4500 |
| TATCAGATTC | TTCTGTGATT | AAAAGCACCA | CTCAGACAAA | TAGTTCTGAC | TCACACATTG | 4560 |
| TAAAAACATC | AGCATTTCCA | CCAATAGATC | TCAAAAGGAG | TCCATTCCAA | AACAAATTTT | 4620 |
| CTCATGTTCA | AGCATCATCC | TACATTTATG | ACTTAAGAC | AAAAAGTTCA | AGAATTCAAG | 4680 |
| AAAGCAATAA | TTTCTTAAAA | GAAACCAAAA | TAAATAACCC | TTCTTTAGCC | ATTCTACCAT | 4740 |
| GGAATATGTT | CATAGATCAA | GGAAAATTTA | CCTCCCCAGG | GAAAAGTAAC | ACAAACTCAG | 4800 |
| TCACATATAA | GAAACGTGAG | AACATTATTT | TCTTGAAACC | AACTTTGCCT | GAAGAATCTG | 4860 |
| GCAAAATTGA | ATTGCTTCCT | CAAGTTTCCA | TTCAAGAGGA | AGAAATTTTA | CCTACAGAAA | 4920 |
| CTAGCCATGG | ATCTCCTGGA | CACTTGAATC | TCATGAAAGA | GGTCTTTCTT | CAGAAAATAC | 4980 |
| AGGGGCCTAC | TAAATGGAAT | AAAGCAAAGA | GGCATGGAGA | AGTATAAAA | GGTAAAACAG | 5040 |
| AGAGCTCTAA | AAATACTCGC | TCAAAACTGC | TAAATCATCA | TGCTTGGGAT | TATCATTATG | 5100 |
| CTGCACAGAT | ACCAAAAGAT | ATGTGGAAAT | CCAAAGAGAA | GTCACCAGAA | ATTATATCCA | 5160 |

```
TTAAGCAAGA GGACACCATT TTGTCTCTGA GGCCTCATGG AAACAGTCAT TCAATAGGGG      5220
CAAATGAGAA ACAAAATTGG CCTCAAAGAG AAACCACTTG GGTAAAGCAA GGCCAAACTC      5280
AAAGGACATG CTCTCAAATC CCACCAGTGT TGAAACGACA TCAAAGGGAA CTTAGTGCTT      5340
TTCAATCAGA ACAAGAAGCA ACTGACTATG ATGATGCCAT CACCATTGAA ACAATCGAGG      5400
ATTTTGACAT TTACAGTGAG GACATAAAGC AAGGTCCCCG CAGCTTTCAA CAGAAAACAA      5460
GGCACTATTT TATTGCAGCT GTGGAACGAC TCTGGGACTA TGGGATGAGT ACATCTCATG      5520
TTCTACGAAA TAGGTATCAA AGTGACAATG TACCTCAGTT CAAGAAAGTA GTTTTCCAGG      5580
AATTTACTGA TGGCTCCTTT AGTCAGCCCT TATATCGTGG AGAATTAAAT GAACACCTGG      5640
GGTTGTTGGG CCCATATATA AGAGCAGAAG TTGAAGACAA CATTATGGTA ACTTTCAAAA      5700
ACCAGGCCTC CCGTCCCTAC TCCTTCTATT CTAGCCTCAT TTCTTATAAA GAAGATCAGA      5760
GAGGAGAAGA ACCTAGAAGA AACTTTGTCA AGCCTAATGA AACCAAAATT TATTTTTGGA      5820
AAGTACAACA TCATATGGCA CCCACAGAAG ATGAGTTTGA CTGCAAGGCC TGGGCTTATT      5880
TCTCTGATGT TGATCTTGAA AGAGATATGC ACTCGGGATT AATTGGACCC CTTCTGATTT      5940
GCCACGCGAA CACACTGAAT CCTGCTCATG GGAGACAAGT GTCAGTACAG GAATTTGCTC      6000
TGCTTTTCAC TATCTTTGAT GAGACCAAGA GCTGGTACTT CACTGAAAAC GTGAAAAGGA      6060
ACTGCAAGAC ACCCTGCAAT TTCCAGATGG AAGACCCCAC TTTGAAAGAG AATTATCGCT      6120
TCCATGCAAT CAATGGTTAT GTAATGGATA CCCTACCAGG CTTAGTAATG GCTCAAGATC      6180
AAAGGATTCG ATGGTATCTT CTCAGCATGG GCAACAATGA GAACATCCAA TCTATTCATT      6240
TCAGTGGACA TGTTTTCACT GTACGGAAAA AAGAGGAGTA TAAAATGGCA GTGTACAACC      6300
TCTACCCAGG TGTTTTTGAG ACTCTGGAAA TGATACCATC CAGAGCTGGA ATATGGCGAG      6360
TAGAATGCCT TATTGGCGAG CACTTACAGG CTGGGATGAG CACTCTTTTT CTGGTGTACA      6420
GCAAGCAGTG TCAGATTCCT CTTGGAATGG CTTCTGGAAG CATCCGTGAT TTCCAGATTA      6480
CAGCTTCAGG ACATTATGGA CAGTGGGCCC CAAACCTGGC AAGACTTCAT TATTCCGGAT      6540
CAATCAATGC CTGGAGTACC AAGGAGCCCT TTCTTGGAT CAAGGTAGAT CTGTTGGCAC       6600
CAATGATTGT TCATGGCATC AAGACTCAGG GTGCTCGTCA GAAATTTTCC AGCCTTTATA      6660
TCTCTCAATT TATCATCATG TATAGCCTGG ATGGGAAGAA GTGGCTGAGT TATCAAGGAA      6720
ATTCCACTGG AACCTTAATG GTTTTCTTTG GCAATGTGGA CTCATCTGGG ATTAAGCATA      6780
ATAGTTTTAA TCCTCCAATT ATTGCTCGAT ATATCCGTTT GCACCCCACT CATTCTAGCA      6840
TCCGTAGTAC TCTTCGCATG GAGTTGATGG GCTGTGATTT AAACAGTTGC AGCATACCAT      6900
TGGGAATGGA AAGTAAAGTA ATATCAGATA CACAAATCAC TGCCTCATCC TACTTCACCA      6960
ACATGTTTGC TACTTGGTCT CCTTCACAAG CTCGACTTCA CCTCCAGGGA AGGACTAATG      7020
CCTGGCGACC TCAGGTGAAT GATCCAAAAC AATGGTTGCA AGTGGACTTA CAAAAGACAA      7080
TGAAAGTCAC TGGAATAATA ACCCAGGGAG TGAAATCTCT CTTTACCAGC ATGTTTGTGA      7140
AAGAGTTCCT TATTTCCAGC AGTCAAGATG GCCATCACTG GACTCAAATT TTATACAATG      7200
GCAAGGTAAA GGTTTTTCAG GGGAATCAGG ACTCATCCAC ACCTATGATG AATTCTCTAG      7260
ACCCACCATT ACTCACTCGC TATCTTCGAA TTCACCCCCA GATCTGGGAG CACCAAATTG      7320
CTCTGAGGCT TGAGATTCTA GGATGTGAGG CCCAGCAGCA ATACTGAGGT AGCCTCTGCA      7380
TCACCTGCTT ATTCCCCTTC CTCAGCTCAA AGATTGTCTT AATGTTTTAT TGCTGTGAAG      7440
AGACACTATG ACCATGGCAA CTCTTTATAA AATAAAGCAT TTAATCAGGG CTT            7493
```

( 2 ) INFORMATION FOR SEQ ID NO:6:

(i) SEQUENCE CHARACTERISTICS:
    (A) LENGTH: 2319 amino acids
    (B) TYPE: amino acid
    (C) STRANDEDNESS: single
    (D) TOPOLOGY: linear (ii) MOLECULE TYPE: protein (iii) HYPOTHETICAL: YES (iv) ANTI-SENSE: NO (v) FRAGMENT TYPE: N-terminal (vi) ORIGINAL SOURCE:
    (A) ORGANISM: Mus musculus (x) PUBLICATION INFORMATION:
    (A) AUTHORS: Elder, F.
        Lakich, D.
        Gitschier, J.
    (B) TITLE: Sequence of the Murine Factor VIII cDNA.
    (C) JOURNAL: Genomics
    (D) VOLUME: 16
    (F) PAGES: 374-379
    (G) DATE: 1993
    (K) RELEVANT RESIDUES IN SEQ ID NO:6: FROM 1 TO 2319

(xi) SEQUENCE DESCRIPTION: SEQ ID NO:6:

```
Met Gln Ile Ala Leu Phe Ala Cys Phe Phe Leu Ser Leu Phe Asn Phe
1               5                   10                  15

Cys Ser Ser Ala Ile Arg Arg Tyr Tyr Leu Gly Ala Val Glu Leu Ser
                20              25                  30

Trp Asn Tyr Ile Gln Ser Asp Leu Leu Ser Val Leu His Thr Asp Ser
            35              40                  45

Arg Phe Leu Pro Arg Met Ser Thr Ser Phe Pro Phe Asn Thr Ser Ile
    50              55                  60

Met Tyr Lys Lys Thr Val Phe Val Glu Tyr Lys Asp Gln Leu Phe Asn
65              70                  75                      80

Ile Ala Lys Pro Arg Pro Pro Trp Met Gly Leu Leu Gly Pro Thr Ile
                85              90                  95

Trp Thr Glu Val His Asp Thr Val Val Ile Thr Leu Lys Asn Met Ala
            100             105                 110

Ser His Pro Val Ser Leu His Ala Val Gly Val Ser Tyr Trp Lys Ala
        115             120                 125

Ser Glu Gly Asp Glu Tyr Glu Asp Gln Thr Ser Gln Met Glu Lys Glu
    130             135                 140

Asp Asp Lys Val Phe Pro Gly Glu Ser His Thr Tyr Val Trp Gln Val
145             150                 155                 160

Leu Lys Glu Asn Gly Pro Met Ala Ser Asp Pro Pro Cys Leu Thr Tyr
                165             170                 175

Ser Tyr Met Ser His Val Asp Leu Val Lys Asp Leu Asn Ser Gly Leu
            180             185                 190

Ile Gly Ala Leu Leu Val Cys Lys Glu Gly Ser Leu Ser Lys Glu Arg
        195             200                 205

Thr Gln Met Leu Tyr Gln Phe Val Leu Leu Phe Ala Val Phe Asp Glu
    210             215                 220

Gly Lys Ser Trp His Ser Glu Thr Asn Asp Ser Tyr Thr Gln Ser Met
225             230                 235                 240

Asp Ser Ala Ser Ala Arg Asp Trp Pro Lys Met His Thr Val Asn Gly
                245             250                 255

Tyr Val Asn Arg Ser Leu Pro Gly Leu Ile Gly Cys His Arg Lys Ser
```

|     |     |     |     |     |     | 260 |     |     |     |     | 265 |     |     |     |     | 270 |     |     |
|-----|-----|-----|-----|-----|-----|-----|-----|-----|-----|-----|-----|-----|-----|-----|-----|-----|-----|-----|

Val Tyr Trp His Val Ile Gly Met Gly Thr Thr Pro Glu Ile His Ser
        275                     280                 285

Ile Phe Leu Glu Gly His Thr Phe Phe Val Arg Asn His Arg Gln Ala
        290                     295                 300

Ser Leu Glu Ile Ser Pro Ile Thr Phe Leu Thr Ala Gln Thr Leu Leu
305                         310                 315                     320

Ile Asp Leu Gly Gln Phe Leu Leu Phe Cys His Ile Ser Ser His Lys
                        325                 330                     335

His Asp Gly Met Glu Ala Tyr Val Lys Val Asp Ser Cys Pro Glu Glu
                340                     345                 350

Ser Gln Trp Gln Lys Lys Asn Asn Asn Glu Glu Met Glu Asp Tyr Asp
        355                     360                 365

Asp Asp Leu Tyr Ser Glu Met Asp Met Phe Thr Leu Asp Tyr Asp Ser
        370                     375                 380

Ser Pro Phe Ile Gln Ile Arg Ser Val Ala Lys Tyr Pro Lys Thr
385                         390                 395                     400

Trp Ile His Tyr Ile Ser Ala Glu Glu Glu Asp Trp Asp Tyr Ala Pro
                405                     410                 415

Ser Val Pro Thr Ser Asp Asn Gly Ser Tyr Lys Ser Gln Tyr Leu Ser
                420                     425                 430

Asn Gly Pro His Arg Ile Gly Arg Lys Tyr Lys Lys Val Arg Phe Ile
                435                     440                 445

Ala Tyr Thr Asp Glu Thr Phe Lys Thr Arg Glu Thr Ile Gln His Glu
        450                     455                 460

Ser Gly Leu Leu Gly Pro Leu Leu Tyr Gly Glu Val Gly Asp Thr Leu
465                         470                 475                     480

Leu Ile Ile Phe Lys Asn Gln Ala Ser Arg Pro Tyr Asn Ile Tyr Pro
                485                     490                 495

His Gly Ile Thr Asp Val Ser Pro Leu His Ala Arg Arg Leu Pro Arg
                500                     505                 510

Gly Ile Lys His Val Lys Asp Leu Pro Ile His Pro Gly Glu Ile Phe
        515                     520                 525

Lys Tyr Lys Trp Thr Val Thr Val Glu Asp Gly Pro Thr Lys Ser Asp
        530                     535                 540

Pro Arg Cys Leu Thr Arg Tyr Tyr Ser Ser Phe Ile Asn Pro Glu Arg
545                         550                 555                     560

Asp Leu Ala Ser Gly Leu Ile Gly Pro Leu Leu Ile Cys Tyr Lys Glu
                565                     570                 575

Ser Val Asp Gln Arg Gly Asn Gln Met Met Ser Asp Lys Arg Asn Val
                580                     585                 590

Ile Leu Phe Ser Ile Phe Asp Glu Asn Gln Ser Trp Tyr Ile Thr Glu
        595                     600                 605

Asn Met Gln Arg Phe Leu Pro Asn Ala Ala Lys Thr Gln Pro Gln Asp
        610                     615                 620

Pro Gly Phe Gln Ala Ser Asn Ile Met His Ser Ile Asn Gly Tyr Val
625                         630                 635                     640

Phe Asp Ser Leu Glu Leu Thr Val Cys Leu His Glu Val Ala Tyr Trp
                645                     650                 655

His Ile Leu Ser Val Gly Ala Gln Thr Asp Phe Leu Ser Ile Phe Phe
                660                     665                 670

Ser Gly Tyr Thr Phe Lys His Lys Met Val Tyr Glu Asp Thr Leu Thr
        675                     680                 685

```
Leu Phe Pro Phe Ser Gly Glu Thr Val Phe Met Ser Met Glu Asn Pro
    690                 695                 700

Gly Leu Trp Val Leu Gly Cys His Asn Ser Asp Phe Arg Lys Arg Gly
705                 710                 715                 720

Met Thr Ala Leu Leu Lys Val Ser Ser Cys Asp Lys Ser Thr Ser Asp
                725                 730                 735

Tyr Tyr Glu Glu Ile Tyr Glu Asp Ile Pro Thr Gln Leu Val Asn Glu
            740                 745                 750

Asn Asn Val Ile Asp Pro Arg Ser Phe Phe Gln Asn Thr Asn His Pro
        755                 760                 765

Asn Thr Arg Lys Lys Lys Phe Lys Asp Ser Thr Ile Pro Lys Asn Asp
    770                 775                 780

Met Glu Lys Ile Glu Pro Gln Phe Glu Glu Ile Ala Glu Met Leu Lys
785                 790                 795                 800

Val Gln Ser Val Ser Val Ser Asp Met Leu Met Leu Leu Gly Gln Ser
                805                 810                 815

His Pro Thr Pro His Gly Leu Phe Leu Ser Asp Gly Gln Glu Ala Ile
            820                 825                 830

Tyr Glu Ala Ile His Asp Asp His Ser Pro Asn Ala Ile Asp Ser Asn
        835                 840                 845

Glu Gly Pro Ser Lys Val Thr Gln Leu Arg Pro Glu Ser His His Ser
    850                 855                 860

Glu Lys Ile Val Phe Thr Pro Gln Pro Gly Leu Gln Leu Arg Ser Asn
865                 870                 875                 880

Lys Ser Leu Glu Thr Thr Ile Glu Val Lys Trp Lys Lys Leu Gly Leu
                885                 890                 895

Gln Val Ser Ser Leu Pro Ser Asn Leu Met Thr Thr Thr Ile Leu Ser
            900                 905                 910

Asp Asn Leu Lys Ala Thr Phe Glu Lys Thr Asp Ser Ser Gly Phe Pro
        915                 920                 925

Asp Met Pro Val His Ser Ser Ser Lys Leu Ser Thr Thr Ala Phe Gly
    930                 935                 940

Lys Lys Ala Tyr Ser Leu Val Gly Ser His Val Pro Leu Asn Ala Ser
945                 950                 955                 960

Glu Glu Asn Ser Asp Ser Asn Ile Leu Asp Ser Thr Leu Met Tyr Ser
                965                 970                 975

Gln Glu Ser Leu Pro Arg Asp Asn Ile Leu Ser Ile Glu Asn Asp Arg
            980                 985                 990

Leu Leu Arg Glu Lys Arg Phe His Gly Ile Ala Leu Leu Thr Lys Asp
        995                 1000                1005

Asn Thr Leu Phe Lys Asp Asn Val Ser Leu Met Lys Thr Asn Lys Thr
    1010                1015                1020

Tyr Asn His Ser Thr Thr Asn Glu Lys Leu His Thr Glu Ser Pro Thr
1025                1030                1035                1040

Ser Ile Glu Asn Ser Thr Thr Asp Leu Gln Asp Ala Ile Leu Lys Val
                1045                1050                1055

Asn Ser Glu Ile Gln Glu Val Thr Ala Leu Ile His Asp Gly Thr Leu
            1060                1065                1070

Leu Gly Lys Asn Ser Thr Tyr Leu Arg Leu Asn His Met Leu Asn Arg
        1075                1080                1085

Thr Thr Ser Thr Lys Asn Lys Asp Ile Phe His Arg Lys Asp Glu Asp
    1090                1095                1100

Pro Ile Pro Gln Asp Glu Glu Asn Thr Ile Met Pro Phe Ser Lys Met
1105                1110                1115                1120
```

```
Leu Phe Leu Ser Glu Ser Ser Asn Trp Phe Lys Lys Thr Asn Gly Asn
             1125                1130                1135
Asn Ser Leu Asn Ser Glu Gln Glu His Ser Pro Lys Gln Leu Val Tyr
             1140                1145                1150
Leu Met Phe Lys Lys Tyr Val Lys Asn Gln Ser Phe Leu Ser Glu Lys
             1155                1160                1165
Asn Lys Val Thr Val Glu Gln Asp Gly Phe Thr Lys Asn Ile Gly Leu
             1170                1175                1180
Lys Asp Met Ala Phe Pro His Asn Met Ser Ile Phe Leu Thr Thr Leu
1185                 1190                1195                1200
Ser Asn Val His Glu Asn Gly Arg His Asn Gln Glu Lys Asn Ile Gln
             1205                1210                1215
Glu Glu Ile Glu Lys Glu Ala Leu Ile Glu Glu Lys Val Val Leu Pro
             1220                1225                1230
Gln Val His Glu Ala Thr Gly Ser Lys Asn Phe Leu Lys Asp Ile Leu
             1235                1240                1245
Ile Leu Gly Thr Arg Gln Asn Ile Ser Leu Tyr Glu Val His Val Pro
             1250                1255                1260
Val Leu Gln Asn Ile Thr Ser Ile Asn Asn Ser Thr Asn Thr Val Gln
1265                 1270                1275                1280
Ile His Met Glu His Phe Phe Lys Arg Arg Lys Asp Lys Glu Thr Asn
             1285                1290                1295
Ser Glu Gly Leu Val Asn Lys Thr Arg Glu Met Val Lys Asn Tyr Pro
             1300                1305                1310
Ser Gln Lys Asn Ile Thr Thr Gln Arg Ser Lys Arg Ala Leu Gly Gln
             1315                1320                1325
Phe Arg Leu Ser Thr Gln Trp Leu Lys Thr Ile Asn Cys Ser Thr Gln
             1330                1335                1340
Cys Ile Ile Lys Gln Ile Asp His Ser Lys Glu Met Lys Lys Phe Ile
1345                 1350                1355                1360
Thr Lys Ser Ser Leu Ser Asp Ser Ser Val Ile Lys Ser Thr Thr Gln
             1365                1370                1375
Thr Asn Ser Ser Asp Ser His Ile Val Lys Thr Ser Ala Phe Pro Pro
             1380                1385                1390
Ile Asp Leu Lys Arg Ser Pro Phe Gln Asn Lys Phe Ser His Val Gln
             1395                1400                1405
Ala Ser Ser Tyr Ile Tyr Asp Phe Lys Thr Lys Ser Ser Arg Ile Gln
             1410                1415                1420
Glu Ser Asn Asn Phe Leu Lys Glu Thr Lys Ile Asn Asn Pro Ser Leu
1425                 1430                1435                1440
Ala Ile Leu Pro Trp Asn Met Phe Ile Asp Gln Gly Lys Phe Thr Ser
             1445                1450                1455
Pro Gly Lys Ser Asn Thr Asn Ser Val Thr Tyr Lys Lys Arg Glu Asn
             1460                1465                1470
Ile Ile Phe Leu Lys Pro Thr Leu Pro Glu Glu Ser Gly Lys Ile Glu
             1475                1480                1485
Leu Leu Pro Gln Val Ser Ile Gln Glu Glu Glu Ile Leu Pro Thr Glu
             1490                1495                1500
Thr Ser His Gly Ser Pro Gly His Leu Asn Leu Met Lys Glu Val Phe
1505                 1510                1515                1520
Leu Gln Lys Ile Gln Gly Pro Thr Lys Trp Asn Lys Ala Lys Arg His
             1525                1530                1535
Gly Glu Ser Ile Lys Gly Lys Thr Glu Ser Ser Lys Asn Thr Arg Ser
```

|   | | | | 1540 | | | | | 1545 | | | | | 1550 |
|---|---|---|---|---|---|---|---|---|---|---|---|---|---|---|

Lys Leu Leu Asn His His Ala Trp Asp Tyr His Tyr Ala Ala Gln Ile
                1555                    1560                   1565

Pro Lys Asp Met Trp Lys Ser Lys Glu Lys Ser Pro Glu Ile Ile Ser
        1570                    1575                   1580

Ile Lys Gln Glu Asp Thr Ile Leu Ser Leu Arg Pro His Gly Asn Ser
1585                    1590                    1595                   1600

His Ser Ile Gly Ala Asn Glu Lys Gln Asn Trp Pro Gln Arg Glu Thr
                1605                    1610                   1615

Thr Trp Val Lys Gln Gly Gln Thr Gln Arg Thr Cys Ser Gln Ile Pro
        1620                    1625                   1630

Pro Val Leu Lys Arg His Gln Arg Glu Leu Ser Ala Phe Gln Ser Glu
        1635                    1640                   1645

Gln Glu Ala Thr Asp Tyr Asp Asp Ala Ile Thr Ile Glu Thr Ile Glu
        1650                    1655                   1660

Asp Phe Asp Ile Tyr Ser Glu Asp Ile Lys Gln Gly Pro Arg Ser Phe
1665                    1670                    1675                   1680

Gln Gln Lys Thr Arg His Tyr Phe Ile Ala Ala Val Glu Arg Leu Trp
                1685                    1690                   1695

Asp Tyr Gly Met Ser Thr Ser His Val Leu Arg Asn Arg Tyr Gln Ser
                1700                    1705                   1710

Asp Asn Val Pro Gln Phe Lys Lys Val Val Phe Gln Glu Phe Thr Asp
            1715                    1720                   1725

Gly Ser Phe Ser Gln Pro Leu Tyr Arg Gly Glu Leu Asn Glu His Leu
            1730                    1735                   1740

Gly Leu Leu Gly Pro Tyr Ile Arg Ala Glu Val Glu Asp Asn Ile Met
1745                    1750                    1755                   1760

Val Thr Phe Lys Asn Gln Ala Ser Arg Pro Tyr Ser Phe Tyr Ser Ser
                1765                    1770                   1775

Leu Ile Ser Tyr Lys Glu Asp Gln Arg Gly Glu Glu Pro Arg Arg Asn
                1780                    1785                   1790

Phe Val Lys Pro Asn Glu Thr Lys Ile Tyr Phe Trp Lys Val Gln His
            1795                    1800                   1805

His Met Ala Pro Thr Glu Asp Glu Phe Asp Cys Lys Ala Trp Ala Tyr
    1810                    1815                   1820

Phe Ser Asp Val Asp Leu Glu Arg Asp Met His Ser Gly Leu Ile Gly
1825                    1830                    1835                   1840

Pro Leu Leu Ile Cys His Ala Asn Thr Leu Asn Pro Ala His Gly Arg
                1845                    1850                   1855

Gln Val Ser Val Gln Glu Phe Ala Leu Leu Phe Thr Ile Phe Asp Glu
                1860                    1865                   1870

Thr Lys Ser Trp Tyr Phe Thr Glu Asn Val Lys Arg Asn Cys Lys Thr
        1875                    1880                   1885

Pro Cys Asn Phe Gln Met Glu Asp Pro Thr Leu Lys Glu Asn Tyr Arg
        1890                    1895                   1900

Phe His Ala Ile Asn Gly Tyr Val Met Asp Thr Leu Pro Gly Leu Val
1905                    1910                    1915                   1920

Met Ala Gln Asp Gln Arg Ile Arg Trp Tyr Leu Leu Ser Met Gly Asn
                1925                    1930                   1935

Asn Glu Asn Ile Gln Ser Ile His Phe Ser Gly His Val Phe Thr Val
                1940                    1945                   1950

Arg Lys Lys Glu Glu Tyr Lys Met Ala Val Tyr Asn Leu Tyr Pro Gly
                1955                    1960                   1965

-continued

```
Val Phe Glu Thr Leu Glu Met Ile Pro Ser Arg Ala Gly Ile Trp Arg
    1970                1975                1980
Val Glu Cys Leu Ile Gly Glu His Leu Gln Ala Gly Met Ser Thr Leu
1985                1990                1995                2000
Phe Leu Val Tyr Ser Lys Gln Cys Gln Ile Pro Leu Gly Met Ala Ser
                2005                2010                2015
Gly Ser Ile Arg Asp Phe Gln Ile Thr Ala Ser Gly His Tyr Gly Gln
            2020                2025                2030
Trp Ala Pro Asn Leu Ala Arg Leu His Tyr Ser Gly Ser Ile Asn Ala
        2035                2040                2045
Trp Ser Thr Lys Glu Pro Phe Ser Trp Ile Lys Val Asp Leu Leu Ala
    2050                2055                2060
Pro Met Ile Val His Gly Ile Lys Thr Gln Gly Ala Arg Gln Lys Phe
2065                2070                2075                2080
Ser Ser Leu Tyr Ile Ser Gln Phe Ile Ile Met Tyr Ser Leu Asp Gly
                2085                2090                2095
Lys Lys Trp Leu Ser Tyr Gln Gly Asn Ser Thr Gly Thr Leu Met Val
            2100                2105                2110
Phe Phe Gly Asn Val Asp Ser Ser Gly Ile Lys His Asn Ser Phe Asn
        2115                2120                2125
Pro Pro Ile Ile Ala Arg Tyr Ile Arg Leu His Pro Thr His Ser Ser
    2130                2135                2140
Ile Arg Ser Thr Leu Arg Met Glu Leu Met Gly Cys Asp Leu Asn Ser
2145                2150                2155                2160
Cys Ser Ile Pro Leu Gly Met Glu Ser Lys Val Ile Ser Asp Thr Gln
                2165                2170                2175
Ile Thr Ala Ser Ser Tyr Phe Thr Asn Met Phe Ala Thr Trp Ser Pro
            2180                2185                2190
Ser Gln Ala Arg Leu His Leu Gln Gly Arg Thr Asn Ala Trp Arg Pro
        2195                2200                2205
Gln Val Asn Asp Pro Lys Gln Trp Leu Gln Val Asp Leu Gln Lys Thr
    2210                2215                2220
Met Lys Val Thr Gly Ile Ile Thr Gln Gly Val Lys Ser Leu Phe Thr
2225                2230                2235                2240
Ser Met Phe Val Lys Glu Phe Leu Ile Ser Ser Ser Gln Asp Gly His
                2245                2250                2255
His Trp Thr Gln Ile Leu Tyr Asn Gly Lys Val Lys Val Phe Gln Gly
            2260                2265                2270
Asn Gln Asp Ser Ser Thr Pro Met Met Asn Ser Leu Asp Pro Pro Leu
        2275                2280                2285
Leu Thr Arg Tyr Leu Arg Ile His Pro Gln Ile Trp Glu His Gln Ile
    2290                2295                2300
Ala Leu Arg Leu Glu Ile Leu Gly Cys Glu Ala Gln Gln Gln Tyr
2305                2310                2315
```

( 2 ) INFORMATION FOR SEQ ID NO:7:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:7:

CCTTCCTTTA TCCAAATACG TAGATCAAGA GGAAATTGAC          40

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:8:

GTAGCGTTGC CAAGAAGCAC CCTAAGACG          29

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:9:

GAAGAGTAGT ACGAGTTATT TCTCTGGGTT CAATGAC          37

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:10:

CCTTTATCCA AATACGTAGC GTTGCCAAG AAG          33

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:11:

AARCAYCCNA ARACNTGGG          19

(2) INFORMATION FOR SEQ ID NO:12:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: Other nucleic acid (iii) HYPOTHETICAL: NO (iv) ANTI-SENSE: NO (xi) SEQUENCE DESCRIPTION: SEQ ID NO:12:

GCTCGCACTA GGGGGTCTTG AATTC                                                                25